United States Patent
Couroux et al.

(10) Patent No.: US 9,125,834 B2
(45) Date of Patent: *Sep. 8, 2015

(54) DYE COMPOSITION COMPRISING A HETEROCYCLIC OXIDATION BASE AND A 4-AMINOINDOLE COUPLER

(71) Applicant: L'OREAL, Paris (FR)

(72) Inventors: Anne-Marie Couroux, Saint-Ouen-l'Amône (FR); Aziz Fadli, Chelles (FR); Valérie Nicou, Clichy (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/217,718

(22) Filed: Mar. 18, 2014

(65) Prior Publication Data

US 2014/0259454 A1  Sep. 18, 2014

Related U.S. Application Data

(63) Continuation of application No. 13/993,428, filed as application No. PCT/EP2011/072742 on Dec. 14, 2011, now abandoned.

(60) Provisional application No. 61/431,934, filed on Jan. 12, 2011, provisional application No. 61/431,938, filed on Jan. 12, 2011, provisional application No. 61/432,291, filed on Jan. 13, 2011.

(30) Foreign Application Priority Data

Dec. 17, 2010 (FR) ...................................... 10 60750
Dec. 17, 2010 (FR) ...................................... 10 60751
Dec. 17, 2010 (FR) ................................... 10 607453

(51) Int. Cl.
*A61Q 5/10* (2006.01)
*A61K 8/49* (2006.01)

(52) U.S. Cl.
CPC . *A61K 8/49* (2013.01); *A61K 8/492* (2013.01); *A61K 8/494* (2013.01); *A61K 8/4946* (2013.01); *A61Q 5/10* (2013.01); *A61K 2800/88* (2013.01)

(58) Field of Classification Search
CPC ........... A61Q 5/10; A61K 8/49; A61K 8/492; A61K 8/494; A61K 8/4946; A61K 8/4913; A61K 2800/88
USPC ....................... 8/405, 406, 408, 409, 570, 573
See application file for complete search history.

(56) References Cited

U.S. PATENT DOCUMENTS

| | | | |
|---|---|---|---|
| 4,003,699 A | 1/1977 | Rose et al. | |
| RE30,199 E | 1/1980 | Rose et al. | |
| 4,823,985 A | 4/1989 | Grollier et al. | |
| 5,061,289 A | 10/1991 | Clausen et al. | |
| 5,380,340 A | 1/1995 | Neunhoeffer et al. | |
| 5,457,200 A | 10/1995 | Zimmermann et al. | |
| 5,534,267 A | 7/1996 | Neunhoeffer et al. | |
| 5,645,609 A * | 7/1997 | Andrean et al. | 8/405 |
| 5,663,366 A | 9/1997 | Neunhoeffer et al. | |
| 5,752,982 A | 5/1998 | Lang et al. | |
| 5,766,576 A | 6/1998 | Lowe et al. | |
| 5,785,717 A | 7/1998 | Maubru et al. | |
| 5,938,792 A | 8/1999 | Lang et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 2002/0050013 A1 | 5/2002 | Vidal et al. | |
| 2003/0019051 A9 | 1/2003 | Vidal et al. | |
| 2005/0081313 A1 | 4/2005 | Fadli et al. | |
| 2005/0166335 A1 | 8/2005 | Vidal et al. | |
| 2007/0136959 A1 | 6/2007 | Fadli | |
| 2007/0143935 A1 | 6/2007 | Fadli et al. | |
| 2008/0071092 A1 | 3/2008 | Vidal et al. | |
| 2010/0115711 A1 | 5/2010 | Fadli et al. | |

FOREIGN PATENT DOCUMENTS

WO   WO 2010/133640 A2 * 11/2010 ............... A61K 8/41

OTHER PUBLICATIONS

STIC Search Report dated Jun. 24, 2014.*

* cited by examiner

*Primary Examiner* — Eisa Elhilo
(74) *Attorney, Agent, or Firm* — The Marbury Law Group, PLLC

(57) ABSTRACT

The present invention relates to a composition for dyeing keratin fibers, comprising, in a medium that is suitable for dyeing keratin fibers: at least one oxidation base chosen from 4,5-diaminopyrazole, pyrazolopyrimidine and diamino-N,N-dihydropyrazolone heterocyclic bases, and at least one coupler chosen from the compounds of formula (II) and the addition salts thereof, solvates thereof and solvates of the salts thereof: The composition of the present invention makes it possible in particular to obtain colorations in varied shades, which are strong, chromatic, powerful, aesthetic, sparingly selective and resistant to the various attacking factors to which the hair may be subjected.

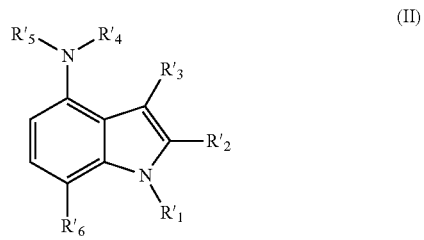

(II)

26 Claims, No Drawings

DYE COMPOSITION COMPRISING A HETEROCYCLIC OXIDATION BASE AND A 4-AMINOINDOLE COUPLER

This is a Continuation of U.S. patent application Ser. No. 13/993,428 filed on Jun. 12, 2013, which is a national stage application of PCT/EP2011/072742, filed internationally on Dec. 14, 2011, which claims priority to U.S. Provisional Application Nos. 61/431,934, filed on Jan. 12, 2011; 61/431,938, filed on Jan. 12, 2011 and 61/432,291, filed on Jan. 13, 2011; as well as French Application Nos. FR 1060750, filed on Dec. 17, 2010; FR 1060751, filed on Dec. 17, 2010 and FR 1060753, filed on Dec. 17, 2010.

The invention relates to a dye composition comprising at least one particular heterocyclic oxidation base and at least one suitably selected 4-aminoindole coupler, and also to the dyeing process using this composition.

It is known practice to dye keratin fibres, and in particular human keratin fibres such as the hair, with dye compositions containing oxidation dye precursors, which are generally known as oxidation bases, such as ortho- or para-phenylenediamines, ortho- or para-aminophenols and heterocyclic compounds. These oxidation bases are colourless or weakly coloured compounds, which, when combined with oxidizing products, may give rise to coloured compounds via a process of oxidative condensation.

It is also known that the shades obtained with these oxidation bases may be varied by combining them with couplers or coloration modifiers, the latter being chosen especially from aromatic meta-diamines, meta-aminophenols, meta-diphenols and certain heterocyclic compounds such as indole compounds.

The variety of molecules used as oxidation bases and couplers allows a wide range of colours to be obtained.

The "permanent" coloration obtained by means of these oxidation dyes must moreover satisfy a certain number of requirements. Thus, it should have no toxicological drawbacks, it should allow shades to be obtained in the desired intensity, and it should show good resistance to external agents such as light, bad weather, washing, permanent waving treatments, perspiration and rubbing.

The dyes should also allow grey hair to be covered and, finally, they should be as unselective as possible, i.e. they should produce the smallest possible differences in coloration along the same keratin fibre, which in general is differently sensitized (i.e. damaged) between its end and its root.

It is known practice to use oxidation bases derived from 3-aminopyrazolo[1,5-a]pyridine in the field of dyeing keratin fibres, especially the oxidation bases of formulae (I) and (II) below. In particular, such bases are disclosed in documents EP 1 792 903 and EP 1 792 606.

It is already known practice from document EP 0 728 464 to use diaminopyrazole derivatives as oxidation bases in combination with heterocyclic couplers, and in particular indole derivatives.

It is also known practice to use oxidation bases of the diamino-N,N-dihydropyrazolone type in the field of dyeing keratin fibres, especially the hair. In particular, such a base is described in document EP 1 550 656.

It is also known practice from document WO 92/18093 to use compounds of aminoindole type, and in particular 7-methyl-1H-indol-4-amine and 7-ethyl-1H-indol-4-amine, for dyeing keratin fibres, and in particular the hair.

However, the prior art dye compositions lead to colorations that are not entirely satisfactory in terms of intensity, chromaticity, selectivity and fastness with respect to external agents.

The aim of the present invention is to obtain a hair dye composition that has improved dyeing properties in terms of intensity and/or chromaticity and/or selectivity and/or resistance to external agents.

This aim is achieved with the present invention, one subject of which is a composition for dyeing keratin fibres, comprising, in a cosmetically acceptable medium:
at least one oxidation base chosen from the 4,5-diaminopyrazole derivatives of formula (I) and the addition salts thereof, solvates thereof and solvates of the salts thereof:

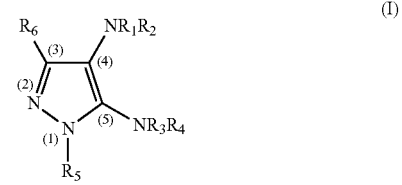

(I)

in which:
$R_1$, $R_2$, $R_3$, $R_4$, $R_5$ and $R_6$, which may be identical or different, represent a hydrogen atom or; a $C_1$-$C_6$ alkyl radical which is unsubstituted or substituted with at least one substituent chosen from OR, NHR, NRR', SR, SOR, $SO_2R$, COR, COOH, $CONH_2$, CONHR, CONRR', $PO(OH)_2$, SH, $SO_3X$, a non-cationic heterocycle, Cl, Br or I, X denoting a hydrogen atom, Na, K or $NH_4$, and R and R', which may be identical or different, representing a $C_1$-$C_4$ alkyl or alkenyl; a $C_2$-$C_4$ hydroxyalkyl radical; a $C_2$-$C_4$ aminoalkyl radical; a phenyl radical; a phenyl radical substituted with a halogen atom or a $C_1$-$C_4$ alkyl, $C_1$-$C_4$ alkoxy, nitro, trifluoromethyl, amino or $C_1$-$C_4$ alkylamino radical; a benzyl radical; a benzyl radical substituted with a halogen atom or with a $C_1$-$C_4$ alkyl, $C_1$-$C_4$ alkoxy, methylenedioxy or amino radical; a radical having the following formula:

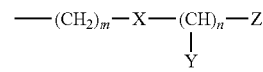

in which m and n are integers, which may be identical or different, between 0 and 3 inclusive, X represents an oxygen atom or an NH group, Y represents a hydrogen atom or a $C_1$-$C_4$ alkyl radical, and Z represents a methyl radical when n is equal to 0, or Z represents a $C_1$-$C_4$ alkyl radical or a group OR or NR"R''' when n is greater than or equal to 1, R" and R''', which may be identical or different, denoting a hydrogen atom or a $C_1$-$C_4$ alkyl radical; or $R_5$ forms, with the nitrogen atom of the group $NR_3R_4$ in position 5, a heterocycle that is at least 4-membered;
at least one of the radicals $R_1$, $R_2$, $R_3$ and $R_4$ represents a hydrogen atom;
the aminopyrazolopyridine oxidation bases chosen from the bases of formula (II) and the bases of formula (III), and also the addition salts thereof, solvates thereof and solvates of the salts thereof:

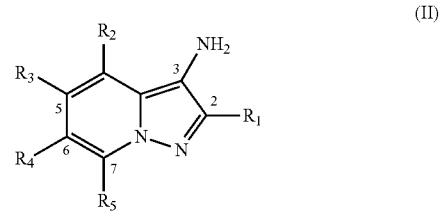

(II)

in which:
$R_1$, $R_2$, $R_3$, $R_4$ and $R_5$, which may be identical or different, represent a hydrogen or halogen atom; a radical —$NHSO_3H$; a hydroxyl radical; a radical ($C_1$-$C_4$)alkyl; a radical (C₁-C₄)alkoxy; a radical (C₁-C₄)alkylthio; mono (C₁-C₄)alkylamino; a radical di(C₁-C₄)alkylamino in which the two alkyl groups may form, together with the nitrogen atom to which they are attached, a ring that may be interrupted with one or more nitrogen, oxygen or sulfur atoms; a heterocycle; a nitro radical; a phenyl radical; a carbonyl radical; a (C₁-C₄)alkoxycarbonyl radical; a carboxamido radical; a cyano radical; an amino radical; a sulfonyl radical; a radical —CO₂H, a radical —SO₃H; a radical —PO₃H₂; a radical —PO₄H₂; or a group

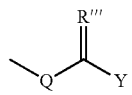

in which R''' represents an oxygen or nitrogen atom, Q represents an oxygen atom, a group NH or NH(C₁-C₄)alkyl, and Y represents a hydroxyl, amino, C₁-C₄ alkyl, (C₁-C₄)alkoxy, (C₁-C₄)alkylamino or di(C₁-C₄)alkylamino radical;

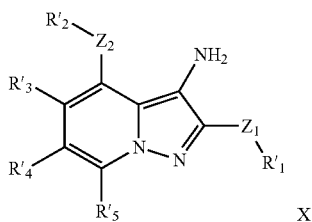

(III)

in which:
$Z_1$ and $Z_2$ independently represent:
a covalent single bond;
a divalent radical chosen from:
a radical —O(CH₂)$_p$—, p denoting an integer ranging from 0 to 6;
a radical —NR'₆(CH₂)$_q$(C₆H₄)$_t$—, q denoting an integer ranging from 0 to 6 and t denoting 0 or 1, $R_6'$ representing a hydrogen atom or a C₁-C₆ alkyl radical optionally substituted with one or more hydroxyl groups;
$Z_1$ may also represent a divalent radical —S—, —SO— or —SO₂— when $R_1'$ is a methyl radical;
$R_1'$ and $R_2'$ independently represent:
a hydrogen;
a C₁-C₁₀ alkyl radical, which is optionally substituted and optionally interrupted with a heteroatom or a group chosen from O, N, Si, S, SO and SO₂;
a halogen;
an SO₃H radical;
a 5- to 8-membered ring which is substituted or unsubstituted, saturated, unsaturated or aromatic, optionally containing one or more heteroatoms or groups chosen from N, O, S, SO₂ and —CO—, the ring possibly being cationic and/or substituted with a cationic radical;
a group —N⁺R₁₇R₁₈R₁₉, R₁₇, R₁₈ and R₁₉ being linear or branched C₁-C₅ alkyls optionally substituted with one or more hydroxyl groups;
when $Z_1$ or, respectively, $Z_2$ represents a covalent bond, then $R_1'$ or, respectively, $R_2'$ may also represent a radical:
optionally substituted C₁-C₆ alkylcarbonyl;
—O—CO—R, —CO—O—R, NR—CO—R' or —CO—NRR' in which R and R' independently represent a hydrogen atom or an optionally substituted C₁-C₆ alkyl radical;

$R_3'$, $R_4'$ and $R_5'$, which may be identical or different, represent:
a hydrogen atom;
a hydroxyl radical;
a C₁-C₆ alkoxy radical;
a C₁-C₆ alkylthio radical;
an amino radical;
a monoalkylamino radical;
a C₁-C₆ dialkylamino radical in which the alkyl radicals may form, with the nitrogen atom to which they are attached, a saturated, unsaturated, aromatic or non-aromatic 5- to 8-membered heterocycle, which may contain one or more heteroatoms or groups chosen from N, O, S, SO₂ and CO, the heterocycle possibly being cationic, and/or substituted with a cationic radical;
an optionally substituted C₁-C₆ alkylcarbonyl radical;
a radical —O—CO—R, —CO—O—R, NR—CO—R' or —CO—NRR' with R and R' as defined previously;
a halogen;
an SO₃H radical;
an optionally substituted C₁-C₄ alkyl radical;
a saturated, unsaturated or aromatic, optionally substituted carbon-based ring;
$R_3'$, $R_4'$ and $R_5'$ may form in pairs a partially saturated or unsaturated ring;
X represents an ion or group of ions that provides the electronegativity of the derivative of formula (II);
with the proviso that at least one of the groups $R_1'$ and $R_2$ represents a cationic radical;
the oxidation bases chosen from the diamino-N,N-dihydropyrazolone derivatives of formula (IV), and also the addition salts thereof, solvates thereof and solvates of the salts thereof:

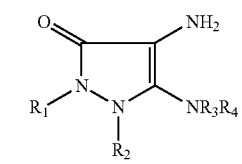

(IV)

in which:
$R_1$, $R_2$, $R_3$ and $R_4$, which may be identical or different, represent:
a linear or branched C₁-C₆ alkyl radical optionally substituted with one or more radicals chosen from the group consisting of a radical OR₅, a radical NR₆R₇, a carboxyl radical, a sulfonic radical, a carboxamido radical CONR₆R₇, a sulfonamido radical SO₂NR₆R₇, a heteroaryl, an aryl optionally substituted with one or more (C₁-C₄)alkyl, hydroxyl, C₁-C₂ alkoxy, amino or (di)alkyl(C₁-C₂)amino groups;
an aryl radical optionally substituted with one or more (C₁-C₄)alkyl, hydroxyl, C₁-C₂ alkoxy, amino or (di)alkyl(C₁-C₂)amino;
a 5- or 6-membered heteroaryl radical, optionally substituted with one or more radicals chosen from (C₁-C₄)alkyl and (C₁-C₂)alkoxy;
$R_3$ and $R_4$ may also represent a hydrogen atom;
$R_5$, $R_6$ and $R_7$, which may be identical or different, represent:
a hydrogen atom;
a linear or branched C₁-C₄ alkyl radical optionally substituted with one or more radicals chosen from hydroxyl, C₁-C₂ alkoxy, carboxamido CONR₈R₉, sulfonyl SO₂R₈, aryl optionally substituted with a (C₁-C₄)alkyl, hydroxyl, $C_1$-$C_2$ alkoxy, amino or (di)alkyl($C_1$-$C_2$) amino; aryl optionally substituted with a ($C_1$-$C_4$)alkyl, hydroxyl, $C_1$-$C_2$ alkoxy, amino or (di)alkyl($C_1$-$C_2$) amino;

$R_6$ and $R_7$, which may be identical or different, may also represent a carboxamido radical $CONR_8R_9$; a sulfonyl radical $SO_2R_8$;

$R_8$ and $R_9$, which may be identical or different, represent a hydrogen atom; a linear or branched $C_1$-$C_4$ alkyl radical optionally substituted with one or more hydroxyl or $C_1$-$C_2$ alkoxy;

$R_1$ and $R_2$, on the one hand, and $R_3$ and $R_4$, on the other hand, may form, with the nitrogen atom(s) to which they are attached, a saturated or unsaturated 5- to 7-membered heterocycle optionally substituted with one or more radicals chosen from the group consisting of halogen atoms and amino, (di)alkyl($C_1$-$C_4$)amino, hydroxyl, carboxyl, carboxamido and ($C_1$-$C_2$)alkoxy radicals, $C_1$-$C_4$ alkyl radicals optionally substituted with one or more hydroxyl, amino, (di)alkylamino, alkoxy, carboxyl or sulfonyl radicals;

$R_3$ and $R_4$ may also form, together with the nitrogen atom to which they are attached, a 5- or 7-membered heterocycle in which the carbon atoms may be replaced with an optionally substituted oxygen or nitrogen atom;

at least one coupler chosen from the 4-aminoindole derivatives of formula (IV), and also the addition salts thereof, solvates thereof and solvates of the salts thereof:

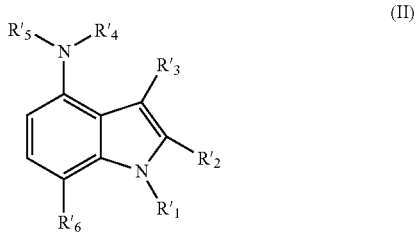

(II)

in which:

$R'_1$ represents:
a hydrogen atom;
a linear or branched saturated $C_1$-$C_6$ alkyl radical, optionally interrupted with an oxygen atom or a radical $NR'_7$, optionally substituted with a radical chosen from OH and $NR'_7R'_8$;

$R'_2$ and $R'_3$, which may be identical or different, represent:
a hydrogen atom;
a $C_1$-$C_6$ and preferably $C_1$-$C_4$ alkyl radical, optionally substituted with one or more hydroxyl radicals;
a $C_1$-$C_6$ alkyl carboxylate radical;
a carboxyl radical;
a radical $CONR'_7R'_8$;

$R'_4$ and $R'_5$, which may be identical or different, represent:
a hydrogen atom;
a $C_1$-$C_6$ alkyl radical;

$R_6'$ represents:
a halogen;
a linear or branched $C_1$-$C_{10}$ alkyl radical, optionally interrupted with a heteroatom chosen from O or a radical $NR'_9$, and/or optionally substituted with one or more radicals, which may be identical or different, chosen from OH and $NR'_7R'_8$;
a carboxyl radical;
a $C_1$-$C_{10}$ alkyl carboxylate radical;

a radical $CONR'_7R'_8$;
a $C_1$-$C_{10}$ alkoxy or $C_1$-$C_{10}$ (poly)hydroxyalkoxy radical;
a (poly)($C_1$-$C_{10}$)alkoxy($C_1$-$C_{10}$)alkyloxy radical;
a radical O-Ak-$NR'_9R'_{10}$ with Ak=linear $C_1$-$C_8$ or branched $C_3$-$C_3$ divalent alkylene radical, optionally interrupted with one or more oxygen atoms and/or groups $NR'_7$;

$R'_7$ and $R'_8$, which may be identical or different, represent:
a hydrogen atom;
a $C_1$-$C_8$ alkyl radical optionally substituted with one or more hydroxyl radicals;

$R'_9$ and $R'_{10}$, which may be identical or different, represent a linear or branched, saturated or unsaturated $C_1$-$C_4$ alkyl;

$R'_9$ and $R'_{10}$ may form, with the nitrogen that bears them, a saturated or unsaturated 5- to 8-membered heterocycle, one of the chain members possibly being an oxygen atom or a radical $NR'_{11}$ with $R'_{11}$ =H or $C_1$-$C_4$ alkyl, optionally substituted with one or more radicals chosen from OH and $NR'_7R'_8$.

A subject of the invention is also a dyeing process using this composition.

Another subject of the invention is the use of the composition of the present invention for dyeing keratin fibres, and in particular human keratin fibres such as the hair.

The invention also relates to multi-compartment devices comprising compositions using at least one oxidation base chosen from the compounds of formulae (I), (II) and (III), addition salts thereof, solvates thereof and solvates of the salts thereof, and at least one coupler chosen from the compounds of formula (IV), and also the addition salts thereof, solvates thereof and solvates of the salts thereof.

The composition of the present invention makes it possible in particular to obtain a composition for dyeing keratin fibres that is suitable for use in oxidation dyeing and that can produce colorations in varied shades, which are strong or chromatic, powerful, aesthetic, sparingly selective, and resistant to the various attacking factors to which the hair may be subjected, such as shampoo, sweat, permanent reshaping and light. In particular, the composition in accordance with the invention leads to particularly chromatic shades.

In the context of the present invention, the term "at least one" is equivalent to "one or more".

The present invention also covers the mesomeric forms and the stereoisomers of the various oxidation dyes of the invention.

It should be noted that, in the text hereinbelow, unless otherwise indicated, the limits of a range of values are included in that range.

Unless otherwise indicated, the limits of the ranges of values that are given in the context of the present invention are included in these ranges.

In the context of the invention, and unless indicated otherwise, the term "alkyl" used for the alkyl radicals and also for the groups comprising an alkyl part means a linear or branched carbon-based chain comprising from 1 to 4 carbon atoms, which is unsubstituted or substituted with one or more heterocycles, or with one or more phenyl groups or with one or more groups chosen from halogen atoms such as chlorine, bromine, iodine and fluorine; hydroxyl, alkoxy, amino, carbonyl, carboxamido, sulfonyl, —$CO_2H$, —$SO_3H$, —$PO_3H_2$, —$PO_4H_2$, —$NHSO_3H$, sulfonamide, mono($C_1$-$C_4$)alkylamino or tri($C_1$-$C_4$)alkylammonium radicals, or alternatively with a di($C_1$-$C_4$)alkylamino radical in which the two alkyl groups may form, together with the nitrogen atom of the said di($C_1$-$C_4$)alkylamino group to which they are attached, a ring that may be interrupted with one or more nitrogen, oxygen or sulfur atoms.

Similarly, according to the invention, the term "alkoxy" used for the alkoxy radicals and also for the groups comprising an alkoxy part means a linear or branched O-carbon-based chain comprising from 1 to 4 carbon atoms, which is unsubstituted or substituted with one or more groups chosen from heterocycles; halogen atoms such as chlorine, bromine, iodine and fluorine; hydroxyl, amino, carbonyl, carboxamido, sulfonyl, —$CO_2H$, —$SO_3H$, —$PO_3H_2$, —$PO_4H_2$, —$NHSO_3H$, sulfonamide, mono($C_1$-$C_4$)alkylamino or tri ($C_1$-$C_4$)alkylammonium radicals, or alternatively with a di($C_1$-$C_4$)alkylamino radical in which the two alkyl groups may form, together with the nitrogen atom of the said di($C_1$-$C_4$)alkylamino group to which they are attached, a ring that may be interrupted with one or more nitrogen, oxygen or sulfur atoms.

According to the invention, the term "heterocycle" means an aromatic or non-aromatic 5-, 6-, 7- or 8-membered ring containing from 1 to 3 heteroatoms chosen from nitrogen, sulfur and oxygen atoms. These heterocycles may be fused to other heterocycles or to a phenyl group. They may be substituted with a halogen atom; a ($C_1$-$C_4$)alkyl radical; a ($C_1$-$C_4$) alkoxy radical; a hydroxyl radical; an amino radical; a ($C_1$-$C_4$)alkylamino radical; a di($C_1$-$C_4$)alkylamino radical in which the two alkyl groups may form, together with the nitrogen atom to which they are attached, a ring that may be interrupted with one or more nitrogen, oxygen or sulfur atoms. These heterocycles may also be quaternized with a ($C_1$-$C_4$)alkyl radical.

Among these optionally fused heterocycles, examples that may especially be mentioned include the following rings: thiadiazole, triazole, isoxazole, oxazole, azaphosphole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine, aziridine, 3-(2-hydroxyethyl)benzothiazol-3-ium, 1-(2-hydroxyethyl) pyridinium.

According to the invention, the term "phenyl" means a phenyl radical that is unsubstituted or substituted with one or more cyano, carbonyl, carboxamido, sulfonyl, —$CO_2H$, —$SO_3H$, —$PO_3H_2$, —$PO_4H_2$, hydroxyl, amino or mono($C_1$-$C_4$)alkylamino radicals, or di($C_1$-$C_4$)alkylamino radicals in which the two alkyl groups may form, together with the nitrogen atom of the said di($C_1$-$C_4$)alkylamino group to which they are attached, a ring that may be interrupted with one or more nitrogen, oxygen or sulfur atoms.

Among the groups

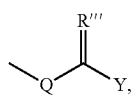

mention may be made especially of acetamide, dimethylurea, O-methylcarbamate, methylcarbonate and N-dimethylcarbamate groups, and the esters.

The compounds of formula (I) may be in the form of addition salts chosen especially from addition salts with an acid such as the hydrochlorides, hydrobromides, sulfates, citrates, succinates, tartrates, lactates, tosylates, benzenesulfonates, phosphates and acetates. The compounds of formula (I) bearing an acidic substituent may be in the form of addition salts with a base, such as the sodium, potassium, ammonium or alkanolamine salts.

They may also be in the form of solvates, for example a hydrate or a solvate of a linear or branched alcohol such as ethanol or isopropanol.

As examples of derivatives of formula (I) that may be used according to the invention, mention may be made of the compounds described in patents DE-A-38 43 892 and DE-A-41 33 957 and patent applications WO 94/08969, WO 94/08970, FR-A-2 733 749 and DE-A-195 43 988, for instance 4,5-diamino-1-methylpyrazole, 4,5-diamino-1-(2-hydroxyethyl)pyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole and 4-amino-5-(2'-aminoethyl)amino-1,3-dimethylpyrazole, the addition salts thereof, solvates thereof and solvates of the salts thereof.

According to one particular embodiment, the diaminopyrazole of formula (I) is such that $R_6$ is hydrogen. According to this variant, $R_1$, $R_2$, $R_3$ and $R_4$ represent a hydrogen atom or a $C_1$-$C_4$ alkyl radical and $R_5$ is an alkyl, hydroxyalkyl or alkoxyalkyl radical.

Preference is given even more particularly to 4,5-diamino-1-(2-hydroxyethyl)-1H-pyrazole and salts thereof, solvates thereof and solvates of the salts thereof such as 4,5-diamino-1-(2-hydroxyethyl)-1H-pyrazole sulfate, of the following formula:

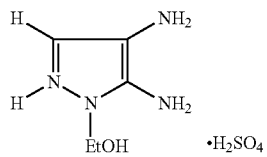

Among the compounds of formula (II) above, preference is given to the 3-aminopyrazolo[1,5-a]pyridines corresponding to formula (II') below, and also the addition salts thereof, solvates thereof and solvates of the salts thereof:

(II')

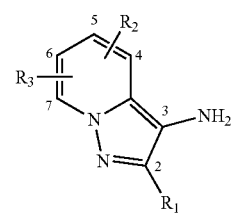

in which:
$R_1$, $R_2$ and $R_3$, which may be identical or different, represent a hydrogen or halogen atom; a hydroxyl radical; a ($C_1$-$C_4$) alkyl radical; a ($C_1$-$C_4$)alkylthio radical; a ($C_1$-$C_4$)alkoxy radical; an —$NHSO_3H$ radical; an amino radical; a ($C_1$-$C_4$)alkylamino radical; a di($C_1$-$C_4$)alkylamino radical in which the two alkyl groups may form, together with the nitrogen atom to which they are attached, a ring that may be interrupted with one or more nitrogen, oxygen or sulfur atoms; a heterocycle as defined previously; a sulfonamide radical, a carbonyl radical, a $(C_1$-$C_4)$alkoxycarbonyl radical, a carboxamido radical, or a group of formula:

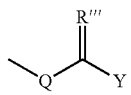

in which R''' represents an oxygen or nitrogen atom, Q represents an oxygen atom, a group NH or NH($C_1$-$C_4$)alkyl, and Y represents a hydroxyl, amino, $C_1$-$C_4$alkyl, ($C_1$-$C_4$)alkoxy, ($C_1$-$C_4$)alkylamino or di($C_1$-$C_4$)alkylamino radical.

Among the 3-aminopyrazolo[1,5-a]pyridines of formula (II), which may be used as oxidation base in the dye compositions in accordance with the invention, mention may be made especially of:

pyrazolo[1,5-a]pyridin-3-ylamine;
2-acetylaminopyrazolo[1,5-a]pyridin-3-ylamine;
2-morpholin-4-ylpyrazolo[1,5-a]pyridin-3-ylamine;
3-aminopyrazolo[1,5-a]pyridine-2-carboxylic acid;
2-methoxypyrazolo[1,5-a]pyridin-3-ylamino;
(3-aminopyrazolo[1,5-a]pyridin-7-yl)methanol;
2-(3-aminopyrazolo[1,5-a]pyridin-5-yl)ethanol;
2-(3-aminopyrazolo[1,5-a]pyridin-7-yl)ethanol;
(3-aminopyrazolo[1,5-a]pyridin-2-yl)methanol;
3,6-diaminopyrazolo[1,5-a]pyridine;
3,4-diaminopyrazolo[1,5-a]pyridine;
pyrazolo[1,5-a]pyridine-3,7-diamine;
7-morpholin-4-ylpyrazolo[1,5-a]pyridin-3-ylamine;
pyrazolo[1,5-a]pyridine-3,5-diamine;
5-morpholin-4-ylpyrazolo[1,5-a]pyridin-3-ylamine;
2-[(3-aminopyrazolo[1,5-a]pyridin-5-yl)(2-hydroxyethyl) amino]ethanol;
2-[(3-aminopyrazolo[1,5-a]pyridin-7-yl)(2-hydroxyethyl) amino]ethanol;
3-aminopyrazolo[1,5-a]pyridin-5-ol;
3-aminopyrazolo[1,5-a]pyridin-4-ol;
3-aminopyrazolo[1,5-a]pyridin-6-ol;
3-aminopyrazolo[1,5-a]pyridin-7-ol;
2-methoxy-6,7-dimethylpyrazolo[1,5-a]pyridin-3-amine;
2-[(3-aminopyrazolo[1,5-a]pyridin-2-yl)oxy]ethanol;
4-ethyl-2-methoxy-7-methylpyrazolo[1,5-a]pyridin-3-amine hydrochloride;
1-(3-aminopyrazolo[1,5-a]pyridin-2-yl)pyrrolidin-3-ol;
2,2'-[(3-aminopyrazolo[1,5-a]pyridin-2-yl)imino]diethanol;
2-[(3-aminopyrazolo[1,5-a]pyridin-2-yl)amino]ethanol;
N2-(2-pyridin-3-ylethyl)pyrazolo[1,5-a]pyridine-2,3-diamine;
and the addition salts thereof, solvates thereof and solvates of the salts thereof.

Among the bases described above, 2-[(3-aminopyrazolo[1, 5-a]pyridin-2-yl)oxy]ethanol, and the addition salts thereof with an acid, are particularly preferred.

For the vast majority, the 3-aminopyrazolo[1,5-a]pyridines of formula (II) are compounds that are known in the pharmaceutical field, and are described especially in U.S. Pat. No. 5,457,200. These compounds may be prepared according to synthetic methods that are well known in the literature and as described, for example, in U.S. Pat. No. 5,457,200.

The term "cationic ring or heterocycle" means a ring containing one or more quaternary ammonium groups.

Examples of radicals of the type —N$^+$R$_{17}$R$_{18}$R$_{19}$ that may be mentioned include trimethylammonium, triethylammonium, dimethylethylammonium, diethylmethylammonium, diisopropylmethylammonium, diethylpropylammonium, β-hydroxyethyldiethylammonium, bis(β-hydroxyethyl)methylammonium and tris(β-hydroxyethyl)ammonium radicals.

Examples of cationic heterocyclic radicals include imidazolium, pyridinium, piperazinium, pyrrolidinium, morpholinium, pyrimidinium, thiazolium, benzimidazolium, benzothiazolium, oxazolium, benzotriazolium, pyrazolium, triazolium and benzoxazolium radicals.

Examples of cationic heterocycles that may be mentioned include imidazoliums, pyridiniums, piperaziniums, pyrrolidiniums, morpholiniums, pyrimidiniums, thiazoliums, benzimidazoliums, benzothiazoliums, oxazoliums, benzotriazoliums, pyrazoliums, triazoliums and benzoxazoliums.

The compounds of formula (III) may be optionally salified with strong mineral acids, for instance HCl, HBr, HI, $H_2SO_4$ or $H_3PO_4$, or organic acids, for instance acetic acid, lactic acid, tartaric acid, citric acid, succinic acid, benzenesulfonic acid, para-toluenesulfonic acid, formic acid or methanesulfonic acid.

If they contain anionic groups such as —$CO_2H$, —$SO_3H$, —$PO_3H_2$ or —$PO_4H_2$ groups, the compounds of formula (I) may be salified with alkali metal or alkaline-earth metal hydroxides such as sodium hydroxide or potassium hydroxide, with aqueous ammonia or with organic amines.

The compounds of formula (II) or (II) may also be in the form of solvates, for example a hydrate or a solvate of a linear or branched alcohol such as ethanol or isopropanol.

As examples of derivatives of formula (III), mention may be made of the following compounds in which X$^-$ is as defined previously:

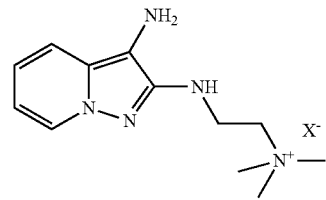

salt of [2-(3-aminopyrazolo[1,5-a]pyridin-2-ylamino)ethyl]trimethylammonium

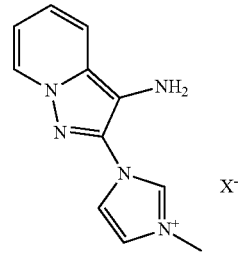

salt of 3-(3-aminopyrazolo[1,5-a]pyridin-2-yl)-1-methyl-3H-imidazol-1-ium

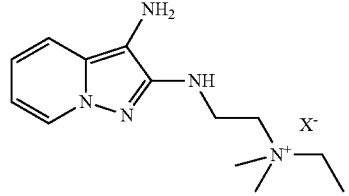

salt of [2-(3-aminopyrazolo[1,5-a]pyridin-2-ylamino)ethyl]ethyldimethylammonium

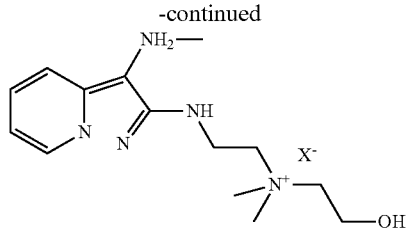

salt of [2-(3-aminopyrazolo[1,5-a]pyridin-2-ylamino)ethyl]-(2-hydroxyethyl)dimethylammonium

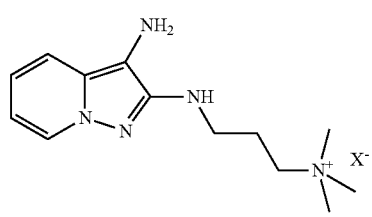

salt of [3-(3-aminopyrazolo[1,5-a]pyridin-2-ylamino)propyl]trimethylammonium

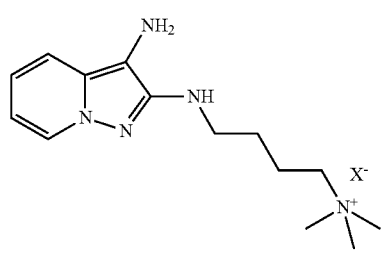

salt of [4-(3-Aminopyrazolo[1,5-a]pyridin-2-ylamino)butyl]trimethylammonium

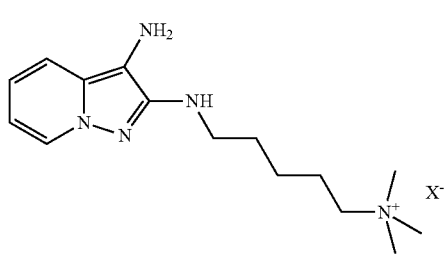

salt of [5-(3-aminopyrazolo[1,5-a]pyridin-2-ylamino)pentyl]trimethylammonium

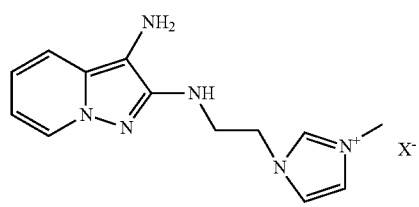

salt of 3-[2-(3-aminopyrazolo[1,5-a]pyridin-2-ylamino)ethyl]-1-methyl-3H-imidazol-1-ium

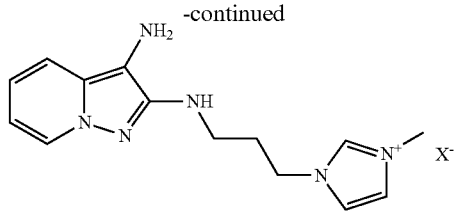

salt of 3-[3-(3-aminopyrazolo[1,5-a]pyridin-2-ylamino)propyl]-1-methyl-3H-imidazol-1-ium

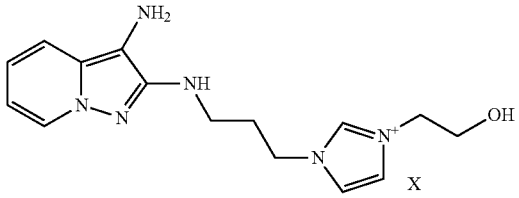

salt of 3-[3-(3-aminopyrazolo[1,5-a]pyridin-2-ylamino)propyl]-1-(2-hydroxyethyl)-3H-imidazol-1-ium

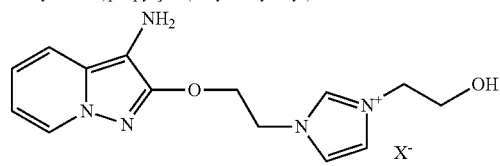

salt of 3-[2-(3-aminopyrazolo[1,5-a]pyridin-2-yloxy)ethyl]-1-(2-hydroxyethyl)-3H-imidazol-1-ium

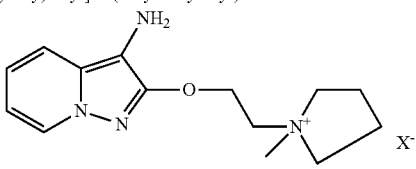

salt of 1-{2-[(3-aminopyrazolo[1,5-a]pyridin-2-yl)oxy]ethyl}-1-methylpyrrolidinium

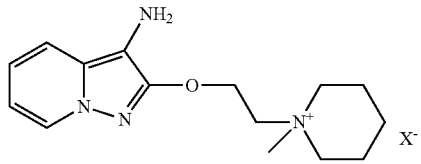

salt of 1-{2-[(3-aminopyrazolo[1,5-a]pyridin-2-yl)oxy]ethyl}-1-methylpiperidinium

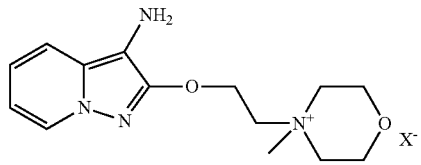

salt of 4-{2-[(3-aminopyrazolo[1,5-a]pyridin-2-yl)oxy]ethyl}-4-methylmorpholin-4-ium

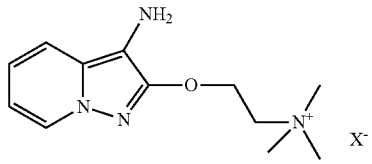

salt of {2-[(3-aminopyrazolo[1,5-a]pyridin-2-yl)oxy]ethyl}trimethylammonium

-continued

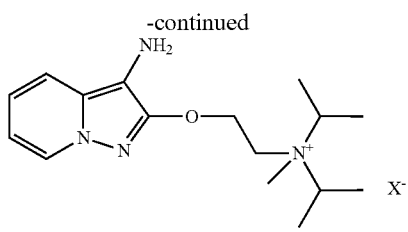

salt of {2-[(3-aminopyrazolo[1,5-a]pyridin-2-yl)oxy]ethyl}diisopropylmethylammonium

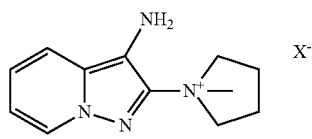

salt of 1-(3-aminopyrazolo[1,5-a]pyridin-2-yl)-1-methylpyrrolidinium

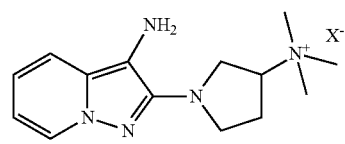

salt of [1-(3-aminopyrazolo[1,5-a]pyridin-2-yl)-pyrrolidin-3-yl]trimethylammonium

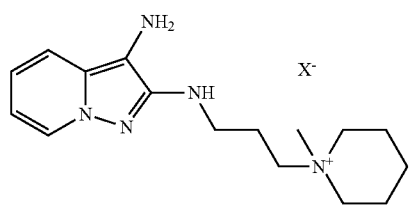

salt of 1-[3-(3-aminopyrazolo[1,5-a]pyridin-2-ylamino)propyl]-1-methylpiperidinium

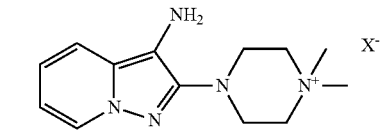

salt of 4-(3-amino-pyrazolo[1,5-a]pyridin-2-yl)-1,1-dimethylpiperazin-1-ium

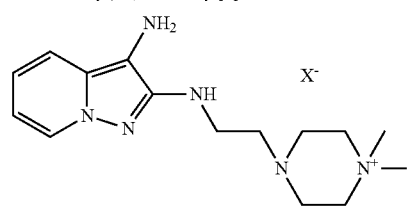

salt of 4-[2-(3-aminopyrazolo[1,5-a]pyridin-2-ylamino)ethyl]-1,1-dimethylpiperazin-1-ium -continued

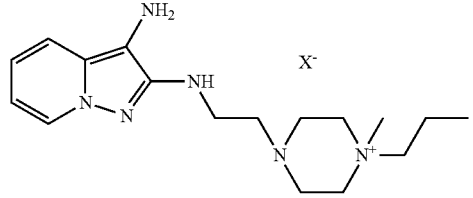

salt of 4-[2-(3-aminopyrazolo[1,5-a]pyridin-2-ylamino)ethyl]-1-methyl-1-propylpiperazin-1-ium

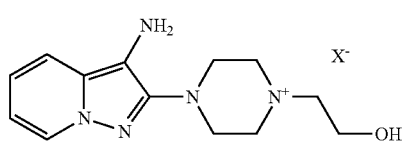

salt of 4-(3-aminopyrazolo[1,5-a]pyridin-2-yl)-1-(2-hydroxyethyl)piperazin-1-ium

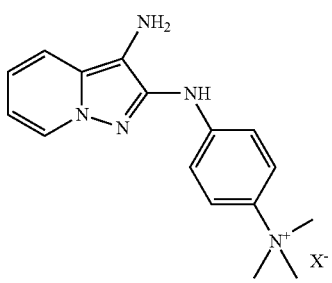

salt of [4-(3-aminopyrazolo[1,5-a]pyridin-2-ylamino)phenyl]trimethylammonium

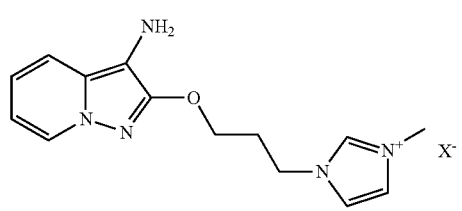

salt of 3-[3-(3-aminopyrazolo[1,5-a]pyridin-2-yloxy)propyl]-1-methyl-3H-imidazol-1-ium

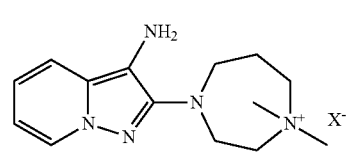

salt of 4-(3-aminopyrazolo[1,5-a]pyridin-2-yl)-1,1-dimethyl-[1,4]diazepan-1-ium

-continued

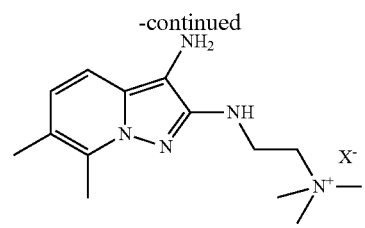

salt of [2-(3-amino-6,7-dimethylpyrazolo
[1,5-a]pyridin-2-ylamino)ethyl]
trimethylammonium

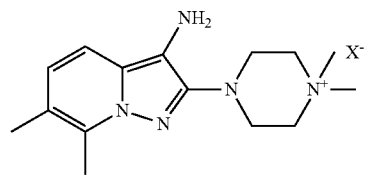

salt of 4-(3-amino-6,7-dimethylpyrazolo
[1,5-a]pyridin-2-yl)-1,1-
dimethylpiperazin-1-ium

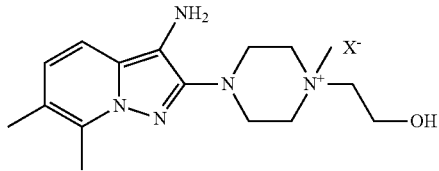

salt of 4-(3-amino-6,7-dimethylpyrazolo
[1,5-a]pyridin-2-yl)-1-(2-hydroxyethyl)-
1-methylpiperazin-1-ium

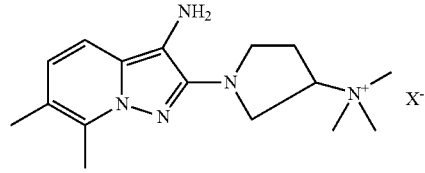

salt of [1-(3-amino-6,7-dimethylpyrazolo[1,5-a]
pyridin-2-yl)pyrrolidin-3-yl]
trimethylammonium

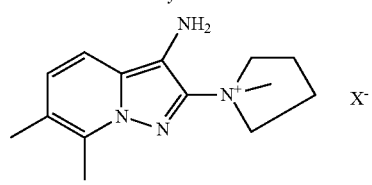

salt of 1-(3-amino-6,7-dimethylpyrazolo
[1,5-a]pyridin-2-yl)-1-
methylpyrrolidinium

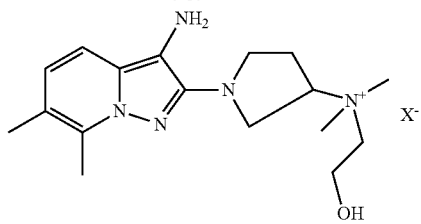

salt of [1-(3-amino-6,7-dimethylpyrazolo[1,5-a]
pyridin-2-yl)pyrrolidin-3-yl]-
(2-hydroxyethyl)
dimethylammonium -continued

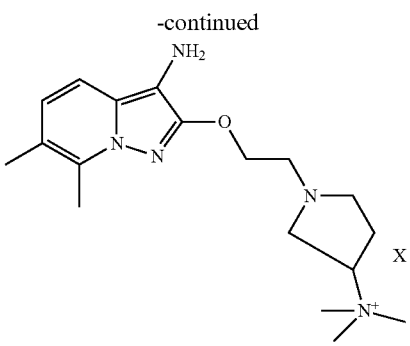

salt of {1-[2-(3-amino-6,7-dimethylpyrazolo[1,5-a]
pyridin-2-yloxy)ethyl]pyrrolidin-3-yl}
trimethylammonium

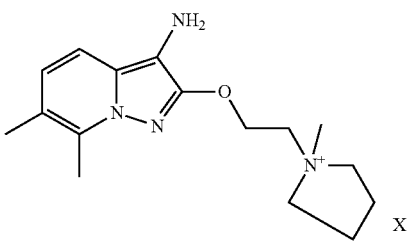

salt of 1-{2-[(3-amino-6,7-dimethylpyrazolo[1,5-a]
pyridin-2-yl)oxy]ethyl}-1-
methylpyrrolidinium

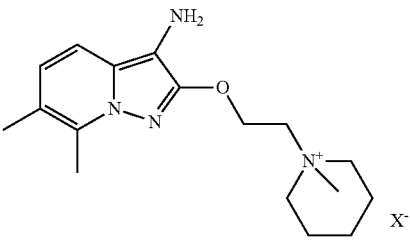

salt of 1-{2-[(3-amino-6,7-dimethylpyrazolo[1,5-a]
pyridin-2-yl)oxy]ethyl}-1-
methylpiperidinium

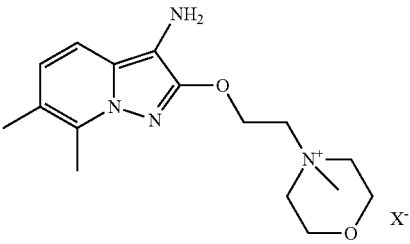

salt of 4-{2-[(3-amino-6,7-dimethylpyrazolo[1,5-a]
pyridin-2-yl)oxy]ethyl}-4-
methylmorpholin-4-ium

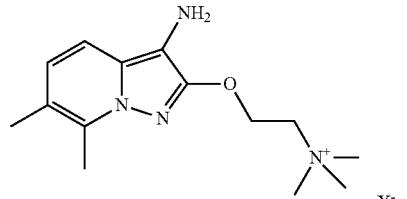

salt of {2-[(3-amino-6,7-dimethylpyrazolo[1,5-a]
pyridin-2-yl)oxy]ethyl}
trimethylammonium -continued

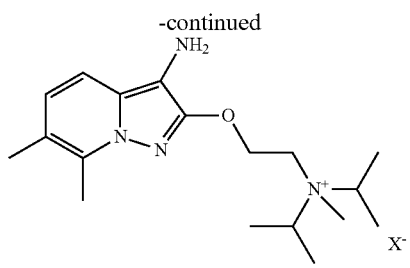

salt of {2-[(3-amino-6,7-dimethylpyrazolo[1,5-a]
pyridin-2-yl)oxy]ethyl}
diisopropylmethylammonium

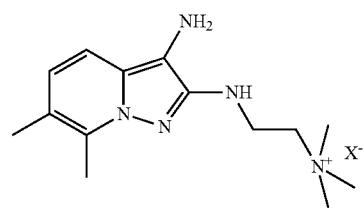

salt of [3-(3-amino-6,7-
dimethylpyrazolo[1,5-a]pyridin-2-
ylamino)propyl]
trimethylammonium

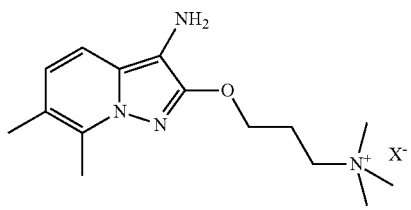

salt of [3-(3-amino-6,7-
dimethylpyrazolo[1,5-a]pyridin-2-
yloxy)propyl]
trimethylammonium

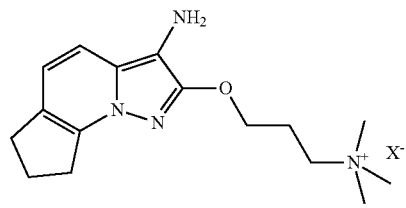

salt of [3-(3-amino-7,8-
dihydro-6H-cyclopenta[e]pyrazolo[1,5-a]
pyridin-2-yloxy)propyl]
trimethylammonium

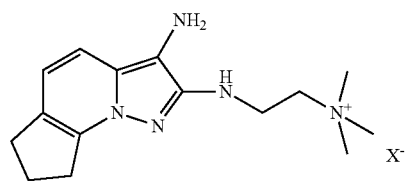

salt of {2-[(3-amino-7,8-
dihydro-6H-cyclopenta[e]pyrazolo[1,5-a]
pyridin-2-yl)amino]ethyl}
trimethylammonium -continued

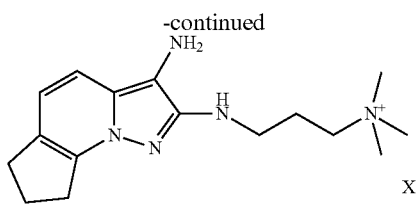

salt of {3-[(3-amino-7,8-
dihydro-6H-cyclopenta[e]pyrazolo[1,5-a]
pyridin-2-yl)amino]propyl}
trimethylammonium

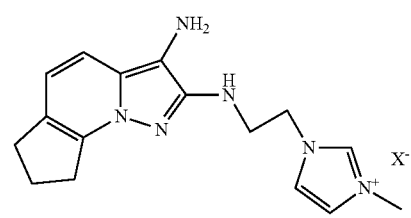

salt of 1-{2-[(3-amino-7,8-
dihydro-6H-cyclopenta[e]pyrazolo[1,5-a]
pyridin-2-yl)amino]ethyl}-3-methyl-1H-
imidazol-3-ium

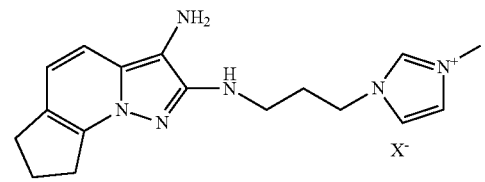

salt of 1-{3-[(3-amino-7,8-
dihydro-6H-cyclopenta[e]pyrazolo[1,5-a]
pyridin-2-yl)amino]propyl}-3-methyl-
1H-imidazol-3-ium

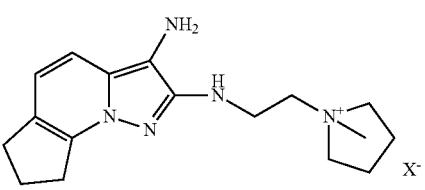

salt of 1-{2-[(3-amino-7,8-
dihydro-6H-cyclopenta[e]pyrazolo[1,5-a]
pyridin-2-yl)amino]ethyl}-1-
methylpyrrolidinium

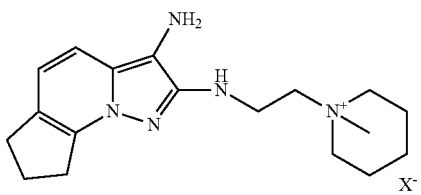

salt of 1-{2-[(3-amino-7,8-
dihydro-6H-cyclopenta[e]pyrazolo[1,5-a]
pyridin-2-yl)amino]ethyl}-1-
methylpiperidinium -continued

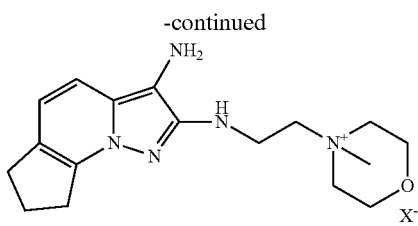

salt of 4-{2-[(3-amino-7,8-dihydro-6H-cyclopenta[e]pyrazolo[1,5-a]pyridin-2-yl)amino]ethyl}-4-methylmorpholin-4-ium

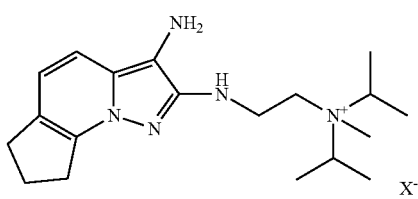

salt of {2-[(3-amino-7,8-dihydro-6H-cyclopenta[e]pyrazolo[1,5-a]pyridin-2-yl)amino]ethyl}diisopropylmethylammonium

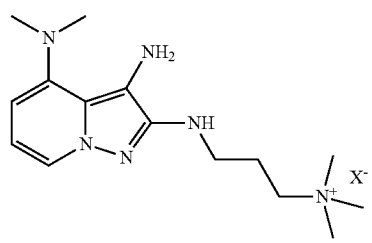

salt of [3-(3-amino-4-dimethylaminopyrazolo[1,5-a]pyridin-2-ylamino)propyl]trimethylammonium

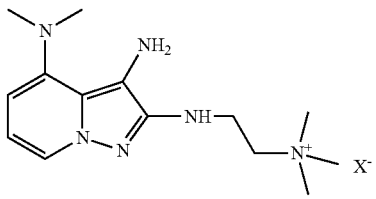

salt of [2-(3-amino-4-dimethylaminopyrazolo[1,5-a]pyridin-2-ylamino)ethyl]trimethylammonium

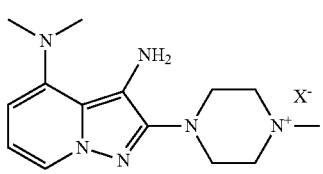

salt of 4-(3-amino-4-dimethylaminopyrazolo[1,5-a]pyridin-2-yl)-1-methylpiperazin-1-ium -continued

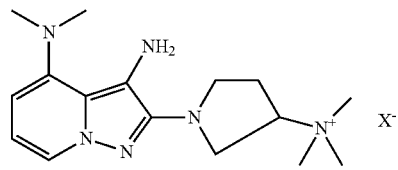

salt of [1-(3-amino-4-dimethylaminopyrazolo[1,5-a]pyridin-2-yl)pyrrolidin-3-yl]trimethylammonium

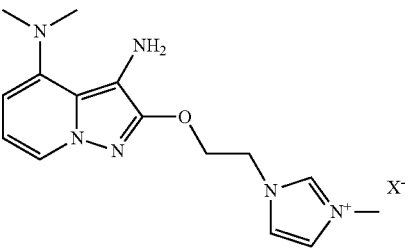

salt of 3-[2-(3-amino-4-dimethylaminopyrazolo[1,5-a]pyridin-2-yloxy)ethyl]-1-methyl-3H-imidazol-1-ium

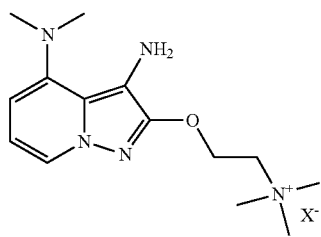

salt of [2-(3-amino-4-dimethylaminopyrazolo[1,5-a]pyridin-2-yloxy)ethyl]trimethylammonium

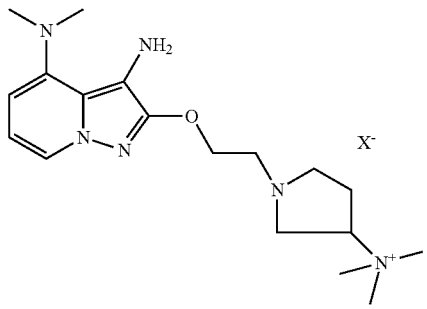

salt of {1-[2-(3-amino-4-dimethylaminopyrazolo[1,5-a]pyridin-2-yloxy)ethyl]pyrrolidin-3-yl}trimethylammonium

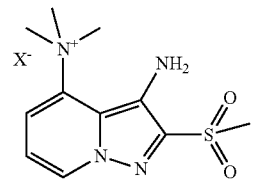

salt of (3-amino-2-methanesulfonylpyrazolo[1,5-a]pyridin-4-yl)trimethylammonium

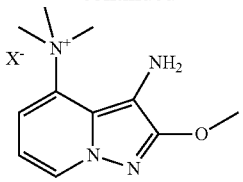

salt of (3-amino-2-methoxypyrazolo[1,5-a]pyridin-4-yl)trimethylammonium

The nature of the counterion is not a determining factor regarding the dyeing power of the compounds of formula (III).

According to one embodiment, in formula (III) $Z_1$ and/or $Z_2$ represents a covalent bond, a radical —NR'$_6$(CH$_2$)$_q$— or a radical —O(CH$_2$)$_p$— and $R_1'$ and/or $R_2'$ is a cationic radical.

When $R_1'$ or $R_2'$ denotes a heterocycle, this heterocycle is preferably a cationic heterocycle or a heterocycle substituted with a cationic radical. By way of example, mention may be made of imidazoles substituted with a quaternary ammonium radical or imidazoliums, piperazines substituted with a quaternary ammonium radical or piperaziniums, pyrrolidines substituted with a quaternary ammonium radical or pyrrolidiniums, and diazepanes substituted with a quaternary ammonium radical or diazepaniums.

According to a different embodiment, $R_1'$ or $R_2'$ represents a group —N$^+$R$_{17}$R$_{18}$R$_{19}$, R$_{17}$, R$_{18}$ and R$_{19}$ being linear or branched $C_1$-$C_5$ alkyls optionally substituted with one or more hydroxyl groups, such as trialkylammonium, tri(hydroxyalkyl)ammonium, hydroxyalkyldialkylammonium or di(hydroxyalkyl)alkylammonium.

The radicals $R_3'$, $R_4'$ and $R_5'$, independently, may be a hydrogen atom or an optionally substituted $C_1$-$C_4$ alkyl radical. By way of example, mention may be made of methyl, ethyl, hydroxyethyl, aminoethyl, propyl and butyl radicals. According to one particular embodiment, $R_3'$, $R_4'$ and $R_5'$ independently represent a hydrogen atom or a $C_1$-$C_4$ alkyl radical.

According to one particular embodiment, $R_4'$ and $R_5'$ together form a partially saturated or unsaturated 5- or 8-membered ring, especially a cyclopentene or cyclohexene, which is optionally substituted.

According to one particular embodiment, the compound of formula (III) corresponds to formula (III') below:

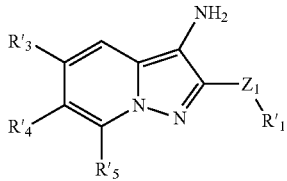

(III')

in which $Z_1$, $R_1'$, $R_3'$, $R_4'$ and $R_5'$ are as defined previously.

According to one particular embodiment of this formula, $Z_1$ represents a covalent bond, a radical —NR'$_6$(CH$_2$)$_q$— or a radical —O(CH$_2$)$_p$— and $R_1'$ is a cationic radical.

As cationic oxidation bases of formula (III), the following bases are most particularly preferred:

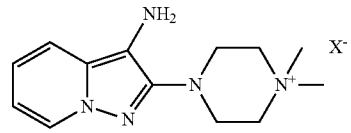

salt of 4-(3-aminopyrazolo[1,5-a]pyridin-2-yl)-1,1-dimethylpiperazin-1-ium

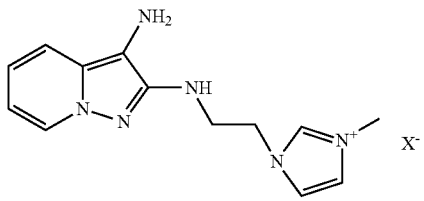

salt of 3-[2-(3-aminopyrazolo[1,5-a]pyridin-2-ylamino)ethyl]-1-methyl-3H-imidazol-1-ium and the addition salts thereof, solvates thereof and solvates of the salts thereof.

According to one particular embodiment of the invention, in formula (III), R"$_1$ represents a hydrogen atom or a saturated $C_1$-$C_4$ alkyl radical optionally substituted with a hydroxyl radical.

According to another particular embodiment, R"$_2$ and R"$_3$, which may be identical or different, represent a hydrogen atom, a $C_1$-$C_4$ alkyl radical optionally substituted with one or more hydroxyl radicals; a carboxyl radical; a $C_1$-$C_4$ alkyl carboxylate radical; a radical CONR"$_7$R"$_8$, preferably CONH$_2$. Preferably, R"$_2$ and R"$_3$, which may be identical or different, represent a hydrogen atom; a $C_1$-$C_4$ alkyl radical optionally substituted with one or more hydroxyl radicals.

According to another particular embodiment, R"$_4$ and R"$_5$ are identical and represent a hydrogen atom.

According to another particular embodiment, R"$_6$ represents a linear or branched $C_1$-$C_6$ alkyl radical; a carboxyl radical; a $C_1$-$C_6$ alkyl carboxylate; a carboxamide radical; a ($C_1$-$C_6$)alkoxy($C_1$-$C_6$)alkyloxy radical; a $C_1$-$C_6$ alkoxy or hydroxy($C_1$-$C_6$)alkyloxy radical; a radical O-Ak-NR"$_9$R"$_{10}$ with Ak=linear $C_1$-$C_6$ or branched $C_3$-$C_6$ divalent alkylene radical optionally interrupted with a radical NR"$_7$. Preferably, R"$_6$ represents a linear or branched $C_1$-$C_6$ alkyl radical; a ($C_1$-$C_6$)alkoxy($C_1$-$C_6$)alkyloxy radical; a $C_1$-$C_6$ alkoxy or hydroxy($C_1$-$C_6$)alkyloxy radical; a radical O-Ak-NR"$_9$R"$_{10}$ with Ak=linear $C_1$-$C_6$ or branched $C_3$-$C_6$ divalent alkylene radical optionally interrupted with a radical NR"$_7$.

More particularly, in formula (IV), the radicals $R_1$ and $R_2$, which may be identical or different, are chosen from:

a $C_1$-$C_6$ and preferably $C_1$-$C_4$ alkyl radical, optionally substituted with a hydroxyl, a ($C_1$-$C_2$)alkoxy, an amino or a (di)($C_1$-$C_2$)alkylamino;

a phenyl, methoxyphenyl, ethoxyphenyl or benzyl radical.

Preferably, the radicals $R_1$ and $R_2$, which may be identical or different, are chosen from methyl, ethyl, 2-hydroxyethyl, 3-hydroxypropyl, 2-hydroxypropyl and phenyl radicals.

According to another embodiment, the radicals $R_1$ and $R_2$ form, together with the nitrogen atoms to which they are attached, a saturated or unsaturated, 5- or 6-membered, optionally substituted ring.

Preferably, the radicals $R_1$ and $R_2$ form, together with the nitrogen atoms to which they are attached, a pyrazolidine or pyridazolidine ring, optionally substituted with one or more $C_1$-$C_4$ alkyl, hydroxyl, ($C_1$-$C_2$)alkoxy, carboxyl, carboxamido, amino or (di)($C_1$-$C_2$)alkylamino radicals.

Even more advantageously, the radicals $R_1$ and $R_2$ form, together with the nitrogen atoms to which they are attached, a pyrazolidine or pyridazolidine ring.

As regards the radicals $R_3$ and $R_4$, these radicals, which may be identical or different, are more particularly chosen from a hydrogen atom; a linear or branched $C_1$-$C_6$ and preferably $C_1$-$C_4$ alkyl radical, optionally substituted with one or more hydroxyl, ($C_1$-$C_2$)alkoxy, amino or (di)($C_1$-$C_2$)alkylamino; a phenyl radical optionally substituted with one or more hydroxyl, amino or ($C_1$-$C_2$)alkoxy radicals.

Preferably, the radicals $R_3$ and $R_4$, which may be identical or different, are chosen from a hydrogen atom and methyl, ethyl, isopropyl, 2-hydroxyethyl, 3-hydroxypropyl, 2-hydroxypropyl and 2-carboxyethyl radicals. According to one particular embodiment, the radicals $R'_3$ and $R'_4$ represent a hydrogen atom.

According to another embodiment, the radicals $R_3$ and $R_4$ form, together with the nitrogen atom to which they are attached, a 5- or 7-membered ring chosen from pyrrolidine, piperidine, homopiperidine, piperazine and homopiperazine heterocycles; the said rings possibly being substituted with one or more hydroxyl, amino, (di)($C_1$-$C_2$)alkylamino, carboxyl, carboxamido or $C_1$-$C_4$ alkyl radicals optionally substituted with one or more hydroxyl, amino or $C_1$-$C_2$ (di) alkylamino radicals.

More particularly, the radicals $R_3$ and $R_4$ form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethyl piperidine, 3-hydroxypiperidine, 4-hydroxypiperidine, 3-hydroxymethylpiperi dine, homopiperidine, 2-carboxyhomopiperidine, 2-carboxamidohomopiperidine, homopiperazine, N-methylhomopiperazine and N-(2-hydroxyethyl)homopiperazine.

Preferably, the radicals $R_3$ and $R_4$ form, together with the nitrogen atom to which they are attached, a 5- or 7-membered ring chosen from pyrrolidine, 3-hydroxypyrrolidine, 3-aminopyrrolidine, 3-dimethylaminopyrrolidine, pyrrolidine-2-carboxylicacid, 3-hydroxypyrrolidine-2-carboxylic acid, piperidine, hydroxypiperidine, homopiperidine, 1,4-diazepane, N-methylhomopiperazine and N-β-hydroxyethylhomopiperazine.

In accordance with an even more preferred embodiment of the invention, the radicals $R_3$ and $R_4$ form, together with the nitrogen atom to which they are attached, a 5-membered ring such as pyrrolidine, 3-hydroxypyrrolidine, 3-aminopyrrolidine or 3-dimethylaminopyrrolidine.

As examples of derivatives of formula (IV), mention may be made of the compounds presented below, or the addition salts thereof, solvates thereof or solvates of the salts thereof:
4,5-diamino-1,2-dimethyl-1,2-dihydropyrazol-3-one;
4-amino-5-methylamino-1,2-dimethyl-1,2-dihydropyrazol-3-one;
4-amino-5-dimethylamino-1,2-dimethyl-1,2-dihydropyrazol-3-one;
4-amino-5-(2-hydroxyethyl)amino-1,2-dimethyl-1,2-dihydropyrazol-3-one;
4-amino-5-(pyrrolidin-1-yl)-1,2-dimethyl-1,2-dihydropyrazol-3-one;
4-amino-5-(piperidin-1-yl)-1,2-dimethyl-1,2-dihydropyrazol-3-one;
4,5-diamino-1,2-bis(2-hydroxyethyl)-1,2-dihydropyrazol-3-one;
4-amino-5-methylamino-1,2-bis(2-hydroxyethyl)-1,2-dihydropyrazol-3-one;
4-amino-5-dimethylamino-1,2-bis(2-hydroxyethyl)-1,2-dihydropyrazol-3-one;
4-amino-5-(2-hydroxyethyl)amino-1,2-bis(2-hydroxyethyl)-1,2-dihydropyrazol-3-one;
4-amino-5-(pyrrolidin-1-yl)-1,2-bis(2-hydroxyethyl)-1,2-dihydropyrazol-3-one;
4-amino-5-(piperidin-1-yl)-1,2-bis(2-hydroxyethyl)-1,2-dihydropyrazol-3-one;
4,5-diamino-1,2-diethyl-1,2-dihydropyrazol-3-one;
4,5-diamino-1,2-phenyl-1,2-dihydropyrazol-3-one;
4,5-diamino-1-ethyl-2-methyl-1,2-dihydropyrazol-3-one;
4,5-diamino-2-ethyl-1-methyl-1,2-dihydropyrazol-3-one;
4,5-diamino-1-phenyl-2-methyl-1,2-dihydropyrazol-3-one;
4,5-diamino-2-phenyl-1-methyl-1,2-dihydropyrazol-3-one;
4,5-diamino-1-(2-hydroxyethyl)-2-methyl-1,2-dihydropyrazol-3-one;
4,5-diamino-2-(2-hydroxyethyl)-1-methyl-1,2-dihydropyrazol-3-one;
2,3-diamino-6,7-dihydro-1H,5H-pyrazolo[1,2-a]pyrazol-1-one;
2-amino-3-methylamino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(2-hydroxyethyl)amino-6,7-dihydro-1H,5H-pyrazolo[1,2-a]pyrazol-1-one;
2-amino-3-(2-hydroxypropyl)amino-6,7-dihydro-1H,5H-pyrazolo[1,2-a]pyrazol-1-one;
2-amino-3-bis(2-hydroxyethyl)amino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
2-amino-3-(3-hydroxypyrrolidin-1-yl)-6,7-dihydro-1H,5H-pyrazolo[1,2-a]pyrazol-1-one;
2-amino-3-(piperidin-1-yl)-6,7-dihydro-1H,5H-pyrazolo[1,2-a]pyrazol-1-one;
2,3-diamino-6-hydroxy-6,7-dihydro-1H,5H-pyrazolo[1,2-a]pyrazol-1-one;
2,3-diamino-6-methyl-6,7-dihydro-1H,5H-pyrazolo[1,2-a]pyrazol-1-one;
2,3-diamino-6-dimethyl-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
2,3-diamino-5,8-dihydro-1H,6H-pyridazino[1,2-a]pyrazol-1-one;
4-amino-5-dimethylamino-1,2-diethyl-1,2-dihydropyrazol-3-one;
4-amino-1,2-diethyl-5-ethylamino-1,2-dihydropyrazol-3-one;

4-amino-1,2-diethyl-5-isopropylamino-1,2-dihydropyrazol-3-one;

4-amino-1,2-diethyl-5-(2-hydroxyethylamino)-1,2-dihydropyrazol-3-one;

4-amino-5-(2-dimethylaminoethylamino)-1,2-diethyl-1,2-dihydropyrazol-3-one;

4-amino-5-[bis(2-hydroxyethyl)amino]-1,2-diethyl-1,2-dihydropyrazol-3-one;

4-amino-1,2-diethyl-5-(3-imidazol-1-ylpropylamino)-1,2-dihydropyrazol-3-one;

4-amino-5-dimethylamino-1,2-diethyl-1,2-dihydropyrazol-3-one;

4-amino-1,2-diethyl-5-ethylamino-1,2-dihydropyrazol-3-one;

4-amino-1,2-diethyl-5-isopropylamino-1,2-dihydropyrazol-3-one;

4-amino-1,2-diethyl-5-(2-hydroxyethylamino)-1,2-dihydropyrazol-3-one;

4-amino-5-(2-dimethylaminoethylamino)-1,2-diethyl-1,2-dihydropyrazol-3-one;

4-amino-5-[bis(2-hydroxyethyl)amino]-1,2-diethyl-1,2-dihydropyrazol-3-one;

4-amino-1,2-diethyl-5-(3-imidazol-1-ylpropylamino)-1,2-dihydropyrazol-3-one;

4-amino-1,2-diethyl-5-(3-hydroxypyrrolidin-1-yl)-1,2-dihydropyrazol-3-one;

4-amino-1,2-diethyl-5-pyrrolidin-1-yl-1,2-dihydropyrazol-3-one;

4-amino-5-(3-dimethylaminopyrrolidin-1-yl)-1,2-diethyl-1,2-dihydropyrazol-3-one;

4-amino-1,2-diethyl-5-(4-methylpiperazin-1-yl)pyrazolidin-3-one;

2,3-diamino-6-hydroxy-6,7-dihydro-5H-pyrazolo[1,2-a]pyrazol-1-one;

some of which are featured below to illustrate the names via chemical structures:

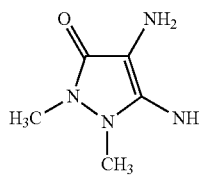

4,5-Diamino-1,2-dimethyl-1,2-dihydropyrazol-3-one

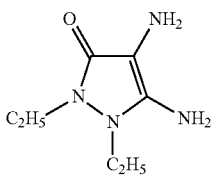

4,5-Diamino-1,2-diethyl-1,2-dihydro-pyrazol-3-one 4,5-Diamino-1,2-diphenyl-1,2-dihydropyrazol-3-one 4,5-Diamino-1-ethyl-2-methyl-1,2-dihydropyrazol-3-one

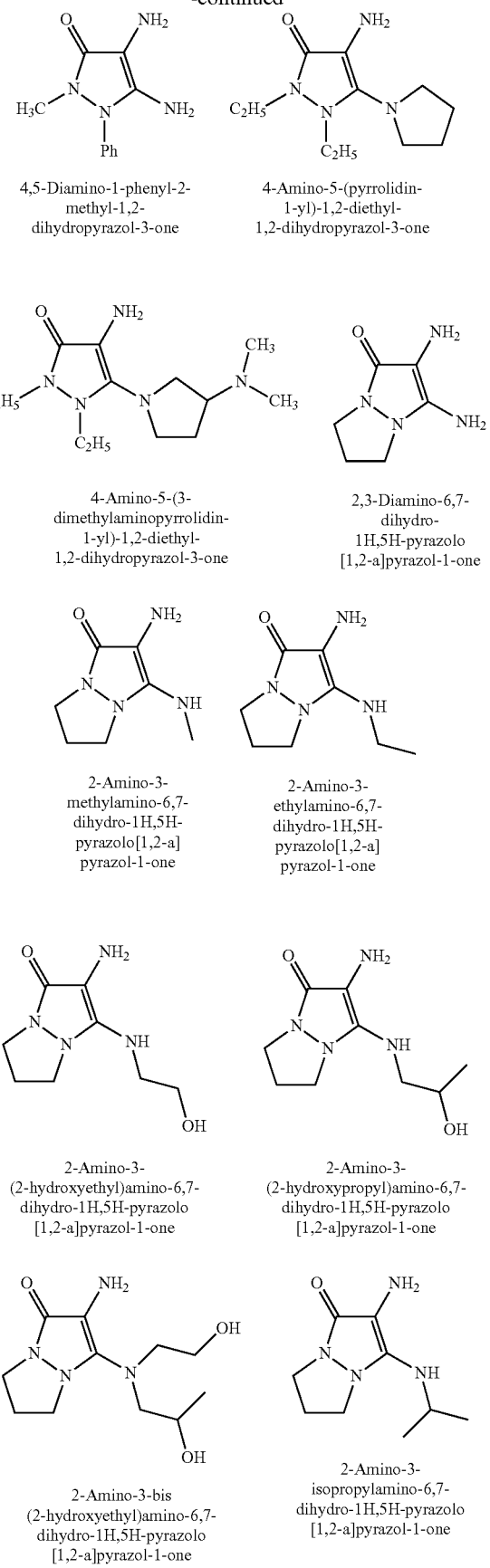

4,5-Diamino-1-phenyl-2-methyl-1,2-dihydropyrazol-3-one

4-Amino-5-(pyrrolidin-1-yl)-1,2-diethyl-1,2-dihydropyrazol-3-one

4-Amino-5-(3-dimethylaminopyrrolidin-1-yl)-1,2-diethyl-1,2-dihydropyrazol-3-one 2,3-Diamino-6,7-dihydro-1H,5H-pyrazolo[1,2-a]pyrazol-1-one 2-Amino-3-methylamino-6,7-dihydro-1H,5H-pyrazolo[1,2-a]pyrazol-1-one 2-Amino-3-ethylamino-6,7-dihydro-1H,5H-pyrazolo[1,2-a]pyrazol-1-one 2-Amino-3-(2-hydroxyethyl)amino-6,7-dihydro-1H,5H-pyrazolo[1,2-a]pyrazol-1-one 2-Amino-3-(2-hydroxypropyl)amino-6,7-dihydro-1H,5H-pyrazolo[1,2-a]pyrazol-1-one 2-Amino-3-bis(2-hydroxyethyl)amino-6,7-dihydro-1H,5H-pyrazolo[1,2-a]pyrazol-1-one 2-Amino-3-isopropylamino-6,7-dihydro-1H,5H-pyrazolo[1,2-a]pyrazol-1-one

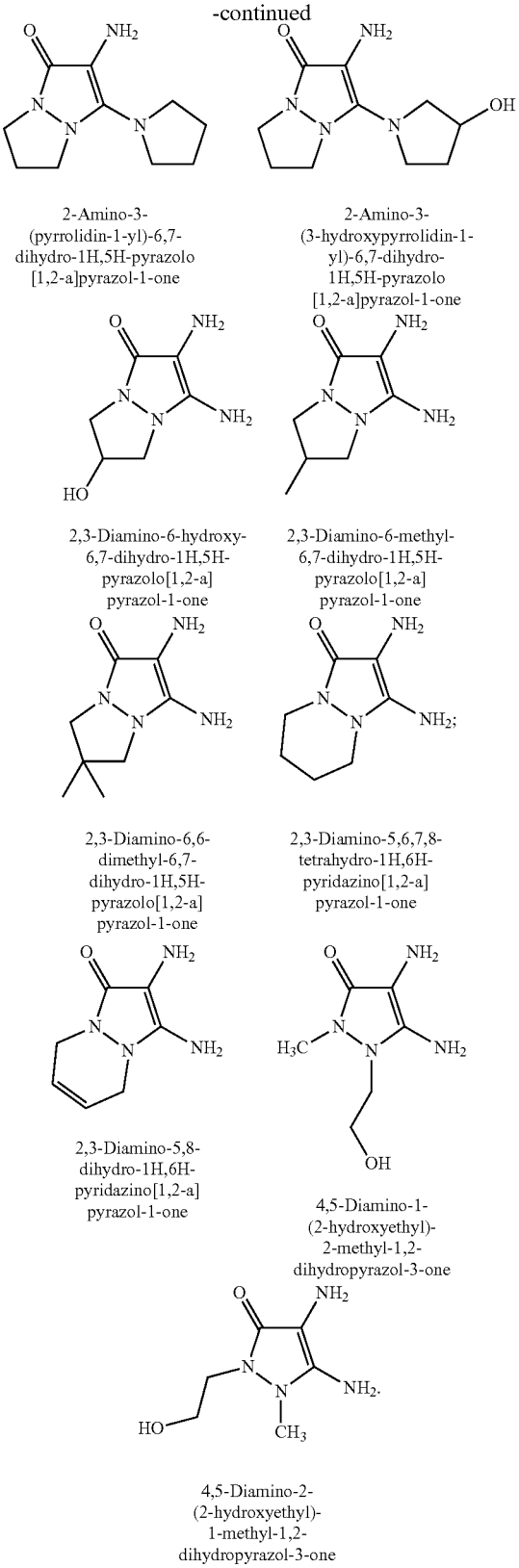

Among these compounds, the diamino-N,N-dihydropyrazolone derivatives of formula (IV) or the addition salts thereof, solvates thereof and solvates of the salts thereof that are particularly preferred are:

2,3-diamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
4,5-diamino-1,2-dimethyl-1,2-dihydropyrazol-3-one;
4,5-diamino-1,2-diethyl-1,2-dihydropyrazol-3-one;
4,5-diamino-1,2-bis(2-hydroxyethyl)-1,2-dihydropyrazol-3-one;
2-amino-3-(2-hydroxyethyl)amino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
4-amino-1,2-diethyl-5-(pyrrolidin-1-yl)-1,2-dihydropyrazol-3-one;
4-amino-5-(3-dimethylaminopyrrolidin-1-yl)-1,2-diethyl-1,2-dihydropyrazol-3-one;
2,3-diamino-6-hydroxy-6,7-dihydro-1H,5H-pyrazolo[1,2-a]pyrazol-1-one.

According to one particular embodiment, the composition of the invention contains an oxidation base chosen from:
4,5-diamino-1,2-diethyl-1,2-dihydropyrazol-3-one;
4-amino-1,2-diethyl-5-(pyrrolidin-1-yl)-1,2-dihydropyrazol-3-one;
4-amino-5-(3-dimethylaminopyrrolidin-1-yl)-1,2-diethyl-1,2-dihydropyrazol-3-one;
2,3-diamino-6-hydroxy-6,7-dihydro-1H,5H-pyrazolo[1,2-a]pyrazol-1-one;
2,3-diamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
and the addition salts thereof, solvates thereof and solvates of the salts thereof.

According to one particular embodiment of the invention, in formula (V), $R'_1$, represents a hydrogen atom or a saturated $C_1$-$C_4$ alkyl radical optionally substituted with a hydroxyl radical.

According to another particular embodiment, $R'_2$ and $R'_3$, which may be identical or different, represent a hydrogen atom, a $C_1$-$C_4$ alkyl radical optionally substituted with one or more hydroxyl radicals; a carboxyl radical; a $C_1$-$C_4$ alkyl carboxylate radical; a radical $CONR'_7R'_6$, preferably $CONH_2$. Preferably, $R'_2$ and $R'_3$, which may be identical or different, represent a hydrogen atom; a $C_1$-$C_4$ alkyl radical optionally substituted with one or more hydroxyl radicals.

According to another particular embodiment, $R'_4$ and $R'_5$ are identical and represent a hydrogen atom.

According to another particular embodiment, $R'_6$ represents a linear or branched $C_1$-$C_6$ alkyl radical; a carboxyl radical; a $C_1$-$C_6$ alkyl carboxylate; a carboxamide radical; a $(C_1$-$C_6)$alkoxy$(C_1$-$C_6)$alkyloxy radical; a $C_1$-$C_6$ alkoxy or hydroxy$(C_1$-$C_6)$alkyloxy radical; a radical O-Ak-$NR'_9R'_{10}$ with Ak=linear $C_1$-$C_6$ or branched $C_3$-$C_6$ divalent alkylene radical optionally interrupted with a radical $NR'_7$. Preferably, $R'_6$ represents a linear or branched $C_1$-$C_6$ alkyl radical; a $(C_1$-$C_6)$alkoxy$(C_1$-$C_6)$alkyloxy radical; a $C_1$-$C_6$ alkoxy or hydroxy$(C_1$-$C_6)$alkyloxy radical; a radical O-Ak-$NR'_9R'_{10}$ with Ak=linear $C_1$-$C_6$ or branched $C_3$-$C_6$ divalent alkylene radical optionally interrupted with a radical $NR'_7$.

According to one particular embodiment, the compounds in accordance with the invention are chosen from the 4-aminoindole derivatives of formula (II'), and also the addition salts thereof, solvates thereof and solvates of the salts thereof:

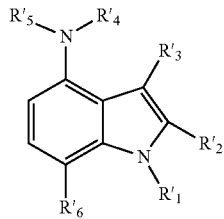

(II')

in which:

R'$_1$ represents:
- a hydrogen atom;
- a saturated C$_1$-C$_4$ alkyl radical optionally substituted with a hydroxyl radical;

R'$_2$ and R'$_3$, which may be identical or different, represent:
- a hydrogen atom;
- a C$_1$-C$_4$ alkyl radical optionally substituted with one or more hydroxyl radicals, preferably optionally substituted with a hydroxyl radical;
- a carboxyl radical;
- a C$_1$-C$_4$ alkyl carboxylate radical;
- a radical CONR'$_7$R'$_8$, preferably a carboxamide radical CONH$_2$;

R'$_4$ and R'$_5$ represent a hydrogen atom;

R'$_6$ represents:
- a linear or branched C$_1$-C$_6$ alkyl radical;
- a carboxyl radical;
- a C$_1$-C$_6$ alkyl carboxylate;
- a carboxamide radical;
- a (C$_1$-C$_6$)alkoxy(C$_1$-C$_6$)alkyloxy radical;
- a C$_1$-C$_6$ alkoxy radical or a C$_1$-C$_6$ hydroxyalkyloxy radical;
- a radical O-Ak-NR'$_9$R'$_{10}$ with Ak=linear C$_1$-C$_6$ or branched C$_3$-C$_6$ divalent alkylene radical, optionally interrupted with a radical NR'$_7$;

R'$_7$ and R'$_8$ represent a hydrogen atom or a C$_1$-C$_6$ alkyl radical optionally substituted with a hydroxyl radical;

R'$_9$ and R'$_{10}$, which may be identical or different, represent a saturated linear C$_1$-C$_4$ alkyl radical or an unsaturated linear C$_2$-C$_4$ alkyl radical;

R'$_9$ and R'$_{10}$ may form, with the nitrogen that bears them, a saturated or unsaturated 5- to 8-membered heterocycle, one of the chain members possibly being an oxygen atom or a radical NR'$_{11}$ with R'$_{11}$=H or C$_1$-C$_4$ alkyl, optionally substituted with OH.

The derivatives of formula (II) may optionally be salified with strong mineral acids, for instance HCl, HBr, HI, H$_2$SO$_4$ or H$_3$PO$_4$, or organic acids, for instance acetic acid, lactic acid, tartaric acid, citric acid, succinic acid, benzenesulfonic acid, para-toluenesulfonic acid, formic acid or methanesulfonic acid.

The derivatives of formula (II) may also be in the form of solvates, for example a hydrate or a solvate of a linear or branched alcohol such as ethanol or isopropanol.

As examples of derivatives of formula (II), mention may be made of the compounds presented below:

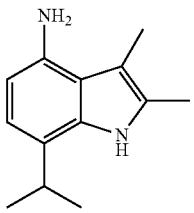

2,3-dimethyl-7-(propan-2-yl)-1H-indol-4-amine 7-ethyl-2,3-dimethyl-1H-indol-4-amine

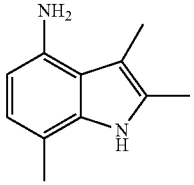

2,3,7-trimethyl-1H-indol-4-amine 3-ethyl-2,7-dimethyl-1H-indol-4-amine

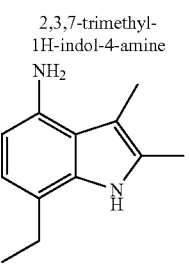

7-ethyl-2,3-dimethyl-1H-indol-4-amine 3,7-diethyl-2-methyl-1H-indol-4-amine

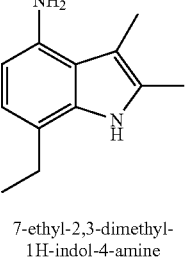

2,3-dimethyl-7-(propan-2-yl)-1H-indol-4-amine 3-ethyl-2-methyl-7-(propan-2-yl)-1H-indol-4-amine

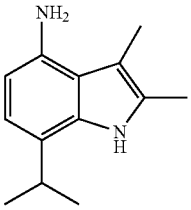

7-ethyl-1,2,3-trimethyl-1H-indol-4-amine 3,7-diethyl-1,2-dimethyl-1H-indol-4-amine

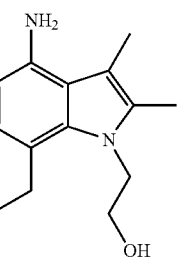
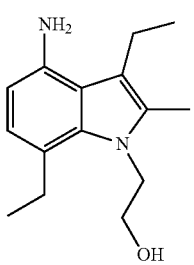

2-(4-amino-7-ethyl-2,3-dimethyl-1H-indol-1-yl)ethanol 2-(4-amino-3,7-diethyl-2-methyl-1H-indol-1-yl)ethanol -continued

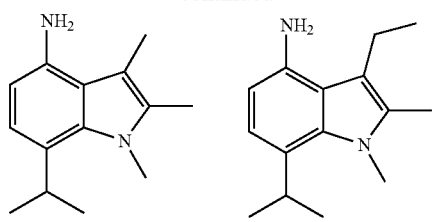

1,2,3-trimethyl-7-
(propan-2-yl)-
1H-indol-4-amine 3-ethyl-1,2-dimethyl-
7-(propan-2-yl)-
1H-indol-4-amine

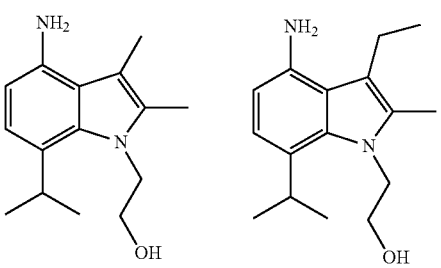

2-[4-amino-2,3-
dimethyl-7-(propan-
2-yl)-1H-indol-
1-yl]ethanol

2-[4-amino-3-ethyl-
2-methyl-7-(propan-
2-yl)-1H-indol-
1-yl]ethanol

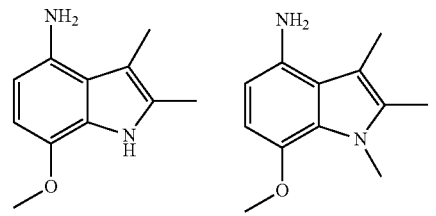

7-methoxy-2,3-
dimethyl-1H-
indol-4-amine 7-methoxy-1,2,3-
trimethyl-1H-
indol-4-amine

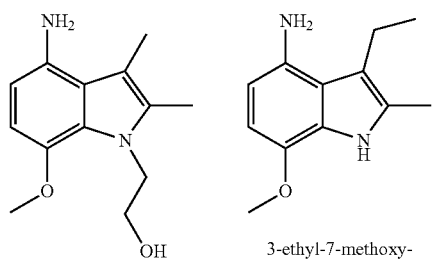

2-(4-amino-
7-methoxy-2,3-
dimethyl-1H-
indol-1-yl)ethanol 3-ethyl-7-methoxy-
2-methyl-1H-
indol-4-amine

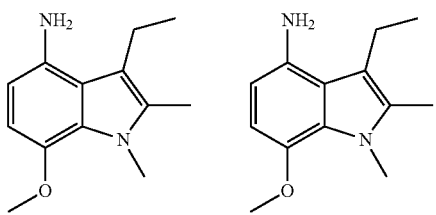

3-ethyl-7-methoxy-
1,2-dimethyl-1H-
indol-4-amine 3-ethyl-7-methoxy-
1,2-dimethyl-1H-
indol-4-amine -continued

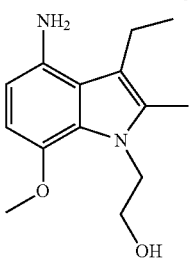

2-(4-amino-3-ethyl-7-
methoxy-2-methyl-1H-
indol-1-yl)ethanol 7-ethoxy-2,3-dimethyl-
1H-indol-4-amine

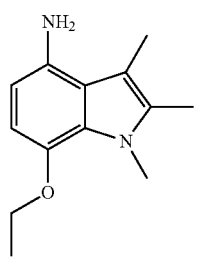

7-ethoxy-1,2,3-trimethyl-
1H-indol-4-amine 12-(4-amino-
7-ethoxy-2,3-dimethyl-
1H-indol-1-yl)ethanol

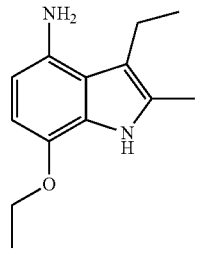

7-ethoxy-3-ethyl-2-
methyl-1H-indol-
4-amine 7-ethoxy-3-ethyl-1,2-
dimethyl-1H-indol-
4-amine

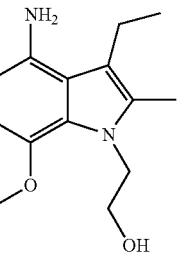

2-(4-amino-
7-ethoxy-3-ethyl-2-
methyl-1H-indol-1-
yl)ethanol

2-[(4-amino-2,3-
dimethyl-1H-indol-
7-yl)oxy]ethanol

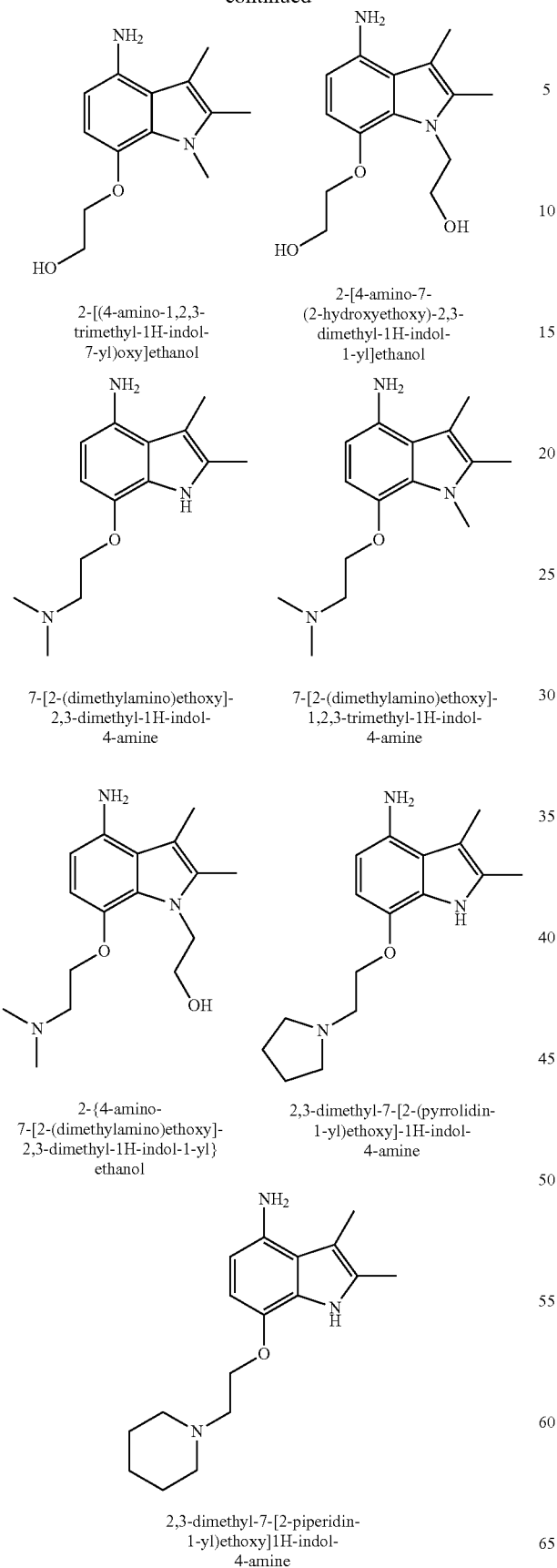
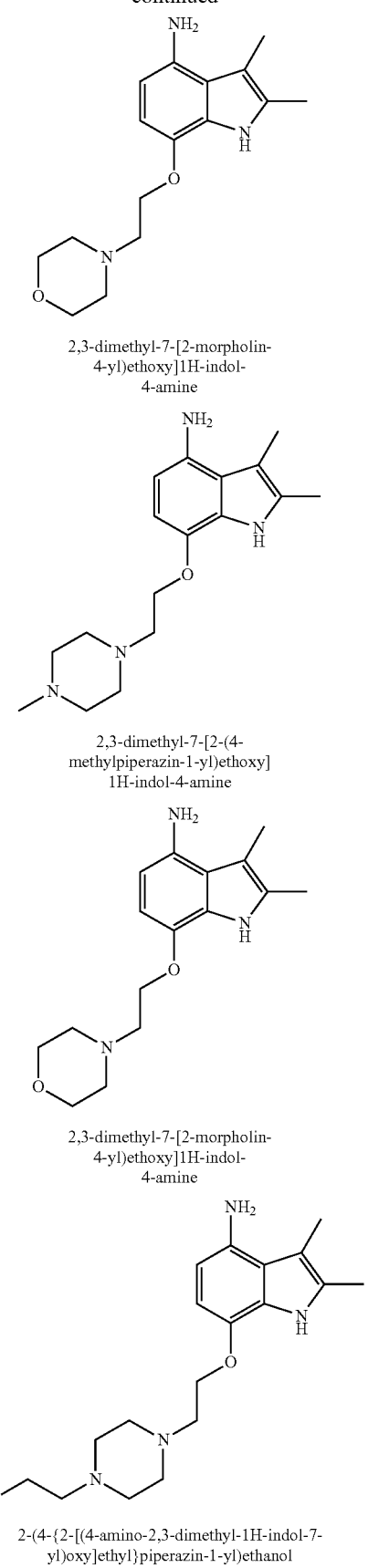

-continued

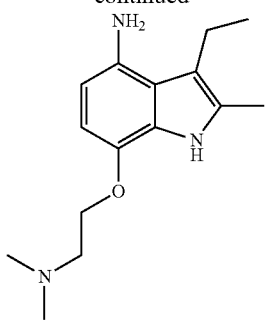

7-[2-(dimethylamino-
ethoxy]-3-ethyl-2-methyl
1H-indol-4-amine

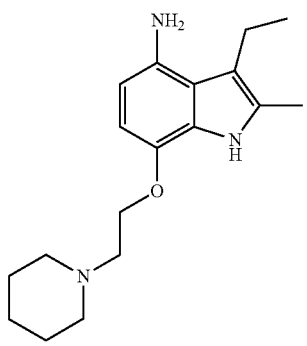

3-ethyl-2-methyl-7-[2-(piperidin-
1-yl)ethoxy]-1H-indol-4-amine

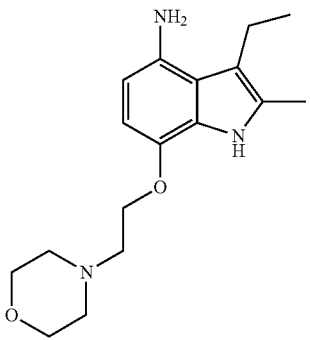

3-ethyl-2-methyl-7-[2-(morpholin-
4-yl)ethoxy]-1H-indol-4-amine

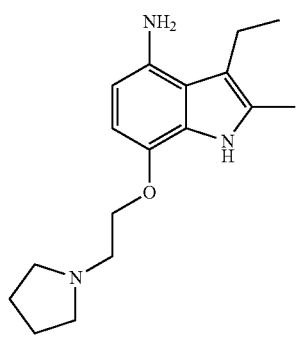

3-ethyl-2-methyl-7-[2-(pyrrolidin-
1-yl)ethoxy]-1H-indol-4-amine

-continued

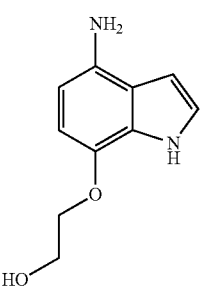

2-[(4-amino-1H-indol-
7-yl)oxy]ethanol

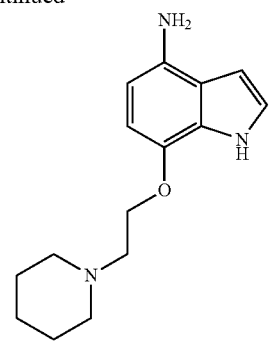

7-[2-(piperidin-1-yl)ethoxy]-
1H-indol-4-amine

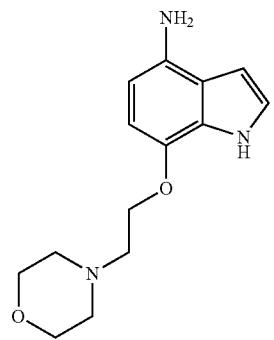

7-[2-(morpholin-4-yl)ethoxy]-
1H-indol-4-amine

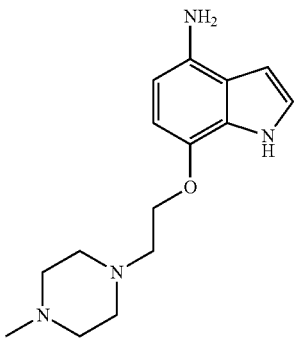

7-[2-(4-methylpiperazin-1-yl)ethoxy]-
1H-indol-4-amine

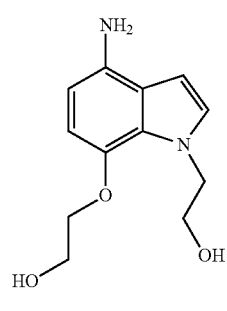

2-[4-amino-7-(2-
hydroxyethoxy)-
1H-indol-1-yl]ethanol

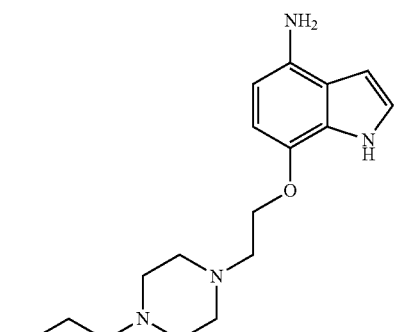

2-(4-{2-[(4-amino-1H-indol-7-
yl)oxy]ethyl}piperazin-1-yl)ethanol

-continued

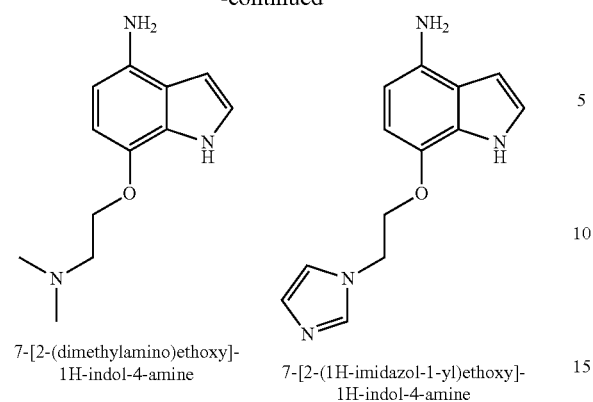

7-[2-(dimethylamino)ethoxy]-
1H-indol-4-amine

7-[2-(1H-imidazol-1-yl)ethoxy]-
1H-indol-4-amine

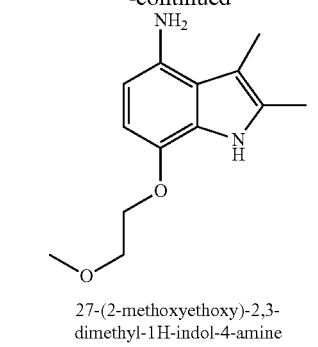

27-(2-methoxyethoxy)-2,3-
dimethyl-1H-indol-4-amine

7-[2-(1H-imidazol-1-yl)ethoxy]-
2,3-dimethyl
1H-indol-4-amine

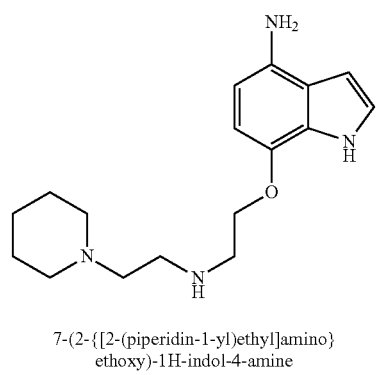

7-(2-{[2-(piperidin-1-yl)ethyl]amino}
ethoxy)-1H-indol-4-amine

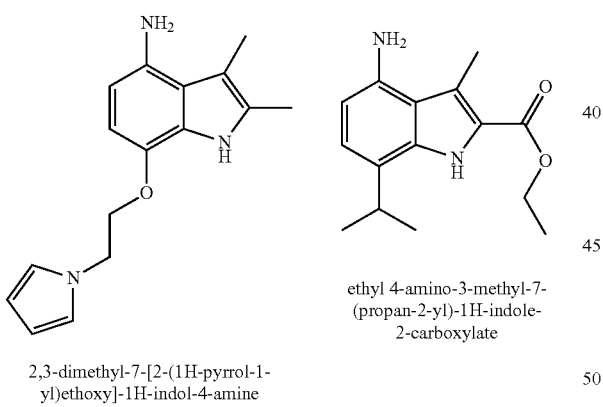

2,3-dimethyl-7-[2-(1H-pyrrol-1-
yl)ethoxy]-1H-indol-4-amine ethyl 4-amino-3-methyl-7-
(propan-2-yl)-1H-indole-
2-carboxylate

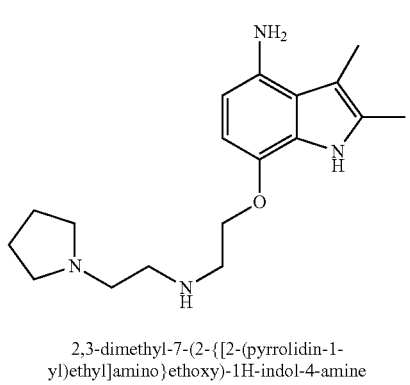

2,3-dimethyl-7-(2-{[2-(pyrrolidin-1-
yl)ethyl]amino}ethoxy)-1H-indol-4-amine 4-amino-7-
(propan-2-yl)-1H-indole-
2-carboxylic acid 7-(2-methoxyethoxy)-
1H-indol-4-amine

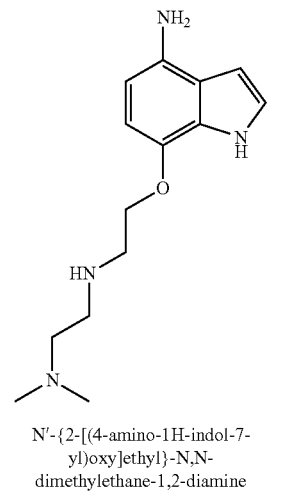

N'-{2-[(4-amino-1H-indol-7-
yl)oxy]ethyl}-N,N-
dimethylethane-1,2-diamine

-continued

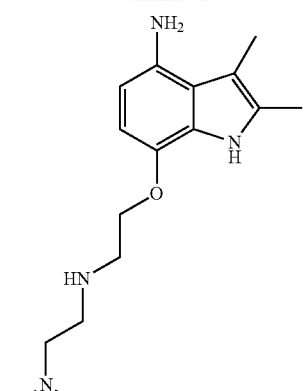

N'-{2-[(4-amino-2,3-dimethyl-1H-indol-7-yl)oxy]ethyl}-N,N-dimethylethane-1,2-diamine

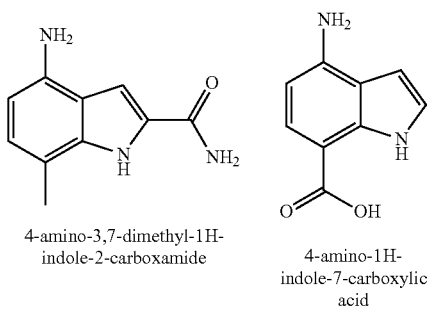

4-amino-3,7-dimethyl-1H-indole-2-carboxamide 4-amino-1H-indole-7-carboxylic acid

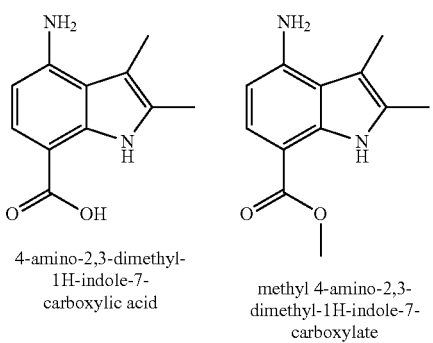

4-amino-2,3-dimethyl-1H-indole-7-carboxylic acid methyl 4-amino-2,3-dimethyl-1H-indole-7-carboxylate

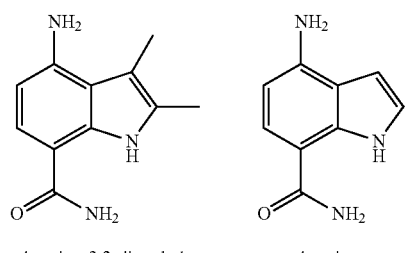

4-amino-2,3-dimethyl-1H-indole-7-carboxamide 4-amino-1H-indole-7-carboxamide

-continued

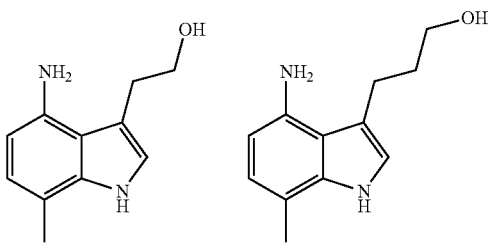

2-(4-amino-7-methyl-1H-indol-3-yl)ethanol 3-(4-amino-7-methyl-1H-indol-3-yl)propan-1-ol

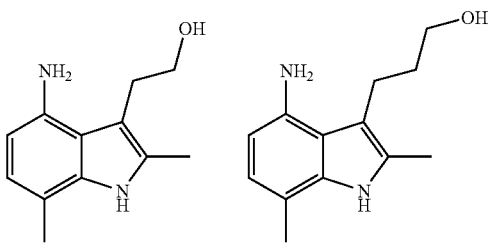

2-(4-amino-2,7-dimethyl-1H-indol-3-yl)ethanol 3-(4-amino-2,7-dimethyl-1H-indol-3-yl)propan-1-ol

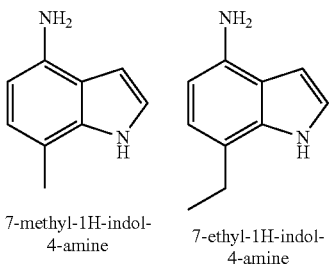

7-methyl-1H-indol-4-amine 7-ethyl-1H-indol-4-amine

Among these compounds, the derivatives of formula (II) that are particularly preferred are the following:

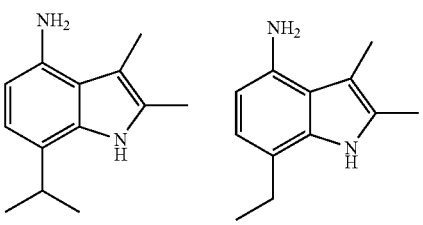

2,3-dimethyl-7-(propan-2yl)-1H-indol-4-amine 7-ethyl-2,3-dimethyl-1H-indol-4-amine

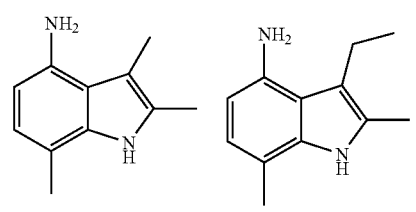

2,3,7-trimethyl-1H-indol-4-amine 3-ethyl-2,7-dimethyl-1H-indol-4-amine

-continued

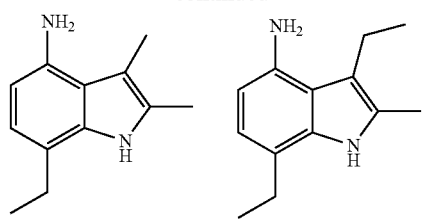

7-ethyl-2,3-dimethyl-1H-indol-4-amine 3,7-diethyl-2-methyl-1H-indol-4-amine

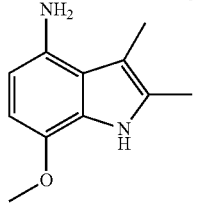

7-methoxy-2,3-dimethyl-1H-indol-4-amine

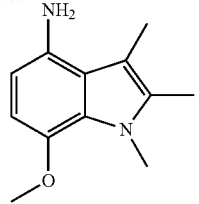

7-methoxy-1,2,3-trimethyl-1H-indol-4-amine

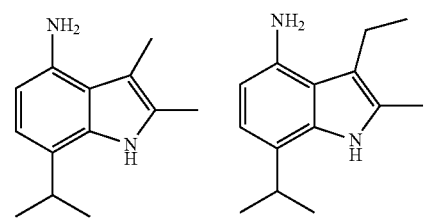

2,3-dimethyl-7-(propan-2-yl)-1H-indol-4-amine 3-ethyl-2-methyl-7-(propan-2-yl)-1H-indol-4-amine

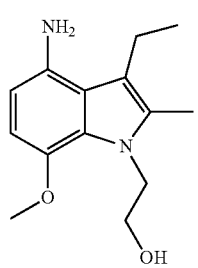

2-(4-amino-3-ethyl-7-methoxy-2-methyl-1H-indol-1-yl)ethanol

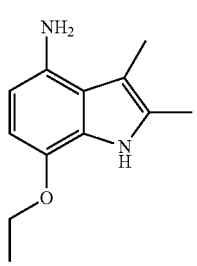

7-ethoxy-2,3-dimethyl-1H-indol-4-amine

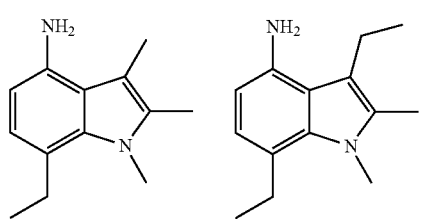

7-ethyl-1,2,3-trimethyl-1H-indol-4-amine 3,7-diethyl-1,2-dimethyl-1H-indol-4-amine

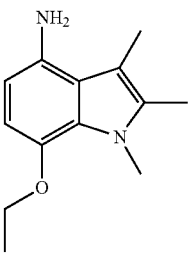

7-ethoxy-1,2,3-trimethyl-1H-indol-4-amine

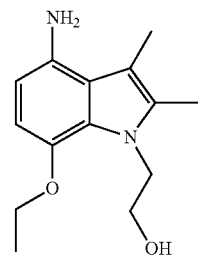

12-(4-amino-7-ethoxy-2,3-dimethyl-1H-indol-1-yl)ethanol

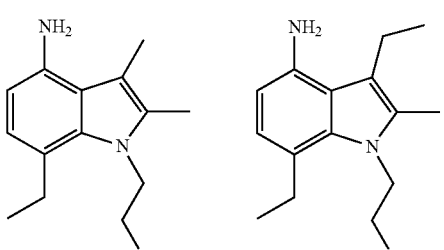

2-(4-amino-7-ethyl-2,3-dimethyl-1H-indol-1-yl)ethanol 2-(4-amino-3,7-diethyl-2-methyl-1H-indol-1-yl)ethanol

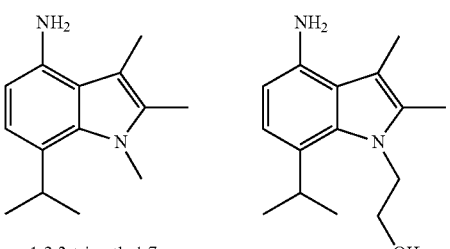

1,2,3-trimethyl-7-(propan-2-yl)-1H-indol-4-amine

2-[4-amino-2,3-dimethyl-7-(propan-2-yl)-1H-indol-1-yl]ethanol

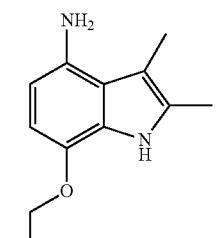

2-[(4-amino-2,3-dimethyl-1H-indol-7-yl)oxy]ethanol

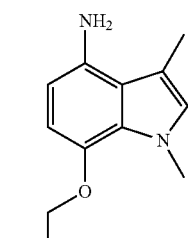

2-[(4-amino-1,2,3-trimethyl-1H-indol-7-yl)oxy]ethanol

-continued

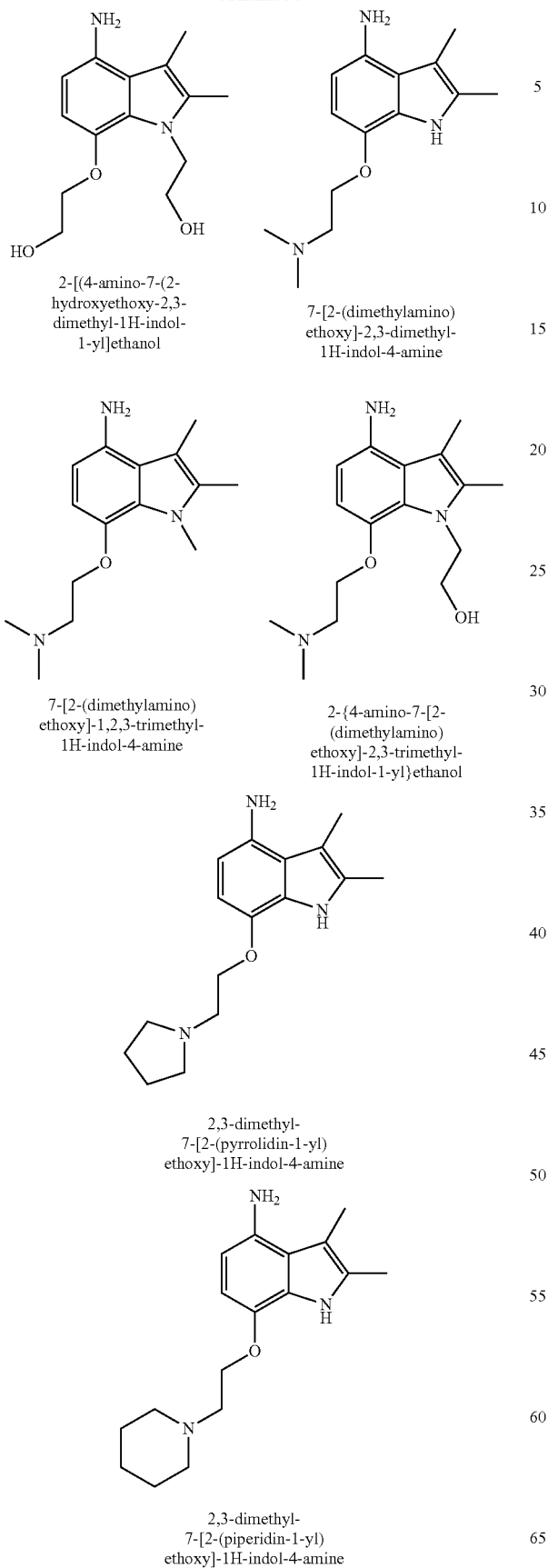

2-[(4-amino-7-(2-hydroxyethoxy-2,3-dimethyl-1H-indol-1-yl]ethanol

7-[2-(dimethylamino)ethoxy]-2,3-dimethyl-1H-indol-4-amine

7-[2-(dimethylamino)ethoxy]-1,2,3-trimethyl-1H-indol-4-amine

2-{4-amino-7-[2-(dimethylamino)ethoxy]-2,3-trimethyl-1H-indol-1-yl}ethanol 2,3-dimethyl-7-[2-(pyrrolidin-1-yl)ethoxy]-1H-indol-4-amine 2,3-dimethyl-7-[2-(piperidin-1-yl)ethoxy]-1H-indol-4-amine -continued

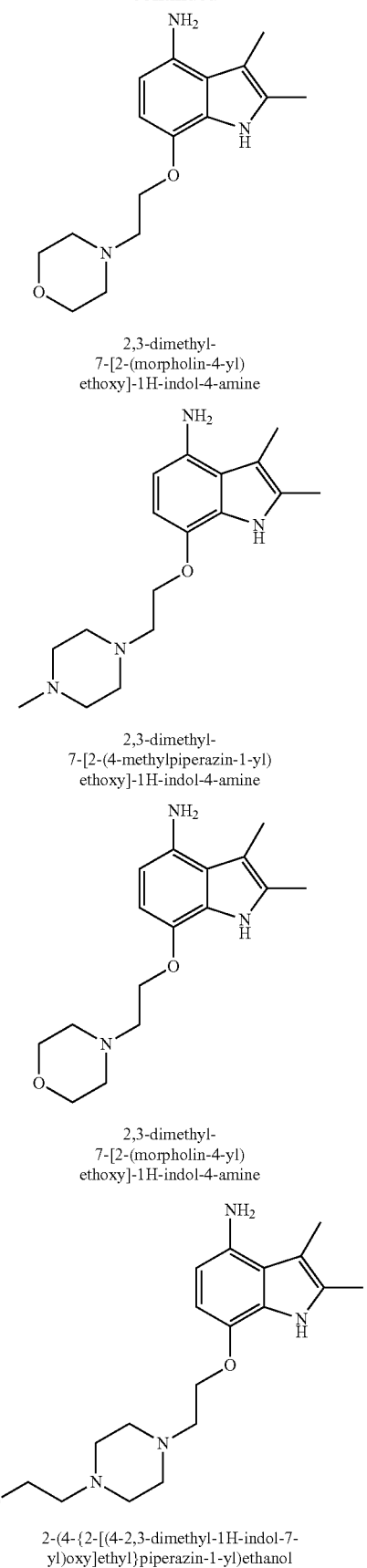

2,3-dimethyl-7-[2-(morpholin-4-yl)ethoxy]-1H-indol-4-amine 2,3-dimethyl-7-[2-(4-methylpiperazin-1-yl)ethoxy]-1H-indol-4-amine 2,3-dimethyl-7-[2-(morpholin-4-yl)ethoxy]-1H-indol-4-amine 2-(4-{2-[(4-2,3-dimethyl-1H-indol-7-yl)oxy]ethyl}piperazin-1-yl)ethanol

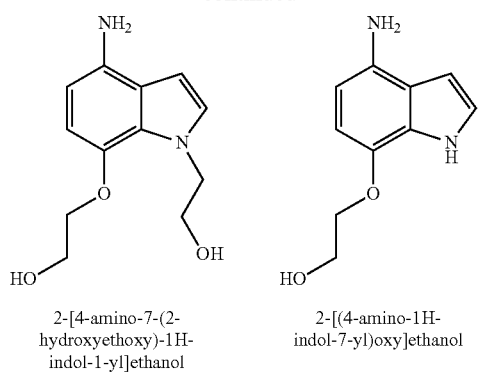

2-[4-amino-7-(2-hydroxyethoxy)-1H-indol-1-yl]ethanol

2-[(4-amino-1H-indol-7-yl)oxy]ethanol

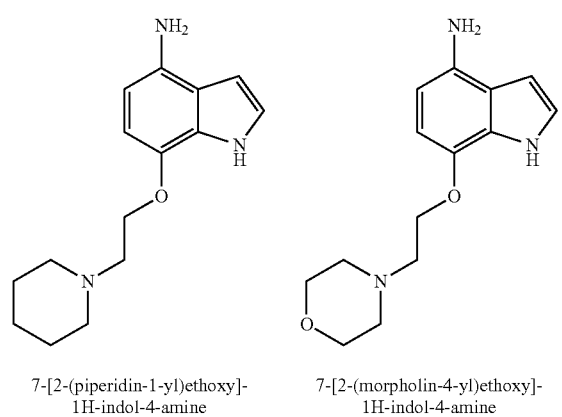

7-[2-(piperidin-1-yl)ethoxy]-1H-indol-4-amine

7-[2-(morpholin-4-yl)ethoxy]-1H-indol-4-amine

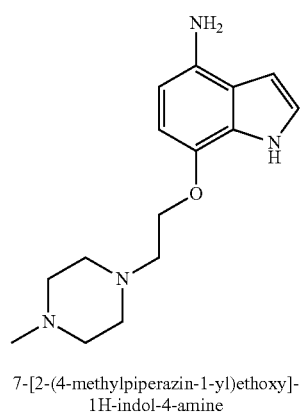

7-[2-(4-methylpiperazin-1-yl)ethoxy]-1H-indol-4-amine

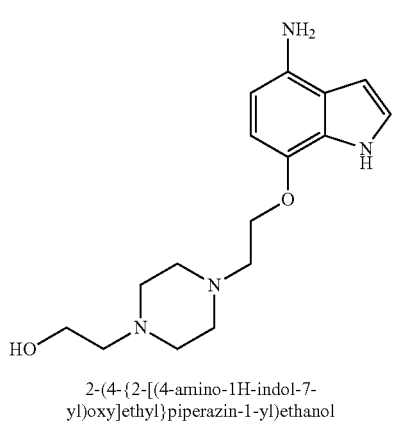

2-(4-{2-[(4-amino-1H-indol-7-yl)oxy]ethyl}piperazin-1-yl)ethanol

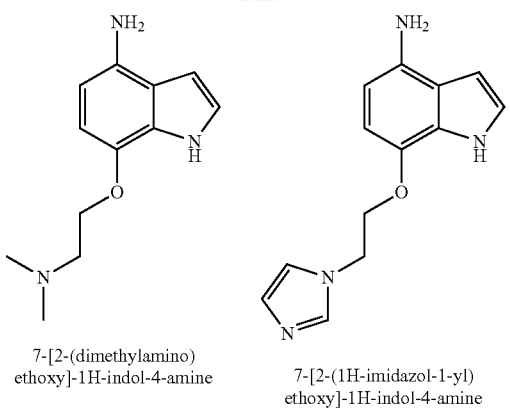

7-[2-(dimethylamino)ethoxy]-1H-indol-4-amine

7-[2-(1H-imidazol-1-yl)ethoxy]-1H-indol-4-amine

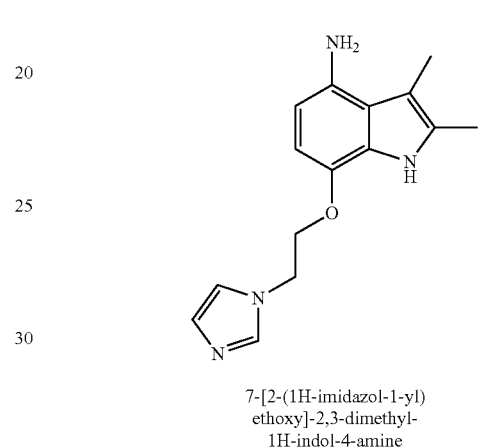

7-[2-(1H-imidazol-1-yl)ethoxy]-2,3-dimethyl-1H-indol-4-amine

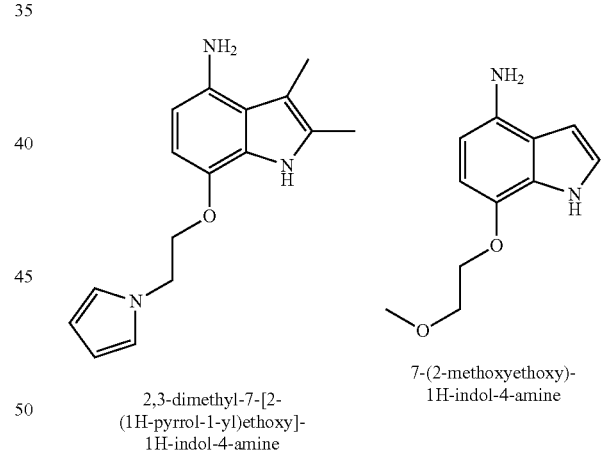

2,3-dimethyl-7-[2-(1H-pyrrol-1-yl)ethoxy]-1H-indol-4-amine 7-(2-methoxyethoxy)-1H-indol-4-amine

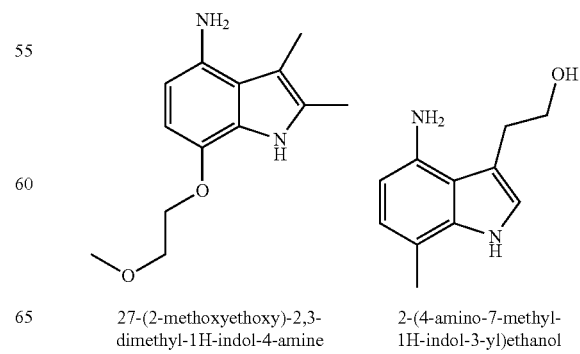

27-(2-methoxyethoxy)-2,3-dimethyl-1H-indol-4-amine 2-(4-amino-7-methyl-1H-indol-3-yl)ethanol

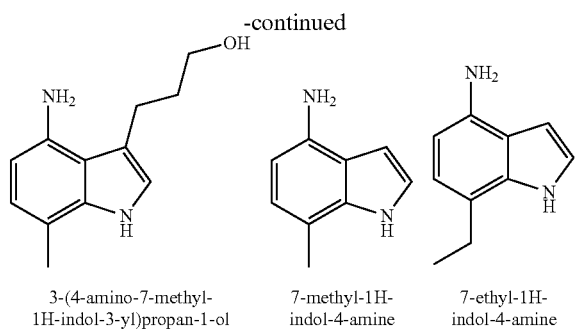

3-(4-amino-7-methyl-1H-indol-3-yl)propan-1-ol    7-methyl-1H-indol-4-amine    7-ethyl-1H-indol-4-amine The compounds of formulae (I), (II), (III) and (IV), the compounds of formula (V), and the addition salts thereof, solvates of thereof and solvates of the salts thereof are in general each present in an amount of between 0.001% and 10% by weight approximately and preferably between 0.005% and 6% by weight relative to the total weight of the dye composition.

The dye composition of the invention may optionally comprise one or more additional oxidation bases conventionally used for dyeing keratin fibres, other than the compounds of formulae (I), (II), (III) and (IV) or the addition salts thereof, solvates thereof and solvates of the salts thereof.

By way of example, these additional oxidation bases are chosen from para-phenylenediamines, bis(phenyl)alkylenediamines, para-aminophenols, bis-para-aminophenols, ortho-aminophenols, heterocyclic bases other than the bases of formula (I), and the addition salts thereof, solvates thereof and solvates of the salts thereof.

Among the para-phenylenediamines, examples that may be mentioned include para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(3-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid, solvates thereof or solvates of the salts thereof.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, solvates thereof and solvates of the salts thereof are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis((3-hydroxyethyl)-N,N'-bis(4'-aminophenyl)ethylenediamine, N,N'-bis(4-aminophenyl)tetramethylenediamine, N,N'-bis (β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid, solvates thereof and solvates of the salts thereof.

Among the para-aminophenols, examples that may be mentioned include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, 1-hydroxy-4-methylaminobenzene, 2,2'-methylenebis(4-aminophenol), and the addition salts thereof with an acid, solvates thereof and solvates of the salts thereof.

Among the ortho-aminophenols, examples that may be mentioned include 2-aminophenol, 2-amino-5-methylphenol, 2-amino-6-methylphenol and 5-acetamido-2-aminophenol, and the addition salts thereof with an acid, solvates thereof and solvates of the salts thereof.

Among the heterocyclic bases, examples that may be mentioned include pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid, solvates thereof and solvates of the salts thereof.

Among the pyrimidine derivatives that may be mentioned are the compounds described, for example, in patents DE 2 359 399; JP 88-169 571; JP 05-63124; EP 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,-N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof with an acid, solvates thereof and solvates of the salts thereof.

The additional oxidation base(s) are each generally present in an amount of between 0.001% and 10% by weight and preferably between 0.005% and 6% by weight relative to the total weight of the dye composition.

The dye composition of the invention may optionally comprise one or more additional oxidation bases conventionally used for dyeing keratin fibres, other than the compounds of formula (II) or the addition salts thereof, solvates thereof and solvates of the salts thereof. Among these couplers, mention may be made especially of meta-phenylenediamines, meta-aminophenols, meta-diphenols, naphthalene-based couplers and heterocyclic couplers other than the compounds of formula (II), the addition salts thereof, solvates thereof and solvates of the salts thereof.

Examples of couplers that may be mentioned include 2-methyl-5-aminophenol, 5-N-(β-hydroxyethyl)amino-2-methylphenol, 6-chloro-2-methyl-5-aminophenol, 2,4-dichloro-3-aminophenol, 5-amino-4-chloro-o-cresol, 4-chloro-1,3-dihydroxybenzene, 2,4-diamino-1-(β-hydroxyethyloxy)benzene, 2-amino-4-(β-hydroxyethylamino)-1-methoxybenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 1,5-dihydroxynaphthalene, 2,7-naphthalenediol, 1-acetoxy-2-methylnaphthalene, 6-hydroxyindole, 4-hydroxyindole, 4-hydroxy-N-methylindole, 3,5-diamino-2,6-dimethoxypyridine, 2,6-dihydroxy-3,4-dimethylpyridine, 3-amino-2-methylamino-6-methoxypyridine, 1-N-(β-hydroxyethyl)amino-3,4-methylenedioxybenzene, 2,6-bis(β-hydroxyethylamino) toluene and 3-methyl-1-phenyl-5-pyrazolone, the addition salts thereof with an acid, solvates thereof and solvates of the salts thereof.

The preferred additional couplers are chosen from 2-methyl-5-aminophenol, 5-N-(β-hydroxyethyl)amino-2-methylphenol and 6-chloro-2-methyl-5-aminophenol.

The additional coupler(s) are each generally present in an amount of between 0.001% and 10% by weight approximately and preferably between 0.005% and 6% by weight relative to the total weight of the dye composition.

In general, the addition salts of the additional oxidation bases and additional couplers that may be used in the context of the invention are especially chosen from addition salts with an acid, such as hydrochlorides, hydrobromides, sulfates, citrates, succinates, tartrates, lactates, tosylates, benzenesulfonates, phosphates and acetates, and the addition salts with a base such as sodium hydroxide, potassium hydroxide, ammonia, amines or alkanolamines.

The dye composition in accordance with the invention may also contain one or more direct dyes that may be chosen especially from nitrobenzene dyes, azo direct dyes and methine direct dyes. These direct dyes may be of nonionic, anionic or cationic nature. They may be synthetic or of natural origin.

The medium that is suitable for dyeing, also known as the dye support, generally comprises water or a mixture of water and of one or more organic solvents, for instance $C_1$-$C_4$ lower alkanols such as ethanol and isopropanol, polyols, for instance propylene glycol, dipropylene glycol or glycerol, and polyol ethers, for instance dipropylene glycol monomethyl ether.

The solvent(s) are generally present in proportions that may be between 1% and 40% by weight approximately and even more preferentially between 3% and 30% by weight approximately relative to the total weight of the dye composition.

The dye composition in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrating agents, sequestering agents, fragrances, buffers, dispersants, conditioning agents, for instance volatile or non-volatile, modified or unmodified silicones, film-forming agents, ceramides, preserving agents and opacifiers.

The above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The pH of the dye composition in accordance with the invention is generally between 3 and 12 approximately and preferably between 5 and 11 approximately. It may be adjusted to the desired value by means of acidifying or basifying agents usually used in the dyeing of keratin fibres, or alternatively using standard buffer systems.

Among the acidifying agents that may be mentioned, for example, are mineral or organic acids, for instance hydrochloric acid, (ortho)phosphoric acid or sulfuric acid, carboxylic acids, for instance acetic acid, tartaric acid, citric acid and lactic acid, and sulfonic acids.

Among the basifying agents, examples that may be mentioned include aqueous ammonia, alkali metal carbonates, sodium metasilicate, sodium silicate, alkanolamines such as monoethanolamine, diethanolamine, triethanolamine and derivatives thereof, for example monoethanolamine, aminomethylpropanol, triethanolamine, sodium hydroxide, potassium hydroxide, sodium pyrrolidinecarboxylate, and the compounds of formula (III) below:

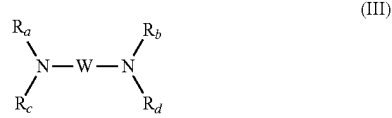

in which W is a propylene residue optionally substituted with a hydroxyl group or a $C_1$-$C_4$ alkyl radical; $R_a$, $R_b$, $R_c$, and $R_d$, which may be identical or different, represent a hydrogen atom or a $C_1$-$C_4$ alkyl or $C_1$-$C_4$ hydroxyalkyl radical.

The composition according to the invention may comprise one or more oxidizing agents.

The oxidizing agents are those conventionally used for the oxidation dyeing of keratin fibres, for example hydrogen peroxide, urea peroxide, alkali metal bromates, persalts such as perborates and persulfates, peracids and oxidase enzymes, among which mention may be made of peroxidases, two-electron oxidoreductases such as uricases, and four-electron oxygenases, for instance laccases. Hydrogen peroxide is particularly preferred.

The composition with or without oxidizing agent according to the invention may be in various forms, such as in the form of liquids, creams or gels, or in any other form that is suitable for dyeing keratin fibres, and especially human hair.

It may result from the mixing at the time of use of several compositions.

In one particular variant, it results from the mixing of two compositions, one comprising at least one oxidation base chosen from the compounds of formula (I), addition salts thereof, solvates thereof and solvates of the salts thereof, and at least one coupler chosen from the compounds of formula (II), and also the addition salts thereof, solvates thereof and solvates of the salts thereof, and another composition comprising at least one oxidizing agent as described previously.

The composition of the invention is thus applied to the hair for the dyeing of keratin fibres, either in unmodified form or in the presence of at least one oxidizing agent for the dyeing of keratin fibres.

The process of the present invention is a process in which the composition free of oxidizing agent according to the present invention as defined previously is applied to the fibres in the presence of an oxidizing agent for a time that is sufficient to develop the desired coloration. The colour may be revealed at acidic, neutral or alkaline pH, and the oxidizing agent may be added to the composition of the invention right at the time of use, or it may be used starting with an oxidizing composition containing it, which is applied simultaneously with or sequentially to the composition of the invention.

According to one particular embodiment, the composition free of oxidizing agent according to the present invention is mixed, preferably at the time of use, with a composition containing, in a suitable dyeing medium, at least one oxidizing agent. The mixture obtained is then applied to the keratin fibres. After a contact time of 3 to 50 minutes approximately and preferably 5 to 30 minutes approximately, the keratin fibres are rinsed, optionally washed with shampoo, rinsed again and then dried.

The oxidizing agents are those described previously.

The oxidizing composition may also contain various adjuvants conventionally used in compositions for dyeing the hair and as defined above.

The pH of the oxidizing composition containing the oxidizing agent is such that, after mixing with the dye composition, the pH of the resulting composition applied to the keratin fibres preferably ranges between 3 and 12 approximately and even more preferentially between 5 and 11. It may be adjusted to the desired value by means of acidifying or basifying agents usually used in the dyeing of keratin fibres and as defined previously.

A subject of the invention is also a multi-compartment dyeing device or "kit" in which a first compartment contains the dye composition free of oxidizing agent of the present invention defined above, comprising at least one oxidation base chosen from the compounds of formula (I), the addition salts thereof, solvates thereof and solvates of the salts thereof, and at least one coupler chosen from the compounds of formula (II), and also the addition salts thereof, solvates thereof and solvates of the salts thereof, and a second compartment containing at least one oxidizing agent.

A second device is formed from a first compartment containing a composition comprising at least one oxidation base chosen from the compounds of formula (I), the addition salts thereof, solvates thereof and solvates of the salts thereof, and a second compartment containing a composition comprising at least one coupler chosen from the compounds of formula (II) as defined previously, and also the addition salts thereof, solvates thereof and solvates of the salts thereof.

A third device may optionally comprise the two compartments of the second device plus a third compartment containing a composition comprising at least one oxidizing agent.

These devices may be equipped with a means for dispensing the desired mixture on the hair, such as the devices described in patent FR-2 586 913 in the name of the Applicant.

The compounds of formulae (II) and (III) are synthesized according to a procedure such as those described in documents EP 1 792 903 and EP 1 792 606.

The compounds of formula (IV) are synthesized according to a procedure such as those described in document EP 0 550 656.

According to a second particular embodiment, the synthesis of the compounds of formula (V) is performed according to the following scheme:

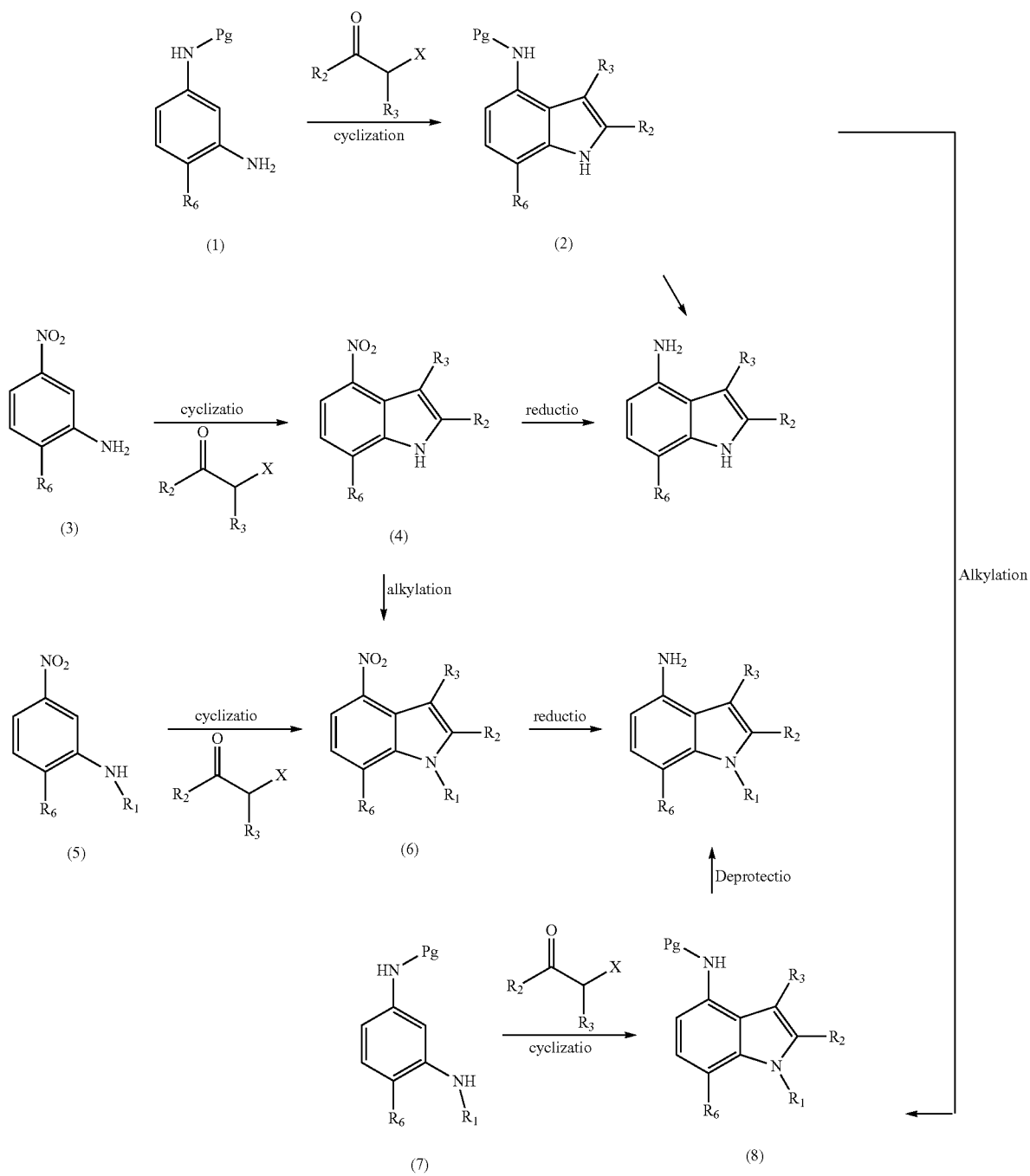

in which:

Pg is a protecting group for the amine function chosen from those mentioned in the publication *Protective Groups in Organic Synthesis*, T. W. Greene, P. G. M. Wutz, John Wiley & Sons, 2nd Ed, 1991;

X denotes a halogen atom such as a fluorine, chlorine, bromine or iodine atom.

According to another particular embodiment, the synthesis of the compounds of formula (V) is performed according to the following scheme:

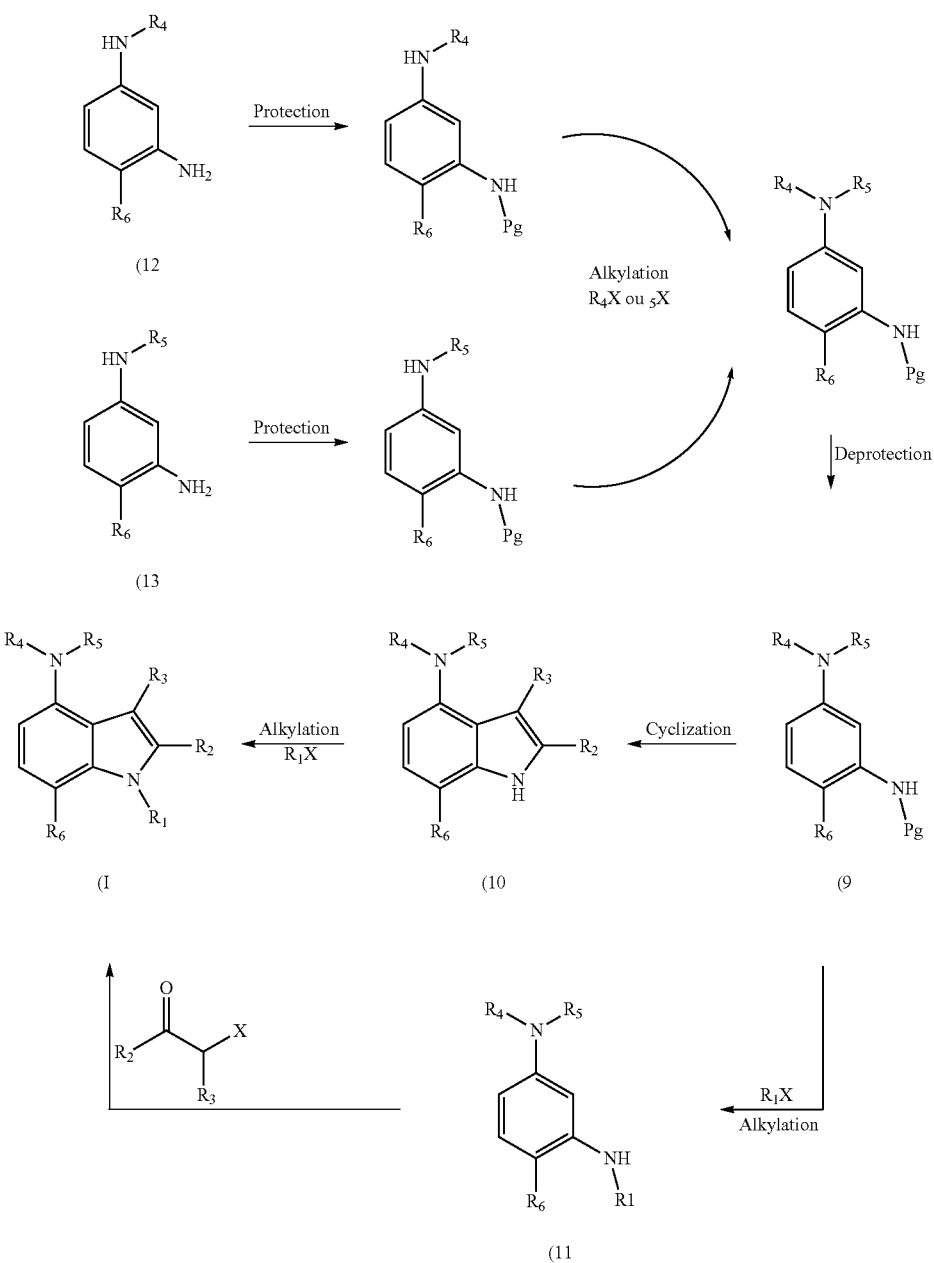

The compounds (2) are obtained from the protected amines (1) via a cyclization reaction of Bischler type performed in a dipolar solvent such as DMF, NMP, acetonitrile or THF, or in an alcohol such as ethanol, for example, optionally in the presence of an organic or mineral base such as triethylamine, ethyldiisopropylamine, sodium hydroxide or potassium hydroxide, with 0.5 to 1 or more equivalents of carbonyl halide $R_2$—CO—CHX—$R_3$ for 1 to 24 hours at a temperature ranging from 20° C. to the reflux temperature of the solvent. The cyclization reactions of (3) to lead to (4), or of (5) to lead to (6), or of (7) to lead to (8), or of (9) to lead to (10), or of (11) to lead to (I), are performed in the same manner.

The alkylation of compounds (4) is performed with at least one equivalent of alkyl halide $R_1$—X in a solvent such as THF or acetonitrile or dioxane or ethyl acetate, in the presence of an organic or mineral base such as triethylamine, ethyldiiso- propylamine, sodium hydroxide or potassium hydroxide, for 15 minutes to 24 hours at a temperature ranging from 15° C. to the reflux temperature of the solvent and leads to compounds (6). The alkylation of compounds (2) to give compounds (8), or of (9) to give (11), or of (10) to give (I), is performed according to an identical protocol.

The reduction of the nitro group of the compounds (4) and (6) is performed under standard conditions, for example by performing a hydrogenation reaction under heterogeneous catalysis in the presence of a catalyst such as Pd/C, Pd(II)/C or Ni/Ra, or alternatively by performing a reduction reaction with a metal, for example with zinc, iron or tin (see *Advanced Organic Chemistry*, 3rd Edition, J. March, 1985, Wiley Interscience and Reduction in *Organic Chemistry*, M. Hudlicky, 1983, Ellis Horwood Series Chemical Science).

The cleavage of the protecting group Pg may be performed in acidic or basic medium in a very conventional manner, depending on their nature (see *Protective Groups for Organic Synthesis*, T. W. Greene, P. G. M. Wutz, John Wiley & Sons, 2nd Ed, 1991).

When compounds (9) are not commercially available, they may be obtained, for example, from the diamines (12) or (13).

The examples that follow serve to illustrate the invention without, however, being limiting in nature.

EXAMPLES

Examples of Synthesis

Example 1

Synthesis of 2,3,7-trimethyl-1H-indol-4-amine hydrochloride

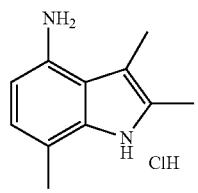

Step 1: Synthesis of
N-(2,3,7-trimethyl-1H-indol-4-yl)acetamide

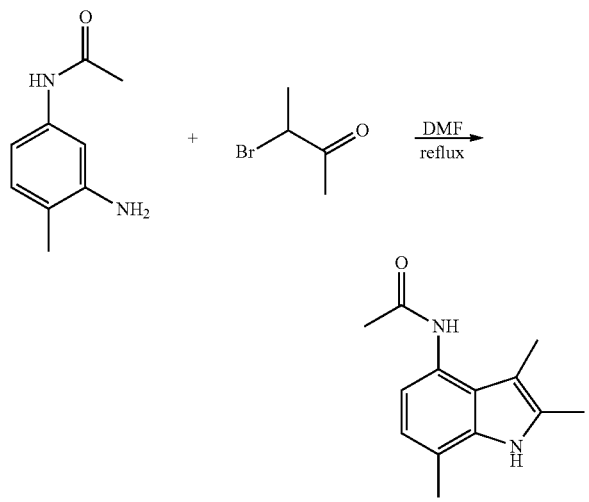

5 g (30 mmol) of N-(3-amino-4-methylphenyl)acetamide are placed in 12 ml of dimethylformamide in a 25 ml three-necked flask equipped with a condenser, a thermometer and a magnetic stirrer, and 3.24 ml (30 mmol) of 3-bromo-2-butanone are added dropwise. The mixture is then maintained at 100° C. for 8 hours until the starting material has totally disappeared.

The reaction medium is cooled and then poured into a mixture of ice and water.

The gummy precipitate formed is taken up in dichloromethane.

The organic phase is then washed with water, after which it is dried over sodium sulfate, and the solvents are then removed on a rotary evaporator under vacuum.

The crude product thus obtained is purified by flash chromatography on a column of silica (eluent:dichloromethane) to give, after removal of the solvent, 1.4 g of a beige-coloured powder corresponding to the expected product (yield=21.2%).

The NMR analyses ($^1$H 400 MHz and $^{13}$C 100.61 MHz DMSO-$d_6$) are in accordance with the expected structure.

The analysis by mass spectrometry confirms the structure of the expected compound $C_{13}H_{16}N_2O$. The quasi-molecular ions [M+H]+, [M+Na]+, [M−H]− of the expected molecule are mainly detected.

Step 2: Synthesis of
2,37-trimethyl-1H-indol-4-amine hydrochloride

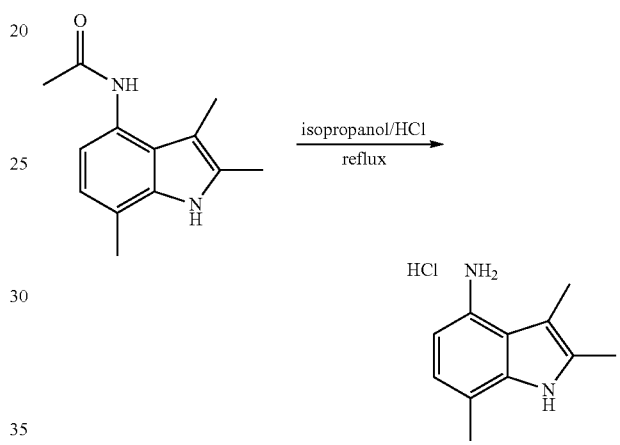

1.4 g (30 mmol) of N-(2,3,7-trimethyl-1H-indol-4-yl)acetamide are placed in 8 ml of a 50% solution of HCl in isopropanol in a 25 ml three-necked flask equipped with a condenser, a thermometer and a magnetic stirrer. The medium is refluxed for 48 hours.

The solvent is then removed under vacuum on a rotary evaporator to give 1.15 g of a grey powder corresponding to the expected compound (yield=64%).

The analysis by mass spectrometry confirms the expected structure $C_{11}H_{14}N_2$. The quasi-molecular ions [M+H]+, [M+Na]+, [M−H]− of the expected molecule are mainly detected.

Example 2

Synthesis of 2,3-dimethyl-7-(propan-2-yl)-1H-indol-4-amine hydrochloride

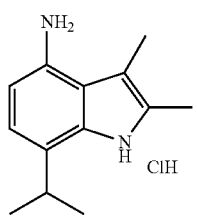

Step 1: Synthesis of N-[2,3-dimethyl-7-(propan-2-yl)-1H-indol-4-yl]acetamide

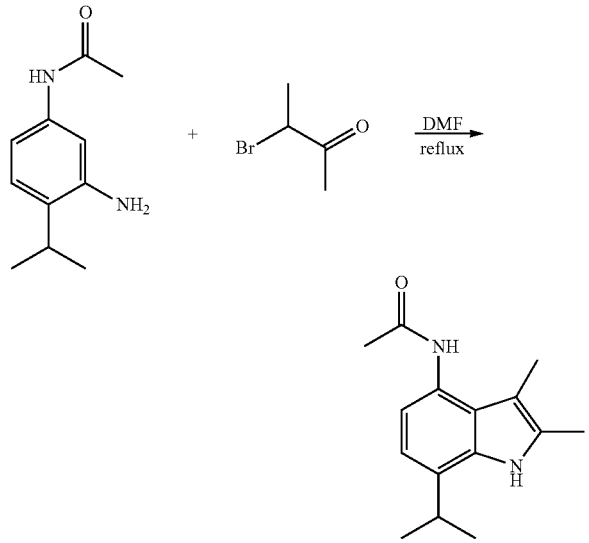

6.7 g (34.8 mmol) of N-[3-amino-4-(1-methylethyl)phenyl]acetamide are placed in 20 ml of dimethylformamide in a 25 ml three-necked flask equipped with a condenser, a thermometer and a magnetic stirrer, and 1.4 ml (13 mmol) of 3-bromo-2-butanone are then added dropwise.

The medium is then maintained at 100° C. for 48 hours, and is then cooled and poured into a mixture of ice and water, with stirring.

The precipitate formed is filtered off and washed thoroughly with water, and then dried under vacuum in the presence of a desiccant.

The crude product thus obtained is purified by flash chromatography on a column of silica (eluent: 95/5 dichloromethane/methanol) to give, after removal of the solvent, 2.87 g of a brown powder corresponding to the expected product (yield=51%).

The NMR analyses ($^1$H 400 MHz and $^{13}$C 100.61 MHz DMSO-$d_6$) are in accordance with the expected structure.

The analysis by mass spectrometry confirms the structure of the expected compound $C_{15}H_{20}N_2O$. The quasi-molecular ions [M+H]+, [M+Na]+, [M−H]− of the expected molecule are mainly detected.

Step 2: Synthesis of 2,3-dimethyl-7-(propan-2-yl)-1H-indol-4-amine hydrochloride

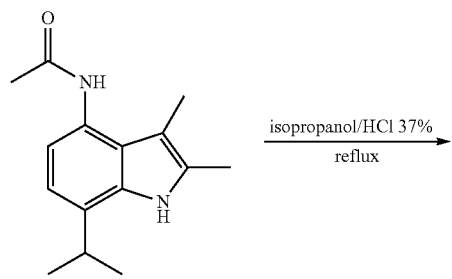

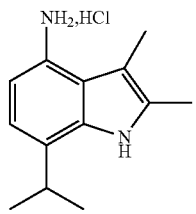

This compound is obtained according to a protocol identical to that described for Example 1, replacing the 6N HCl isopropanol solution with 6 ml of a 37.5% hydrochloric acid solution. For this example, the reaction of 2.87 g of N-[2,3-dimethyl-7-(propan-2-yl)-1H-indol-4-yl]acetamide leads to 2.8 g of a powder corresponding to the expected product (yield=89%).

The NMR analyses ($^1$H 400 MHz and $^{13}$C 100.61 MHz DMSO-$d_6$) are in accordance with the expected structure.

The analysis by mass spectrometry confirms the structure of the expected compound $C_{13}H_{18}N_2$. The quasi-molecular ions [M+H]+, [M+Na]+, [M−H]− of the expected molecule are mainly detected.

Examples of Dyeing 1

Composition C1 below was prepared:

|  | 1C1 |  |
|---|---|---|
| 2-(4,5-Diamino-1H-pyrazol-1-yl)ethanol sulfate | 0.005 | mol |
| 7-Methyl-1H-indol-4-amine | 0.005 | mol |
| Oleyl alcohol polyglycerolated with 2 mol of glycerol | 4 | g AM |
| Oleyl alcohol polyglycerolated with 4 mol of glycerol (78% AM) | 6 | g AM |
| Oleic acid | 3 | g |
| Oleylamine 2 OE sold under the name Ethomeen 012 by the company Akzo | 7 | g AM |
| Diethylaminopropyl laurylaminosuccinate, sodium salt, at 55% AM | 3 | g AM |
| Oleyl alcohol | 5 | g |
| (50% linear 70/30 C13/C15) alkyl ether carboxylic acid monoethanolamide (2 OE) | 10 | g AM |
| Propylene glycol | 9.5 | g |
| Ethyl alcohol | 5 | g |
| Hexylene glycol | 9.3 | g |
| Sodium metabisulfite as an aqueous solution containing 35% AM | 0.455 | g AM |
| Ammonium acetate | 0.8 | g |
| Antioxidant, sequestrant | qs | |
| Fragrance, preservative | qs | |
| Aqueous ammonia containing 20% $NH_3$ | 10.2 | g |
| Demineralized water | qs 100 | g |

AM: Active Material

Mode of Application

The composition was diluted extemporaneously with 1 times its own weight of 20-volumes aqueous hydrogen peroxide solution.

The mixture was then applied to locks of grey hair containing 90% white hairs, at a rate of 10 g of mixture per 1 g of hair. After a leave-on time of 30 minutes at room temperature (25° C.), the hair was then rinsed, washed with a standard shampoo and dried.

Results

The hair coloration was evaluated visually.

| Composition | Tone depth | Tint |
|---|---|---|
| 1C1 | Chestnut brown | Violet |

The coloration obtained is particularly chromatic.

Composition 1C2 below was prepared:

|  | 1C2 |  |
|---|---|---|
| 2-(4,5-Diamino-1H-pyrazol-1-yl)ethanol sulfate | 0.005 | mol |
| 2,3,7-Trimethyl-1H-indol-4-amine hydrochloride | 0.005 | mol |
| Oleyl alcohol polyglycerolated with 2 mol of glycerol | 4 | g AM |
| Oleyl alcohol polyglycerolated with 4 mol of glycerol (78% AM) | 6 | g AM |
| Oleic acid | 3 | g |
| Oleylamine 2 OE sold under the name Ethomeen O12 by the company Akzo | 7 | g AM |
| Diethylaminopropyl laurylaminosuccinate, sodium salt, at 55% AM | 3 | g AM |
| Oleyl alcohol | 5 | g |
| (50% linear 70/30 C13/C15) alkyl ether carboxylic acid monoethanolamide (2 OE) | 10 | g AM |
| Propylene glycol | 9.5 | g |
| Ethyl alcohol | 5 | g |
| Hexylene glycol | 9.3 | g |
| Sodium metabisulfite as an aqueous solution containing 35% AM | 0.455 | g AM |
| Ammonium acetate | 0.8 | g |
| Antioxidant, sequestrant | qs |  |
| Fragrance, preservative | qs |  |
| Aqueous ammonia containing 20% NH$_3$ | 10.2 | g |
| Demineralized water | qs 100 | g |

AM: Active Material

Mode of Application

The composition was diluted extemporaneously with 1 times its own weight of 20-volumes aqueous hydrogen peroxide solution.

The mixture was then applied to locks of grey hair containing 90% white hairs, at a rate of 10 g of mixture per 1 g of hair. After a leave-on time of 30 minutes at room temperature (25° C.), the hair was then rinsed, washed with a standard shampoo and dried.

Results

The hair coloration was evaluated visually.

| Composition | Tone depth | Tint |
|---|---|---|
| 1C2 | Chestnut brown | Violet |

The coloration obtained is particularly chromatic.

Examples of Dyeing 2

Compositions 2C1 and 2C'1 below were prepared.

|  | 2C1 |  | 2C'1 |  |
|---|---|---|---|---|
| 4-(3-Aminopyrazolo[1,5-a]pyridin-2-yl)-1,2-dimethylpiperazin-1-ium chloride hydrochloride | 0.005 | mol | 0.005 | mol |
| 7-Methyl-1H-indol-4-amine | 0.005 | mol | — |  |
| 2,3,7-trimethyl-1H-indol-4-amine | — |  | 0.005 | mol |
| Oleyl alcohol polyglycerolated with 2 mol of glycerol | 4 | g AM | 4 | g AM |
| Oleyl alcohol polyglycerolated with 4 mol of glycerol (78% AM) | 6 | g AM | 6 | g AM |
| Oleic acid | 3 | g | 3 | g |
| Oleylamine 2 OE sold under the name Ethomeen O12 by the company Akzo | 7 | g AM | 7 | g AM |
| Diethylaminopropyl laurylaminosuccinate, sodium salt, at 55% AM | 3 | g AM | 3 | g AM |
| Oleyl alcohol | 5 | g | 5 | g |
| (50% linear 70/30 C13/C15) alkyl ether carboxylic acid monoethanolamide (2 OE) | 10 | g AM | 10 | g AM |
| Propylene glycol | 9.5 | g | 9.5 | g |
| Ethyl alcohol | 5 | g | 5 | g |
| Hexylene glycol | 9.3 | g | 9.3 | g |
| Sodium metabisulfite as an aqueous solution containing 35% AM | 0.455 | g AM | 0.455 | g AM |
| Ammonium acetate | 0.8 | g | 0.8 | g |
| Antioxidant, sequestrant | qs |  | qs |  |
| Fragrance, preservative | qs |  | qs |  |
| Aqueous ammonia containing 20% NH$_3$ | 10.2 | g | 10.2 | g |
| Demineralized water | qs 100 | g | qs 100 | g |

AM: Active Material

Mode of Application

Each of the compositions 2C1 and 2C'1 was diluted extemporaneously with 1 times its own weight of 20-volumes aqueous hydrogen peroxide solution.

Each of the mixtures was applied to locks of grey hair containing 90% white hairs, at a rate of 10 g of mixture per 1 g of hair. After a leave-on time of 30 minutes at room temperature (25° C.), the hair was then rinsed, washed with a standard shampoo and dried.

Results

The hair coloration was evaluated visually.

| Composition | Tone depth | Tint |
|---|---|---|
| 2C1 | Blond | Blue |
| 2C'1 | Blond | Blue |

Composition 2C2 and 2C'2 below were prepared.

|  | 2C2 |  | 2C'2 |  |
|---|---|---|---|---|
| 1-{2-[(3-Aminopyrazolo[1,5-a]pyridin-2-yl)amino]ethyl}-3-methyl-1H-imidazol-3-ium chloride hydrochloride | 0.008 | mol | 0.008 | mol |
| 7-Methyl-1H-indol-4-amine | 0.008 | mol | — |  |
| 2,3,7-Trimethyl-1H-indol-4-amine | — |  | 0.008 | mol |
| Oleyl alcohol polyglycerolated with 2 mol of glycerol | 4 | g AM | 4 | g AM |
| Oleyl alcohol polyglycerolated with 4 mol of glycerol (78% AM) | 6 | g AM | 6 | g AM |
| Oleic acid | 3 | g | 3 | g |
| Oleylamine 2 OE sold under the name Ethomeen O12 by the company Akzo | 7 | g AM | 7 | g AM |
| Diethylaminopropyl laurylaminosuccinate, sodium salt, at 55% AM | 3 | g AM | 3 | g AM |
| Oleyl alcohol | 5 | g | 5 | g |
| (50% linear 70/30 C13/C15) alkyl ether carboxylic acid monoethanolamide (2 OE) | 10 | g AM | 10 | g AM |
| Propylene glycol | 9.5 | g | 9.5 | g |
| Ethyl alcohol | 5 | g | 5 | g |
| Hexylene glycol | 9.3 | g | 9.3 | g |
| Sodium metabisulfite as an aqueous solution containing 35% AM | 0.455 | g AM | 0.455 | g AM |
| Ammonium acetate | 0.8 | g | 0.8 | g |
| Antioxidant, sequestrant | qs |  | qs |  |
| Fragrance, preservative | qs |  | qs |  |
| Aqueous ammonia containing 20% NH$_3$ | 10.2 | g | 10.2 | g |
| Demineralized water | qs 100 | g | qs 100 | g |

AM: Active Material

Mode of Application

Each of the compositions 2C2 and 2C'2 was diluted extemporaneously with 1 times its own weight of 20-volumes aqueous hydrogen peroxide solution.

Each of the mixtures was applied to locks of grey hair containing 90% white hairs, at a rate of 10 g of mixture per 1 g of hair. After a leave-on time of 30 minutes at room temperature (25° C.), the hair was then rinsed, washed with a standard shampoo and dried.

Results

The hair coloration was evaluated visually.

| Composition | Tone depth | Tint |
|---|---|---|
| 2C2 | Chestnut brown | Deep blue |
| 2C'2 | Chestnut brown | Deep blue |

Compositions 2C3 and 2C'3 below were prepared.

|  | C3 | C'3 |
|---|---|---|
| 2-[(3-Aminopyrazolo[1,5-a]pyridin-2-yl)oxy]ethanol hydrochloride | 0.01 mol | 0.01 mol |
| 7-Methyl-1H-indol-4-amine | 0.01 mol | — |
| 2,3,7-Trimethyl-1H-indol-4-amine | — | 0.01 mol |
| Oleyl alcohol polyglycerolated with 2 mol of glycerol | 4 g AM | 4 g AM |
| Oleyl alcohol polyglycerolated with 4 mol of glycerol (78% AM) | 6 g AM | 6 g AM |
| Oleic acid | 3 g | 3 g |
| Oleylamine 2 OE sold under the name Ethomeen 012 by the company Akzo | 7 g AM | 7 g AM |
| Diethylaminopropyl laurylaminosuccinate, sodium salt, at 55% AM | 3 g AM | 3 g AM |
| Oleyl alcohol | 5 g | 5 g |
| (50% linear 70/30 C13/C15) alkyl ether carboxylic acid monoethanolamide (2 OE) | 10 g AM | 10 g AM |
| Propylene glycol | 9.5 g | 9.5 g |
| Ethyl alcohol | 5 g | 5 g |
| Hexylene glycol | 9.3 g | 9.3 g |
| Sodium metabisulfite as an aqueous solution containing 35% AM | 0.455 g AM | 0.455 g AM |
| Ammonium acetate | 0.8 g | 0.8 g |
| Antioxidant, sequestrant | qs | qs |
| Fragrance, preservative | qs | qs |
| Aqueous ammonia containing 20% $NH_3$ | 10.2 g | 10.2 g |
| Demineralized water | qs 100 g | qs 100 g |

AM: Active Material

Mode of Application

Each of the compositions 2C3 and 2C'3 was diluted extemporaneously with 1 times its own weight of 20-volumes aqueous hydrogen peroxide solution.

Each of the mixtures was applied to locks of grey hair containing 90% white hairs, at a rate of 10 g of mixture per 1 g of hair. After a leave-on time of 30 minutes at room temperature (25° C.), the hair was then rinsed, washed with a standard shampoo and dried.

Results

The hair coloration was evaluated visually.

| Composition | Tone depth | Tint |
|---|---|---|
| 2C3 | Dark chestnut-brown | Natural |
| 2C'3 | Dark chestnut-brown | Natural |

Examples of Dyeing 3

Composition 3C1 below was prepared:

|  | 3C1 |
|---|---|
| 2,3-Diamino-6,7-dihydro-1H,5H-pyrazolo[1,2-a]pyrazol-1-one dimethanesulfonate | 0.005 mol |
| 7-Methyl-1H-indol-4-amine | 0.005 mol |
| Oleyl alcohol polyglycerolated with 2 mol of glycerol | 4 g AM |
| Oleyl alcohol polyglycerolated with 4 mol of glycerol (78% AM) | 6 g AM |
| Oleic acid | 3 g |
| Oleylamine 2 OE sold under the name Ethomeen 012 by the company Akzo | 7 g AM |
| Diethylaminopropyl laurylaminosuccinate, sodium salt, at 55% AM | 3 g AM |
| Oleyl alcohol | 5 g |
| (50% linear 70/30 C13/C15) alkyl ether carboxylic acid monoethanolamide (2 OE) | 10 g AM |
| Propylene glycol | 9.5 g |
| Ethyl alcohol | 5 g |
| Hexylene glycol | 9.3 g |
| Sodium metabisulfite as an aqueous solution containing 35% AM | 0.455 g AM |
| Ammonium acetate | 0.8 g |
| Antioxidant, sequestrant | qs |
| Fragrance, preservative | qs |
| Aqueous ammonia containing 20% $NH_3$ | 10.2 g |
| Demineralized water | qs 100 g |

AM: Active Material

Mode of Application

The composition was diluted extemporaneously with 1 times its own weight of 20-volumes aqueous hydrogen peroxide solution.

The mixture was then applied to locks of grey hair containing 90% white hairs, at a rate of 10 g of mixture per 1 g of hair. After a leave-on time of 30 minutes at room temperature (25° C.), the hair was then rinsed, washed with a standard shampoo and dried.

Results

The hair coloration was evaluated visually.

| Composition | Tone depth | Tint |
|---|---|---|
| 3C1 | Blond | Golden |

Composition C2 below was prepared:

|  | 3C2 |
|---|---|
| 2,3-Diamino-6,7-dihydro-1H,5H-pyrazolo[1,2-a]pyrazol-1-one dimethanesulfonate | 0.005 mol |
| 2,3,7-Trimethyl-1H-indol-4-amine hydrochloride | 0.005 mol |
| Oleyl alcohol polyglycerolated with 2 mol of glycerol | 4 g AM |
| Oleyl alcohol polyglycerolated with 4 mol of glycerol (78% AM) | 6 g AM |
| Oleic acid | 3 g |
| Oleylamine 2 OE sold under the name Ethomeen 012 by the company Akzo | 7 g AM |
| Diethylaminopropyl laurylaminosuccinate, sodium salt, at 55% AM | 3 g AM |
| Oleyl alcohol | 5 g |
| (50% linear 70/30 C13/C15) alkyl ether carboxylic acid monoethanolamide (2 OE) | 10 g AM |
| Propylene glycol | 9.5 g |
| Ethyl alcohol | 5 g |
| Hexylene glycol | 9.3 g |
| Sodium metabisulfite as an aqueous solution containing 35% AM | 0.455 g AM |
| Ammonium acetate | 0.8 g |
| Antioxidant, sequestrant | qs |
| Fragrance, preservative | qs |
| Aqueous ammonia containing 20% $NH_3$ | 10.2 g |
| Demineralized water | qs 100 g |

AM: Active Material

Mode of Application

The composition was diluted extemporaneously with 1 times its own weight of 20-volumes aqueous hydrogen peroxide solution.

The mixture was then applied to locks of grey hair containing 90% white hairs, at a rate of 10 g of mixture per 1 g of hair. After a leave-on time of 30 minutes at room temperature (25° C.), the hair was then rinsed, washed with a standard shampoo and dried.

Results

The hair coloration was evaluated visually.

| Composition | Tone depth | Tint |
|---|---|---|
| 3C2 | Blond | Golden |

The invention claimed is:

1. A composition for dyeing keratin fibers, comprising, in a cosmetically acceptable dyeing medium:

a) at least one oxidation base chosen from
4,5-diaminopyrazole derivatives of formula (I), and addition salts, solvates, and solvates of the salts thereof:

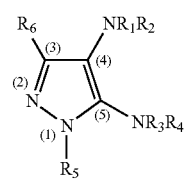

(I)

wherein:

$R_1$, $R_2$, $R_3$, $R_4$, $R_5$ and $R_6$, which may be identical or different, are chosen from hydrogen atoms and $C_1$-$C_6$ alkyl radicals which are optionally substituted with at least one substituent chosen from OR, NHR, NRR', SR, SOR, $SO_2R$, COR, COOH, $CONH_2$, CONHR, CONRR', $PO(OH)_2$, SH, $SO_3X$, non-cationic heterocycles, Cl, Br, and I, wherein X is chosen from hydrogen atoms, Na, K, and $NH_4$, and R and R', which may be identical or different, are chosen from $C_1$-$C_4$ alkyl radicals, $C_1$-$C_4$ alkenyl radicals; $C_2$-$C_4$ hydroxyalkyl radicals; $C_2$-$C_4$ aminoalkyl radicals; phenyl radicals; phenyl radicals substituted with at least one of halogen atoms, and $C_1$-$C_4$ alkyl radicals, $C_1$-$C_4$ alkoxy radicals, nitro radicals, trifluoromethyl radicals, amino radicals, $C_1$-$C_4$ alkylamino radicals; benzyl radicals; benzyl radicals substituted with at least one of halogen atoms and $C_1$-$C_4$ alkyl radicals, $C_1$-$C_4$ alkoxy radicals, methylenedioxy radicals, amino radicals; radicals having the formula:

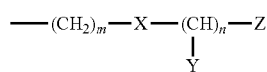

wherein m and n are integers, which may be identical or different, ranging from 0 to 3, X is chosen from oxygen atoms and NH groups, Y is chosen from hydrogen atoms and $C_1$-$C_4$ alkyl radicals, and Z is a methyl radical when n is equal to 0, or Z is chosen from $C_1$-$C_4$ alkyl radicals, OR groups, and NR"R'" groups when n is greater than or equal to 1, wherein R" and R'", which may be identical or different, are chosen from hydrogen atoms and $C_1$-$C_4$ alkyl radicals;

or $R_5$ forms, with the nitrogen atom of the group $NR_3R_4$ in position 5, a heterocycle that is at least 4-membered; wherein at least one of the radicals $R_1$, $R_2$, $R_3$ and $R_4$ is a hydrogen atom;

aminopyrazolopyridine oxidation bases of formula (II), and addition salts, solvates, and solvates of the salts thereof:

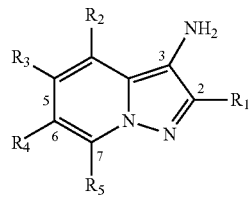

(II)

wherein:

$R_1$, $R_2$, $R_3$, $R_4$ and $R_5$, which may be identical or different, are chosen from hydrogen atoms; halogen atoms; radicals —$NHSO_3H$; hydroxyl radicals; radicals ($C_1$-$C_4$) alkyl; radicals ($C_1$-$C_4$)alkoxy; radicals ($C_1$-$C_4$)alkylthio; mono($C_1$-$C_4$)alkylamino radicals; radicals di($C_1$-$C_4$)alkylamino wherein the two alkyl groups may form, together with the nitrogen atom to which they are attached, a ring that is optionally interrupted with at least one atom chosen from nitrogen, oxygen and sulfur atoms; heterocycles; nitro radicals; phenyl radicals; carbonyl radicals; ($C_1$-$C_4$)alkoxycarbonyl radicals; carboxamido radicals; cyano radicals; amino radicals; sulfonyl radicals; radicals —$CO_2H$, radicals —$SO_3H$; radicals —$PO_3H_2$; radicals —$PO_4H_2$; and groups:

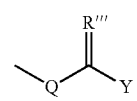

wherein R'" is chosen from oxygen and nitrogen atoms, Q is chosen from oxygen atoms, NH groups, and NH($C_1$-$C_4$)alkyl groups, and Y is chosen from hydroxyl, amino, $C_1$-$C_4$ alkyl, ($C_1$-$C_4$)alkoxy, ($C_1$-$C_4$)alkylamino and di($C_1$-$C_4$)alkylamino radicals;

aminopyrazolopyridine oxidation bases of formula (III)

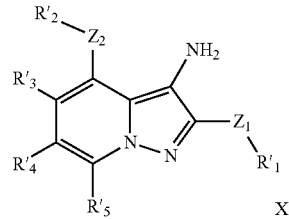

(III)

wherein:

$Z_1$ and $Z_2$, which may be identical or different, are chosen from:
covalent single bonds;
divalent radicals chosen from radicals —$O(CH_2)_p$—, wherein p is an integer ranging from 0 to 6; radicals —NR'$_6$(CH$_2$)$_q$(C$_6$H$_4$)$_t$—, wherein q is an integer ranging from 0 to 6, t is chosen from 0 and 1, and R'$_6$ is chosen from hydrogen atoms and C$_1$-C$_6$ alkyl radicals optionally substituted with at least one hydroxyl group;

Z$_1$ may also be a divalent radical chosen from —S—, —SO— and —SO$_2$— when R'$_1$ is a methyl radical;

R'$_1$ and R'$_2$, which may be identical or different, are chosen from:
hydrogen atoms;
C$_1$-C$_{10}$ alkyl radicals, which are optionally substituted and optionally interrupted with at least one group chosen from heteroatoms, O, N, Si, S, SO, and SO$_2$;
halogen atoms;
SO$_3$H radicals;
5- to 8-membered rings which are optionally substituted, optionally saturated, optionally aromatic, and optionally comprising at least one of heteroatoms and groups chosen from N, O, S, SO$_2$, and —CO—, the ring optionally being cationic and and optionally substituted with a cationic radical;
groups —N$^+$R$_{17}$R$_{18}$R$_{19}$, wherein R$_{17}$, R$_{18}$ and R$_{19}$ are independently chosen from linear and branched C$_1$-C$_5$ alkyls optionally substituted with and least one hydroxyl group;
wherein when Z$_1$ or, respectively, Z$_2$ is a covalent bond, then R'$_1$ or, respectively, R'$_2$ may also be chosen from the radicals:
optionally substituted C$_1$-C$_6$ alkylcarbonyls;
—O—CO—R, —CO—O—R, NR—CO—R' and —CO—NRR', wherein R and R' independently are chosen from hydrogen atoms and optionally substituted C$_1$-C$_6$ alkyl radicals;

R'$_3$, R'$_4$ and R'$_5$, which may be identical or different, are chosen from:
hydrogen atoms;
hydroxyl radicals;
C$_1$-C$_6$ alkoxy radicals;
C$_1$-C$_6$ alkylthio radicals;
amino radicals;
monoalkylamino radicals;
C$_1$-C$_6$ dialkylamino radicals wherein the alkyl radicals may form, with the nitrogen atom to which they are attached, an optionally saturated, optionally aromatic 5- to 8-membered heterocycle, which may comprise at least one heteroatom and group chosen from N, O, S, SO$_2$ and CO, the heterocycle being optionally cationic, and optionally substituted with a cationic radical;
optionally substituted C$_1$-C$_6$ alkylcarbonyl radicals;
radicals —O—CO—R, —CO—O—R, NR—CO—R', and —CO—NRR', wherein R and R' independently are chosen from hydrogen atoms and optionally substituted C$_1$-C$_6$ alkyl radicals;
halogen radicals;
SO$_3$H radicals;
optionally substituted C$_1$-C$_4$ alkyl radicals;
saturated, unsaturated and aromatic, optionally substituted carbon-based rings;
R'$_3$, R'$_4$ and R'$_5$, may form in pairs a partially saturated or unsaturated ring;
X is chosen from ions and groups of ions that provide the electronegativity of the derivative of formula (II);
with the proviso that at least one of the groups R'$_1$ and R'$_2$ is a cationic radical;

oxidation bases chosen from the diamino-N,N-dihydropyrazolone derivatives of formula (IV), and addition salts, solvates, and solvates of the salts thereof:

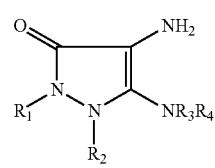

wherein:
R$_1$, R$_2$, R$_3$ and R$_4$, which may be identical or different, are chosen from:
linear and branched C$_1$-C$_6$ alkyl radicals optionally substituted with at least one radical chosen from radicals OR$_5$, radicals NR$_6$R$_7$, carboxyl radicals, sulfonic radicals, carboxamido radicals CONR$_6$R$_7$, sulfonamido radicals SO$_2$NR$_6$R$_7$, heteroaryls, aryls optionally substituted with at least one group chosen from (C$_1$-C$_4$)alkyl, hydroxyl, C$_1$-C$_2$ alkoxy, amino and (di) alkyl(C$_1$-C$_2$)amino groups;
aryl radicals optionally substituted with at least one group chosen from (C$_1$-C$_4$)alkyl, hydroxyl, C$_1$-C$_2$ alkoxy, amino and (di)alkyl(C$_1$-C$_2$)amino groups;
5- and 6-membered heteroaryl radical, optionally substituted with at least one radical chosen from (C$_1$-C$_4$) alkyl and (C$_1$-C$_2$)alkoxy radicals;
R$_3$ and R$_4$ may also independently be chosen from hydrogen atoms;
wherein R$_5$, R$_6$ and R$_7$, which may be identical or different, are chosen from:
hydrogen atoms;
linear and branched C$_1$-C$_4$ alkyl radicals optionally substituted with at least one radical chosen from hydroxyl, C$_1$-C$_2$ alkoxy, carboxamido CONR$_8$R$_9$, sulfonyl SO$_2$R$_8$, aryl optionally substituted with a (C$_1$-C$_4$)alkyl, hydroxyl, C$_1$-C$_2$ alkoxy, amino and (di) alkyl(C$_1$-C$_2$)amino; aryl optionally substituted with a (C$_1$-C$_4$)alkyl, hydroxyl, C$_1$-C$_2$ alkoxy, amino and (di) alkyl(C$_1$-C$_2$)amino radicals;
R$_6$ and R$_7$, which may be identical or different, may also be chosen from carboxamido radicals CONR$_8$R$_9$ and sulfonyl radicals SO$_2$R$_8$;
R$_8$ and R$_9$, which may be identical or different, are chosen from hydrogen atoms; linear and branched C$_1$-C$_4$ alkyl radicals optionally substituted with at least one radical chosen from hydroxyl and C$_1$-C$_2$ alkoxy radicals;
at least one of R$_1$ and R$_2$ and R$_3$ and R$_4$ may form, with the nitrogen atoms to which they are attached, a saturated or unsaturated 5- to 7-membered heterocycle optionally substituted with at least one radical chosen from halogen atoms, amino, (di)alkyl (C$_1$-C$_4$)amino, hydroxyl, carboxyl, carboxamido and (C$_1$-C$_2$)alkoxy radicals, C$_1$-C$_4$ alkyl radicals optionally substituted with at least one hydroxyl, amino, (di)alkylamino, alkoxy, carboxyl and sulfonyl radicals;
R$_3$ and R$_4$ may also form, together with the nitrogen atom to which they are attached, a 5- or 7-membered heterocycle wherein the carbon atoms may be replaced with an optionally substituted oxygen or nitrogen atom;
and
b) at least one coupler chosen from 4-aminoindole derivatives of formula (IIa), and addition salts, solvates, and solvates of the salts thereof:

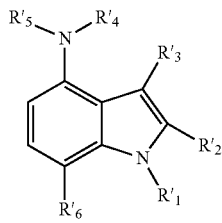

wherein:
R'$_1$ is chosen from
hydrogen atoms; and
linear and branched saturated C$_1$-C$_6$ alkyl radicals, optionally interrupted with an oxygen atom or a radical NR'$_7$, and optionally substituted with a radical chosen from OH and NR'$_7$R'$_8$;
R'$_2$ and R'$_3$, which may be identical or different, are chosen from
hydrogen atoms;
C$_1$-C$_6$ alkyl radicals, optionally substituted with at least one hydroxyl radical;
C$_1$-C$_6$ alkyl carboxylate radicals;
carboxyl radicals; and
radicals CONR'$_7$R'$_8$;
R'$_4$ and R'$_5$, which may be identical or different, are chosen from
hydrogen atoms; and
C$_1$-C$_6$ alkyl radicals;
R'$_6$ is chosen from
halogen atoms;
linear and branched C$_1$-C$_{10}$ alkyl radicals, optionally interrupted with a heteroatom chosen from O and radicals NR'$_9$, and optionally substituted with at least one radical, which may be identical or different, chosen from OH and NR'$_7$R'$_8$;
carboxyl radicals;
C$_1$-C$_{10}$ alkyl carboxylates;
radicals CONR'$_7$R'$_8$;
C$_1$-C$_{10}$ alkoxy radicals and C$_1$-C$_{10}$ (poly)hydroxyalkoxy radicals;
(poly)(C$_1$-C$_{10}$)alkoxy(C$_1$-C$_{10}$)alkyloxy radicals; and
radicals O-Ak-NR'$_9$R'$_{10}$ wherein Ak is chosen from linear C$_1$-C$_8$ and branched C$_3$-C$_8$ divalent alkylene radicals, optionally interrupted with at least one oxygen atom and optionally interrupted with at least one group NR'$_7$; wherein
R'$_7$ and R'$_8$, which may be identical or different, are chosen from
hydrogen atoms;
C$_1$-C$_8$ alkyl radicals optionally substituted with at least one hydroxyl radical; and
R'$_9$ and R'$_{10}$, which may be identical or different, are chosen from linear and branched, saturated and unsaturated C$_1$-C$_4$ alkyl radicals;
wherein R'$_9$ and R'$_{10}$ may form, with the nitrogen that bears them, an optionally saturated 5- to 8-membered heterocycle, wherein one of the chain members is optionally chosen from oxygen atoms and radicals NR'$_{11}$, wherein R'$_{11}$ is chosen from H and C$_1$-C$_4$ alkyl radicals, optionally substituted with at least one radical chosen from OH and NR'$_7$R'$_8$.

2. The composition according to claim 1, wherein, in formula (I), R$_6$ is hydrogen; R$_1$, R$_2$, R$_3$ and R$_4$ are chosen from hydrogen atoms and C$_1$-C$_4$ alkyl radicals; and R$_5$ is chosen from C$_1$-C$_4$ alkyl, hydroxyalkyl and alkoxyalkyl radicals.

3. The composition according to claim 1, wherein the 4,5-diaminopyrazole derivatives of formula (I) are chosen from 4,5-diamino-1-(2-hydroxyethyl)-1H-pyrazole and addition salts, solvates, and solvates of the salts thereof.

4. The composition according to claim 1, wherein the aminopyrazolopyridine oxidation bases of formula (II) are chosen from the compounds of the following formula:

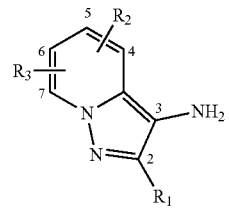

wherein:
R$_1$, R$_2$ and R$_3$, which may be identical or different, are chosen from hydrogen and halogen atoms; hydroxyl radicals; (C$_1$-C$_4$)alkyl radicals; (C$_1$-C$_4$)alkylthio radicals; (C$_1$-C$_4$)alkoxy radicals; —NHSO$_3$H radicals; amino radicals; (C$_1$-C$_4$)alkylamino radicals; di(C$_1$-C$_4$)alkylamino radicals wherein the two alkyl groups may form, together with the nitrogen atom to which they are attached, a ring that is optionally interrupted with at least one atom chosen from nitrogen, oxygen and sulfur atoms; heterocycles; sulfonamide radicals, carbonyl radicals, (C$_1$-C$_4$)alkoxycarbonyl radicals; carboxamido radicals; and groups of the formula:

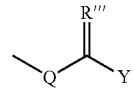

wherein R''' is chosen from oxygen and nitrogen atoms, Q is chosen from oxygen atoms, NH groups, and NH(C$_1$-C$_4$)alkyl groups, and Y is chosen from hydroxyl, amino, C$_1$-C$_4$ alkyl, (C$_1$-C$_4$)alkoxy, (C$_1$-C$_4$)alkylamino and di(C$_1$-C$_4$)alkylamino radicals.

5. The composition according to claim 1, wherein the 3-aminopyrazolo[1,5-a]pyridines of formula (II) are chosen from:
pyrazolo[1,5-a]pyridin-3-ylamine;
2-acetylaminopyrazolo[1,5-a]pyridin-3-ylamine;
2-morpholin-4-ylpyrazolo[1,5-a]pyridin-3-ylamine;
3-aminopyrazolo[1,5-a]pyridine-2-carboxylic acid;
2-methoxypyrazolo[1,5-a]pyridin-3-ylamino;
(3-aminopyrazolo[1,5-a]pyridin-7-yl)methanol;
2-(3-aminopyrazolo[1,5-a]pyridin-5-yl)ethanol;
2-(3-aminopyrazolo[1,5-a]pyridin-7-yl)ethanol;
(3-aminopyrazolo[1,5-a]pyridin-2-yl)methanol;
3,6-diaminopyrazolo[1,5-a]pyridine;
3,4-diaminopyrazolo[1,5-a]pyridine;
pyrazolo[1,5-a]pyridine-3,7-diamine;

7-morpholin-4-ylpyrazolo[1,5-a]pyridin-3-ylamine;
pyrazolo[1,5-a]pyridine-3,5-diamine;
5-morpholin-4-ylpyrazolo[1,5-a]pyridin-3-ylamine;
2-[(3-aminopyrazolo[1,5-a]pyridin-5-yl)(2-hydroxyethyl)amino]ethanol;
2-[(3-aminopyrazolo[1,5-a]pyridin-7-yl)(2-hydroxyethyl)amino]ethanol;
3-aminopyrazolo[1,5-a]pyridin-5-ol;
3-aminopyrazolo[1,5-a]pyridin-4-ol;
3-aminopyrazolo[1,5-a]pyridin-6-ol;
3-aminopyrazolo[1,5-a]pyridin-7-ol;
2-methoxy-6,7-dimethylpyrazolo[1,5-a]pyridin-3-amine;
2-[(3-aminopyrazolo[1,5-a]pyridin-2-yl)oxy]ethanol;
4-ethyl-2-methoxy-7-methylpyrazolo[1,5-a]pyridin-3-amine hydrochloride;
1-(3-aminopyrazolo[1,5-a]pyridin-2-yl)pyrrolidin-3-ol;
2,2'-[(3-aminopyrazolo[1,5-a]pyridin-2-yl)imino]diethanol;
2-[(3-aminopyrazolo[1,5-a]pyridin-2-yl)amino]ethanol;
N2-(2-pyridin-3-ylethyl)pyrazolo[1,5-a]pyridine-2,3-diamine;
and addition salts, solvates, and solvates of the salts thereof.

6. The composition according to claim 1, wherein, in formula (III), at least one of $Z_1$ and $Z_2$ is chosen from covalent bonds, radicals —$NR'_6(CH_2)_q$— and radicals —$O(CH_2)_p$—, and at least one of $R'_1$ and $R'_2$ is a cationic radical.

7. The composition according to claim 1, wherein, in formula (III), $R'_1$ and $R'_2$, which may be identical or different, are chosen from imidazoles substituted with a quaternary ammonium radical, imidazoliums, piperazines substituted with a quaternary ammonium radical, piperaziniums, pyrrolidines substituted with a quaternary ammonium radical, pyrrolidiniums, diazepanes substituted with a quaternary ammonium radical, and diazepaniums.

8. The composition according to claim 1, wherein, in formula (III), $R'_1$ and $R'_2$ independently are chosen from hydrogen atoms, trialkylammonium groups, tri(hydroxyalkyl)ammonium groups, hydroxyalkyldialkylammonium groups and di(hydroxyalkyl)alkylammonium groups.

9. The composition according to claim 1, wherein the radicals $R'_3$, $R'_4$ and $R'_5$ of formula (III) independently are chosen from hydrogen atoms and $C_1$-$C_4$ alkyl radicals, which are optionally substituted.

10. The composition according to claim 1, wherein the compound of formula (III) is

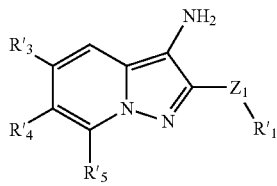

wherein
$Z_1$ is chosen from:
covalent single bonds;
divalent radicals chosen from radicals —$O(CH_2)_p$—, wherein p is an integer ranging from 0 to 6; radicals —$NR'_6(CH_2)_q(C_6H_4)_t$—, wherein q is an integer ranging from 0 to 6, t is chosen from 0 and 1, and $R'_6$ is chosen from hydrogen atoms and $C_1$-$C_6$ alkyl radicals optionally substituted with at least one hydroxyl group;
divalent radical chosen from —S—, —SO— and —$SO_2$— when $R'_1$ is a methyl radical;

$R'_1$ is chosen from:
hydrogen atoms;
$C_1$-$C_{10}$ alkyl radicals, which are optionally substituted and optionally interrupted with at least one group chosen from heteroatoms, O, N, Si, S, SO, and $SO_2$;
halogen atoms;
$SO_3H$ radicals;
5- to 8-membered rings which are optionally substituted, optionally saturated, optionally aromatic, and optionally comprising at least one of heteroatoms and groups chosen from N, O, S, $SO_2$, and —CO—, the ring optionally being cationic and and optionally substituted with a cationic radical;
groups —$N^+R_{17}R_{18}R_{19}$, wherein $R_{17}$, $R_{18}$ and $R_{19}$ are chosen from linear and branched $C_1$-$C_5$ alkyls optionally substituted with and least one hydroxyl group;
wherein when $Z_1$ is a covalent bond, then $R'_1$ may also be chosen from the radicals:
optionally substituted $C_1$-$C_6$ alkylcarbonyls;
—O—CO—R, —CO—O—R, NR—CO—R' and —CO—NRR', wherein R and R' independently are chosen from hydrogen atoms and optionally substituted $C_1$-$C_6$ alkyl radicals;

$R'_3$, $R'_4$ and $R'_5$, which may be identical or different, are chosen from:
hydrogen atoms;
hydroxyl radicals;
$C_1$-$C_6$ alkoxy radicals;
$C_1$-$C_6$ alkylthio radicals;
amino radicals;
monoalkylamino radicals;
$C_1$-$C_6$ dialkylamino radicals wherein the alkyl radicals may form, with the nitrogen atom to which they are attached, an optionally saturated, optionally aromatic 5- to 8-membered heterocycle, which may comprise at least one heteroatom and group chosen from N, O, S, $SO_2$ and CO, the heterocycle being optionally cationic, and optionally substituted with a cationic radical;
optionally substituted $C_1$-$C_6$ alkylcarbonyl radicals;
radicals —O—CO—R, —CO—O—R, NR—CO—R', and —CO—NRR', wherein R and R' independently are chosen from hydrogen atoms and optionally substituted $C_1$-$C_6$ alkyl radicals;
halogen radicals;
$SO_3H$ radicals;
optionally substituted $C_1$-$C_4$ alkyl radicals; and
saturated, unsaturated and aromatic, optionally substituted carbon-based rings;
and
$R'_3$, $R'_4$ and $R'_5$, may form in pairs a partially saturated or unsaturated ring.

11. The composition according to claim 10, wherein $Z_1$ is chosen from covalent bonds, radicals —$NR'_6(CH_2)_q$—, and radical —$O(CH_2)_p$—, and $R'_1$ is a cationic radical.

12. The composition according to claim 1, wherein the aminopyrazolopyridine oxidation bases of formula (II) are chosen from:

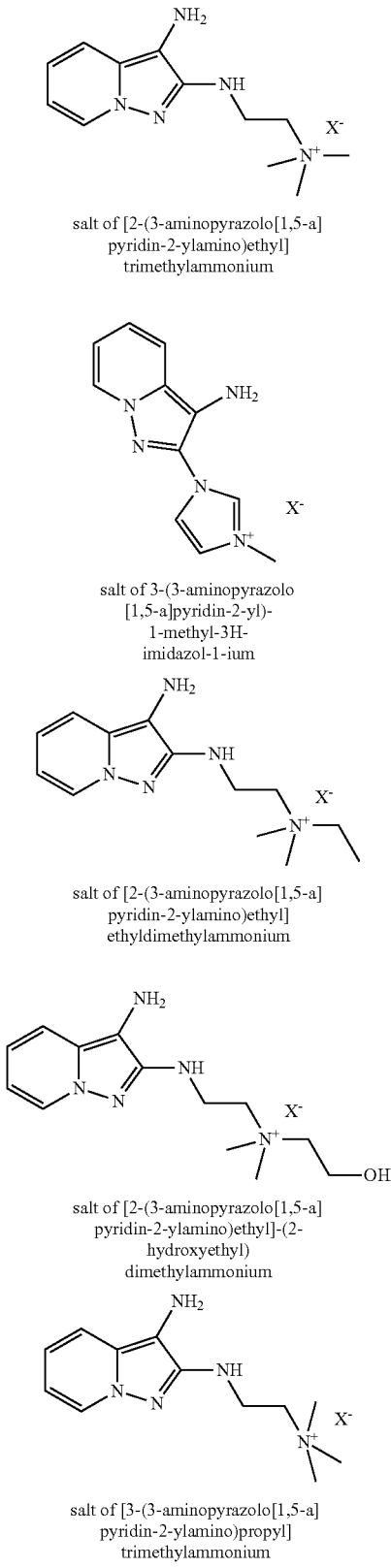

salt of [2-(3-aminopyrazolo[1,5-a]
pyridin-2-ylamino)ethyl]
trimethylammonium salt of 3-(3-aminopyrazolo
[1,5-a]pyridin-2-yl)-
1-methyl-3H-
imidazol-1-ium salt of [2-(3-aminopyrazolo[1,5-a]
pyridin-2-ylamino)ethyl]
ethyldimethylammonium salt of [2-(3-aminopyrazolo[1,5-a]
pyridin-2-ylamino)ethyl]-(2-
hydroxyethyl)
dimethylammonium salt of [3-(3-aminopyrazolo[1,5-a]
pyridin-2-ylamino)propyl]
trimethylammonium -continued

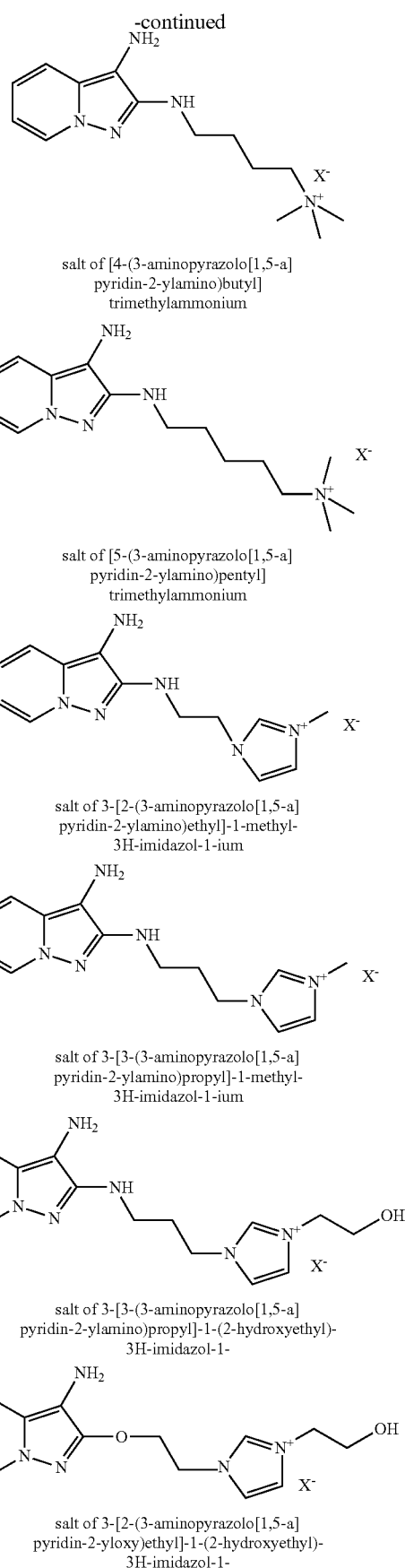

salt of [4-(3-aminopyrazolo[1,5-a]
pyridin-2-ylamino)butyl]
trimethylammonium salt of [5-(3-aminopyrazolo[1,5-a]
pyridin-2-ylamino)pentyl]
trimethylammonium salt of 3-[2-(3-aminopyrazolo[1,5-a]
pyridin-2-ylamino)ethyl]-1-methyl-
3H-imidazol-1-ium salt of 3-[3-(3-aminopyrazolo[1,5-a]
pyridin-2-ylamino)propyl]-1-methyl-
3H-imidazol-1-ium salt of 3-[3-(3-aminopyrazolo[1,5-a]
pyridin-2-ylamino)propyl]-1-(2-hydroxyethyl)-
3H-imidazol-1- salt of 3-[2-(3-aminopyrazolo[1,5-a]
pyridin-2-yloxy)ethyl]-1-(2-hydroxyethyl)-
3H-imidazol-1-

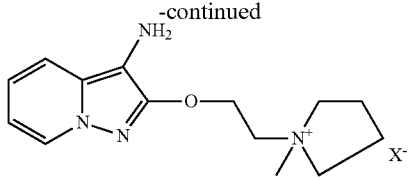

salt of 1-{2-[(3-aminopyrazolo[1,5-a]
pyridin-2-yl)oxy]ethyl}-1-methylpyrrolidinium

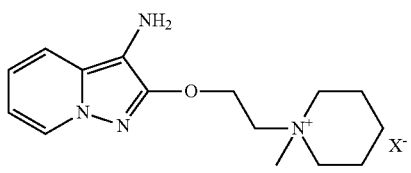

salt of 1-{2-[(3-aminopyrazolo[1,5-a]
pyridin-2-yl)oxy]ethyl}-1-methylpiperidinium

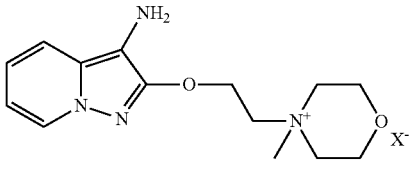

salt of 4-{2-[(3-aminopyrazolo[1,5-a]
pyridin-2-yl)oxy]ethyl}-4-
methylmorpholin-4-ium

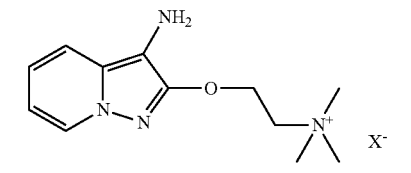

salt of {2-[(3-aminopyrazolo[1,5-a]
pyridin-2-yl)oxy]ethyl}
trimethylammonium

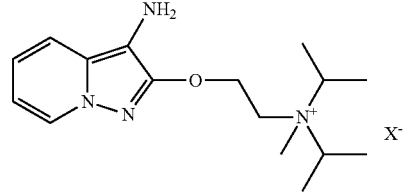

salt of {2-[(3-aminopyrazolo[1,5-a]
pyridin-2-yl)oxy]ethyl}
diisopropylmethylammonium

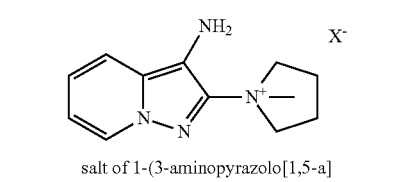

salt of 1-(3-aminopyrazolo[1,5-a]
pyridin-2-yl)-1-methylpyrrolidinium

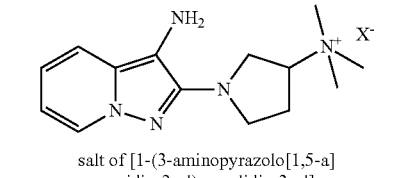

salt of [1-(3-aminopyrazolo[1,5-a]
pyridin-2-yl)pyrrolidin-3-yl]
trimethylammonium

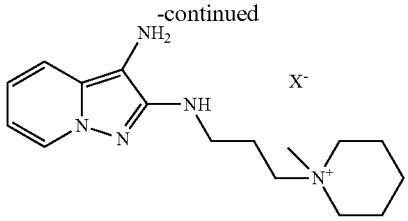

salt of 1-[3-(3-aminopyrazolo[1,5-a]
pyridin-2-ylamino)propyl]-1-
methylpiperidinium

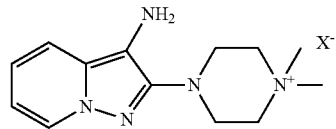

salt of 4-(3-aminopyrazolo[1,5-a]
pyridin-2-yl)-1,1-
dimethylpiperazin-1-ium

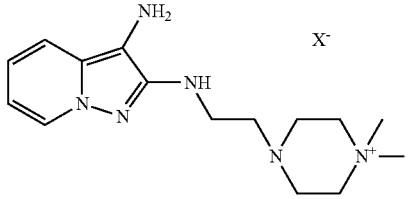

salt of 4-[2-(3-aminopyrazolo[1,5-a]
pyridin-2-ylamino)ethyl]-1, 1-
dimethylpiperazin-1-ium

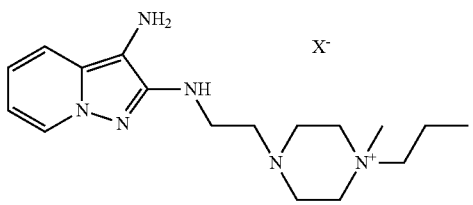

salt of 4-[2-(3-aminopyrazolo[1,5-a]
pyridin-2-ylamino)ethyl]-1-methyl-1-
propylpiperazin-1-ium

salt of 4-(3-aminopyrazolo[1,5-a]
pyridin-2-yl)-1-(2-hydroxyethyl)
piperazin-1-ium

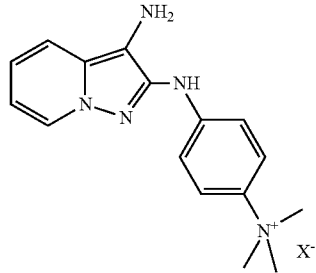

salt of [4-(3-aminopyrazolo[1,5-a]
pyridin-2-ylamino)phenyl]
trimethylammonium

77

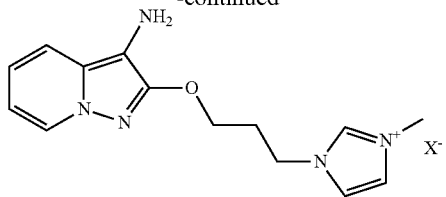

salt of 3-[3-(3-aminopyrazolo[1,5-a]
pyridin-2-yloxy)propyl]-1-methyl-
3H-imidazol-1-ium

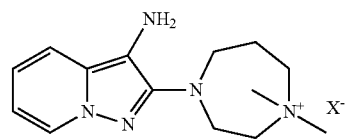

salt of 4-(3-aminopyrazolo[1,5-a]
pyridin-2-yl)-1,1-dimethyl-
[1,4]diazepan-1-ium

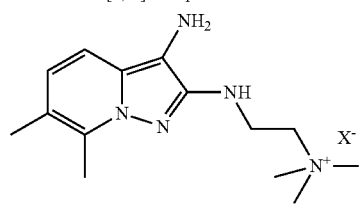

salt of [2-(3-amino-6,7-
dimethylpyrazolo[1,5-a]
pyridin-2-ylamino)ethyl]
trimethylammonium

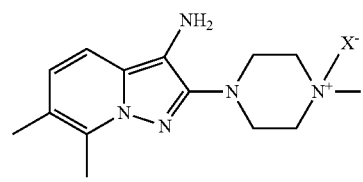

salt of 4-(3-amino-6,7-
dimethylpyrazolo[1,5-a]
pyridin-2-yl)-1,1-
dimethylpiperazin-1-ium

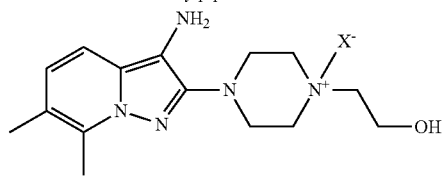

salt of 4-(3-amino-6,7-
dimethylpyrazolo[1,5-a]
pyridin-2-yl)-1-(2-hydroxyethyl)-1-
methylpiperazin-1-

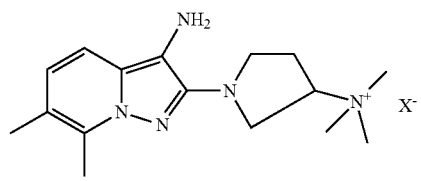

salt of [1-(3-amino-6,7-
dimethylpyrazolo[1,5-a]
pyridin-2-yl)pyrrolidin-3-yl]
trimethylammonium

78

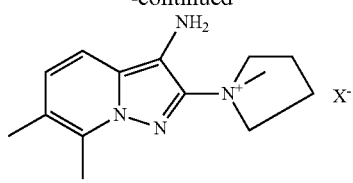

salt of 1-(3-amino-6,7-
dimethylpyrazolo[1,5-a]
pyridin-2-yl)-1-
methylpyrrolidinum

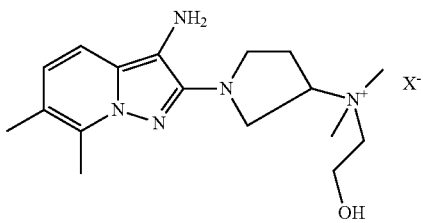

salt of [1-(3-amino-6,7-
dimethylpyrazolo[1,5-a]
pyridin-2-yl)pyrrolidin-3-yl]-
(2-hydroxyethyl)
dimethylammonium

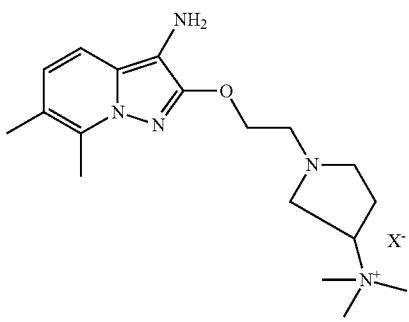

salt of {1-[2-(3-amino-6,7-dimethylpyrazolo[1,5-a]
pyridin-2-yloxy)ethyl]pyrrolidin-3-yl}
trimethylammonium

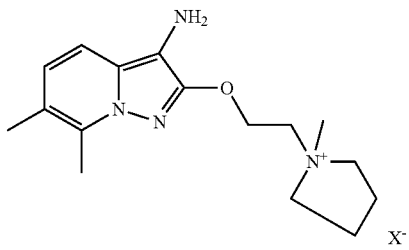

salt of 1-{2-[(3-amino-6,7-
dimethylpyrazolo[1,5-a]
pyridin-2-yl)oxy]ethyl}-1-
methylpyrrolidinium

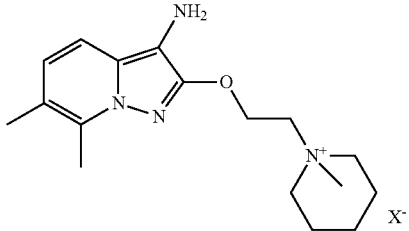

salt of 1-{2-[(3-amino-6,7-
dimethylpyrazolo[1,5-a]
pyridin-2-yl)oxy]ethyl}-1-
methylpiperidinium -continued

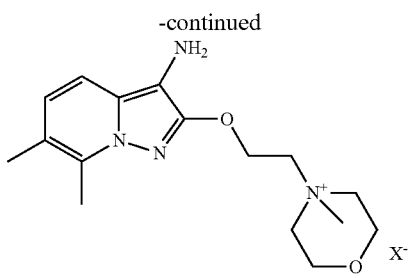

salt of 4-{2-[(3-amino-6,7-dimethylpyrazolo[1,5-a]pyridin-2-yl)oxy]ethyl}-4-methylmorpholin-4-ium

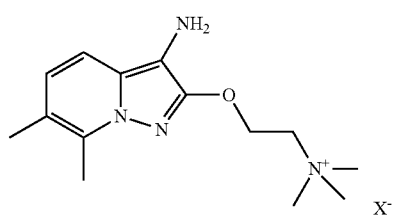

salt of {2-[(3-amino-6,7-dimethylpyrazolo[1,5-a]pyridin-2-yl)oxy]ethyl}trimethylammonium

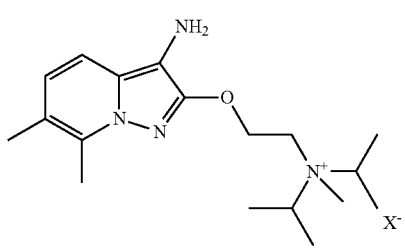

salt of {2-[(3-amino-6,7-dimethylpyrazolo[1,5-a]pyridin-2-yl)oxy]ethyl}diisopropylmethylammonium

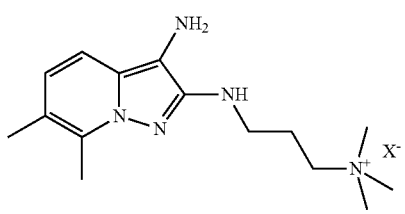

salt of [3-(3-amino-6,7-dimethylpyrazolo[1,5-a]pyridin-2-ylamino)propyl]trimethylammonium

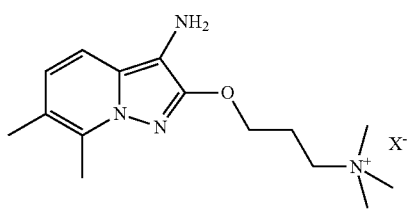

salt of [3-(3-amino-6,7-dimethylpyrazolo[1,5-a]pyridin-2-yloxy)propyl]trimethylammonium -continued

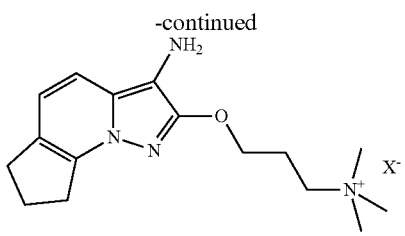

salt of [3-(3-amino-7,8-dihydro-6H-cyclopenta[e]pyrazolo[1,5-a]pyridin-2-yloxy)propyl]trimethylammonium

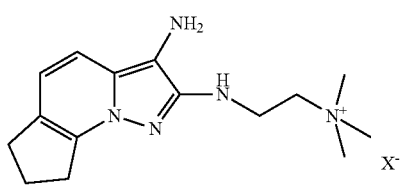

salt of {2-[(3-amino-7,8-dihydro-6H-cyclopenta[e]pyrazolo[1,5-a]pyridin-2-yl)amino]ethyl}trimethylammonium

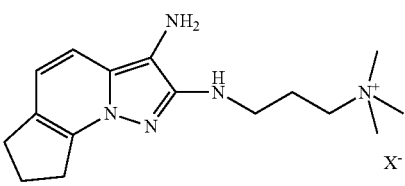

salt of {3-[(3-amino-7,8-dihydro-6H-cyclopenta[e]pyrazolo[1,5-a]pyridin-2-yl)amino]propyl}trimethylammonium

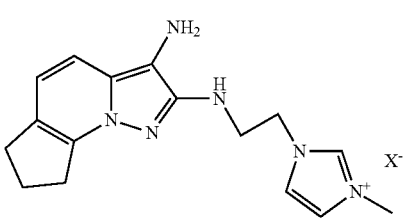

salt of 1-{2-[(3-amino-7,8-dihydro-6H-cyclopenta[e]pyrazolo[1,5-a]pyridin-2-yl)amino]ethyl}-3-methyl-1H-imidazol-3-ium

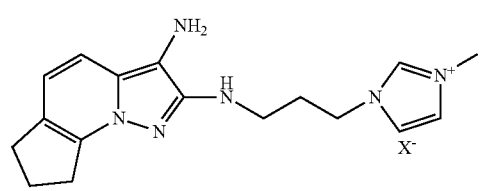

salt of 1-{3-[(3-amino-7,8-dihydro-6H-cyclopenta[e]pyrazolo[1,5-a]pyridin-2-yl)amino]propyl}-3-methyl-1H-imidazol-3-ium

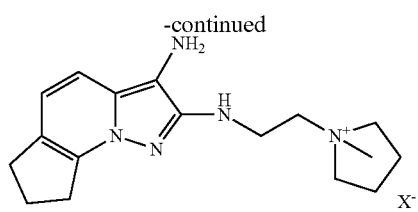

salt of 1-{2-[(3-amino-7,8-dihydro-6H-cyclopenta[e]pyrazolo[1,5-a]pyridin-2-yl)amino]ethyl}-1-methylpyrrolidinium

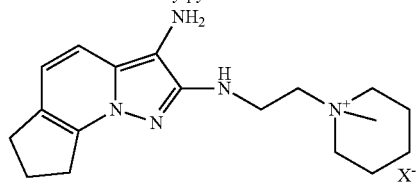

salt of 1-{2-[(3-amino-7,8-dihydro-6H-cyclopenta[e]pyrazolo[1,5-a]pyridin-2-yl)amino]ethyl}-1-methylpiperidinium

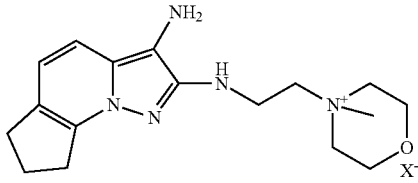

salt of 4-{2-[(3-amino-7,8-dihydro-6H-cyclopenta[e]pyrazolo[1,5-a]pyridin-2-yl)amino]ethyl}-4-methylmorpholin-4-ium

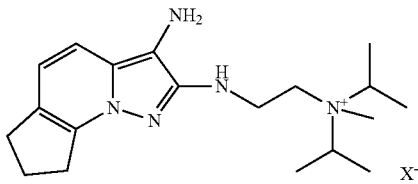

salt of {2-[(3-amino-7,8-dihydro-6H-cyclopenta[e]pyrazolo[1,5-a]pyridin-2-yl)amino]ethyl}-diisopropylmethylammonium

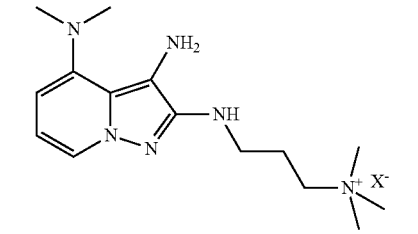

salt of [3-(3-amino-4-dimethylaminopyrazolo[1,5-a]pyridin-2-ylamino)propyl]trimethylammonium

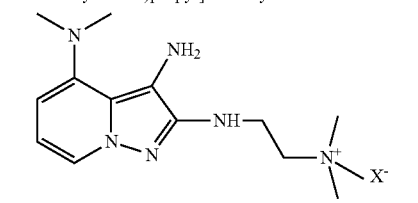

salt of [2-(3-amino-4-dimethylaminopyrazolo[1,5-a]pyridin-2-ylamino)ethyl]trimethylammonium

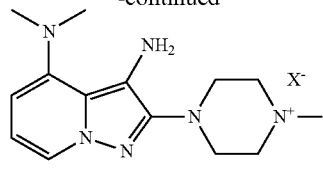

salt of 4-(3-amino-4-dimethylaminopyrazolo[1,5-a]pyridin-2-yl)-1-methyl-piperazin-1-ium

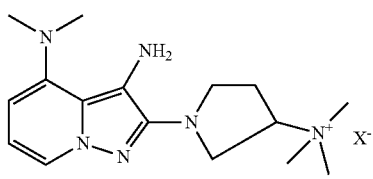

salt of [1-(3-amino-4-dimethylaminopyrazolo[1,5-a]pyridin-2-yl)-pyrrolidin-3-yl]trimethylammonium

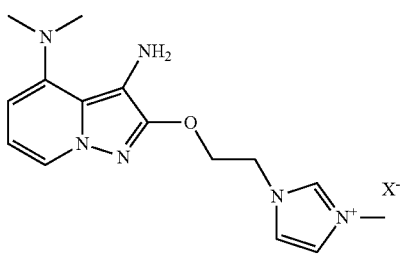

salt of 3-[2-(3-amino-4-dimethylaminopyrazolo[1,5-a]pyridin-2-yloxy)ethyl]-1-methyl-3H-imidazol-1-ium

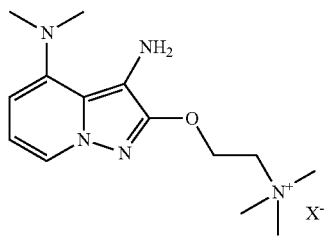

salt of [2-(3-amino-4-dimethylaminopyrazolo[1,5-a]pyridin-2-yloxy)ethyl]trimethylammonium

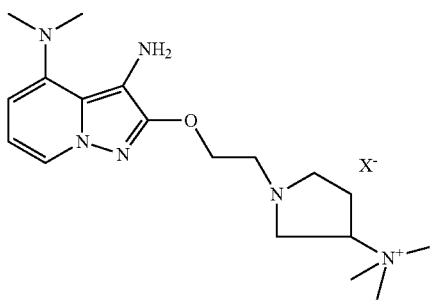

salt of {1-[2-(3-amino-4-dimethylaminopyrazolo[1,5-a]pyridin-2-yloxy)ethyl]pyrrolidin-3-yl}trimethylammonium

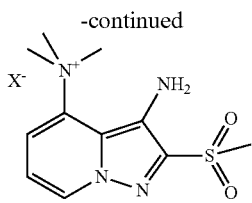

salt of (3-amino-2-methanesulfonylpyrazolo[1,5-a]pyridin-4-yl) trimethylammonium

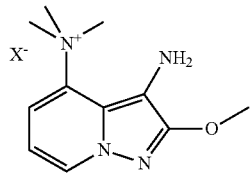

salt of (3-amino-2-methoxypyrazolo[1,5-a]pyridin-4-yl) trimethylammonium and the addition salts, solvates, and solvates of the salts thereof, wherein X is chosen from ions and groups of ions that provide the electronegativity of the derivative of formula (II).

13. The composition according to claim 1, wherein formulae (I) and (II) are chosen from:

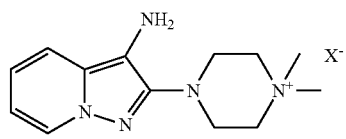

salts of 4-(3-aminopyrazolo[1,5-a]pyridin-2-yl)-1,1-dimethylpiperazin-1-ium

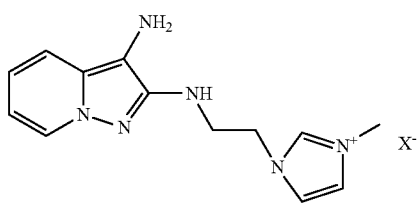

salts of 3-[2-(3-aminopyrazolo[1,5-a]pyridin-2-ylamino) ethyl]-1-methyl-3H-imidazol-1-ium and 2-[(3-aminopyrazolo[1,5-a]pyridin-2-yl)oxy]ethanol, the addition salts, solvates, and solvates of the salts thereof.

14. The composition according to claim 1, wherein, in formula (IV), $R_1$ and $R_2$ are chosen from $C_1$-$C_6$ alkyl radicals optionally substituted with at least one of hydroxyl, ($C_1$-$C_2$) alkoxy, amino, (di)($C_1$-$C_2$)alkylamino; phenyl, methoxyphenyl, ethoxyphenyl, and benzyl radicals.

15. The composition according to claim 1, wherein, in formula (IV), $R_1$ and $R_2$ form, together with the nitrogen atoms to which they are attached, are chosen from optionally substituted saturated and unsaturated 5- and 6-membered rings.

16. The composition according to claim 1, wherein, in formula (IV), $R_3$ and $R_4$ are chosen from hydrogen atoms; linear and branched $C_1$-$C_6$ alkyl radicals optionally substituted with at least one radical chosen from hydroxyl, ($C_1$-$C_2$) alkoxy, amino and (di)($C_1$-$C_2$)alkylamino radicals; and phenyl radicals optionally substituted with at least one radical chosen from hydroxyl, amino and ($C_1$-$C_2$)alkoxy radicals.

17. The composition according to claim 1, wherein, in formula (IV), $R_3$ and $R_4$ form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine and N-(2-hydroxyethyl)homopiperazine.

18. The composition according to claim 1, wherein the 4,5-diaminopyrazole derivatives of formula (I) and addition salts thereof are chosen from:
2,3-diamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
4,5-diamino-1,2-dimethyl-1,2-dihydropyrazol-3-one;
4,5-diamino-1,2-diethyl-1,2-dihydropyrazol-3-one;
4,5-diamino-1,2-bis(2-hydroxyethyl)-1,2-dihydropyrazol-3-one;
2-amino-3-(2-hydroxyethyl)amino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
4-amino-1,2-diethyl-5-(pyrrolidin-1-yl)-1,2-dihydropyrazol-3-one;
4-amino-5-(3-dimethylaminopyrrolidin-1-yl)-1,2-diethyl-1,2-dihydropyrazol-3-one; and
2,3-diamino-6-hydroxy-6,7-dihydro-1H,5H-pyrazolo[1,2-a]pyrazol-1-one.

19. The composition according to claim 1, wherein, in formula (IIa), $R'_1$ is chosen from hydrogen atoms and saturated $C_1$-$C_4$ alkyl radicals optionally substituted with a hydroxyl radical.

20. The composition according to claim 1, wherein, in formula (IIa), $R'_2$ and $R'_3$, which may be identical or different, are chosen from hydrogen atoms; $C_1$-$C_6$ alkyl radicals optionally substituted with at least one hydroxyl radical; carboxyl radicals; $C_1$-$C_4$ alkyl carboxylate radicals; and radicals $CONR'_7R'_8$.

21. The composition according to claim 1, wherein, in formula (IIa), $R'_4$ and $R'_5$ are identical and are hydrogen atoms.

22. The composition according to claim 1, wherein, in formula (IIa), $R'_6$ is chosen from linear and branched $C_1$-$C_6$ alkyl radicals; carboxyl radicals; $C_1$-$C_6$ alkyl carboxylates; carboxamide radicals; $(C_1$-$C_6)$alkoxy$(C_1$-$C_6)$alkyloxy radicals; $C_1$-$C_6$ alkoxy radicals; hydroxy$(C_1$-$C_6)$alkyloxy radicals; radicals O-Ak-$NR'_9R'_{10}$ wherein Ak is chosen from linear $C_1$-$C_6$ and branched $C_3$-$C_6$ divalent alkylene radicals optionally interrupted with a radical $NR'_7$.

23. The composition according to claim 1, wherein the 4-aminoindole derivatives of formula (IIa) are chosen from derivatives of formula (II'):

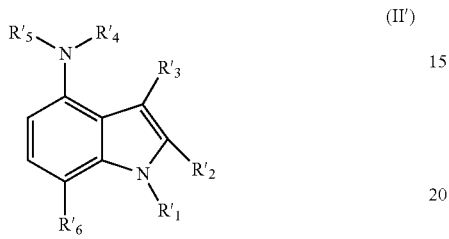

(II')

wherein
- $R'_1$ is chosen from hydrogen atoms and saturated $C_1$-$C_4$ alkyl radicals optionally substituted with a hydroxyl radical;
- $R'_2$ and $R'_3$, which may be identical or different, are chosen from hydrogen atoms; $C_1$-$C_6$ alkyl radicals optionally substituted with at least one hydroxyl radical; carboxyl radicals; $C_1$-$C_4$ alkyl carboxylate radicals; and radicals $CONR'_7R'_8$;
- $R'_4$ and $R'_5$ are hydrogen atoms;
- $R'_6$ is chosen from linear and branched $C_1$-$C_6$ alkyl radicals; carboxyl radicals; $C_1$-$C_6$ alkyl carboxylates; carboxamide radicals; $(C_1$-$C_6)$alkoxy$(C_1$-$C_6)$alkyloxy radicals; $C_1$-$C_6$ alkoxy radicals; $C_1$-$C_6$ hydroxyalkoxy radicals; and radicals O-Ak-$NR'_9R'_{10}$ wherein Ak is chosen from linear $C_1$-$C_6$ and branched $C_3$-$C_6$ divalent alkylene radicals, optionally interrupted with a radical $NR'_7$;
- $R'_7$ and $R'_8$ are independently chosen from hydrogen atoms and $C_1$-$C_6$ alkyl radicals optionally substituted with a hydroxyl radical;
- $R'_9$ and $R'_{10}$, which may be identical or different, are chosen from saturated linear $C_1$-$C_4$ alkyl radicals and unsaturated linear $C_2$-$C_4$ alkyl radicals; and
- $R'_9$ and $R'_{10}$ may form, with the nitrogen that bears them, an optionally saturated 5- to 8-membered heterocycle; one of the chain members optionally being chosen from oxygen atoms and radicals $NR'_{11}$ wherein $R'_{11}$ is chosen from H and $C_1$-$C_4$ alkyl radicals, optionally substituted with OH.

24. The composition according to claim 1, wherein the 4-aminoindole derivatives of formula (IIa) are chosen from:

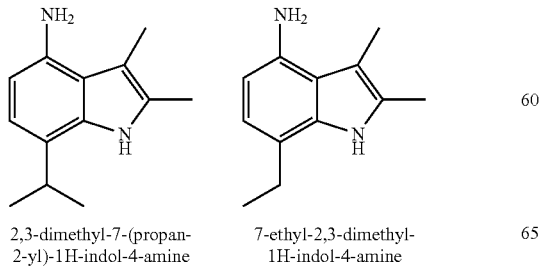

2,3-dimethyl-7-(propan-2-yl)-1H-indol-4-amine 7-ethyl-2,3-dimethyl-1H-indol-4-amine -continued

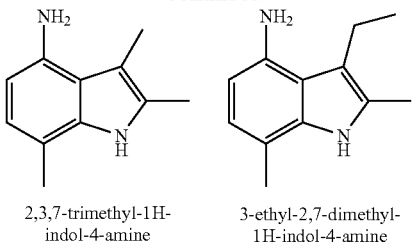

2,3,7-trimethyl-1H-indol-4-amine 3-ethyl-2,7-dimethyl-1H-indol-4-amine

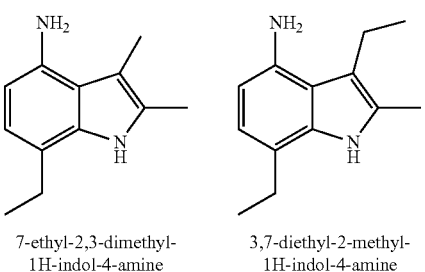

7-ethyl-2,3-dimethyl-1H-indol-4-amine 3,7-diethyl-2-methyl-1H-indol-4-amine

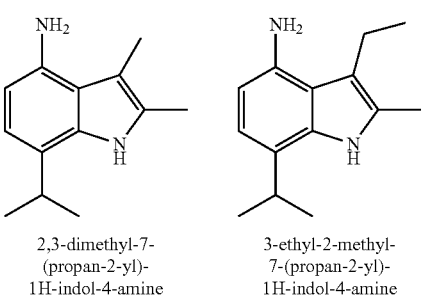

2,3-dimethyl-7-(propan-2-yl)-1H-indol-4-amine 3-ethyl-2-methyl-7-(propan-2-yl)-1H-indol-4-amine

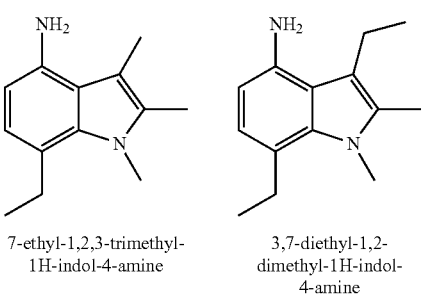

7-ethyl-1,2,3-trimethyl-1H-indol-4-amine 3,7-diethyl-1,2-dimethyl-1H-indol-4-amine

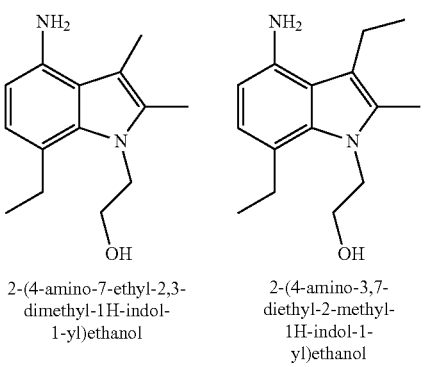

2-(4-amino-7-ethyl-2,3-dimethyl-1H-indol-1-yl)ethanol 2-(4-amino-3,7-diethyl-2-methyl-1H-indol-1-yl)ethanol -continued

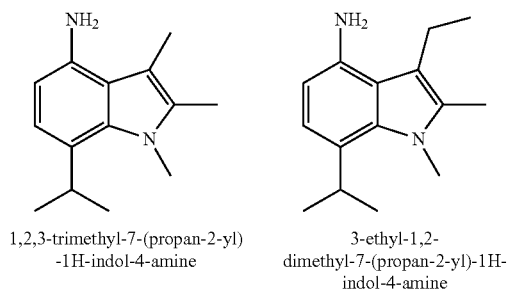

1,2,3-trimethyl-7-(propan-2-yl)-1H-indol-4-amine 3-ethyl-1,2-dimethyl-7-(propan-2-yl)-1H-indol-4-amine

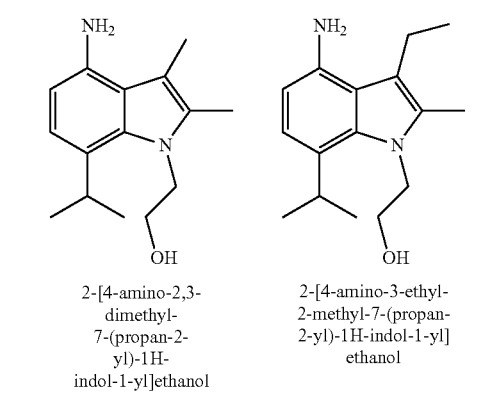

2-[4-amino-2,3-dimethyl-7-(propan-2-yl)-1H-indol-1-yl]ethanol

2-[4-amino-3-ethyl-2-methyl-7-(propan-2-yl)-1H-indol-1-yl]ethanol

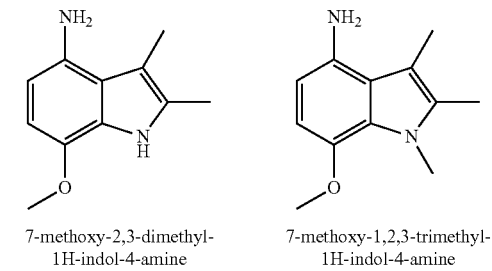

7-methoxy-2,3-dimethyl-1H-indol-4-amine 7-methoxy-1,2,3-trimethyl-1H-indol-4-amine

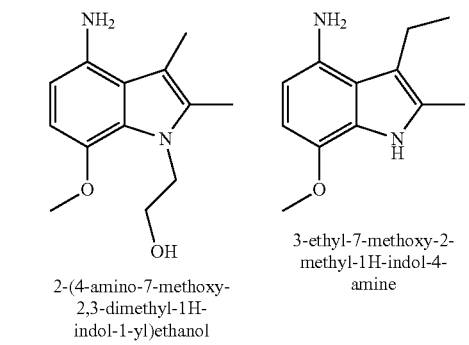

2-(4-amino-7-methoxy-2,3-dimethyl-1H-indol-1-yl)ethanol 3-ethyl-7-methoxy-2-methyl-1H-indol-4-amine

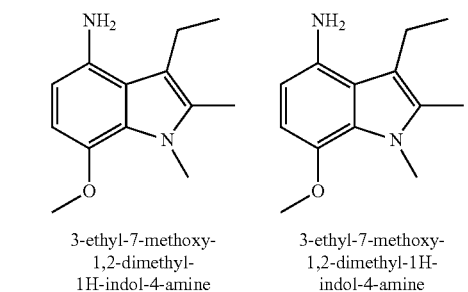

3-ethyl-7-methoxy-1,2-dimethyl-1H-indol-4-amine 3-ethyl-7-methoxy-1,2-dimethyl-1H-indol-4-amine -continued

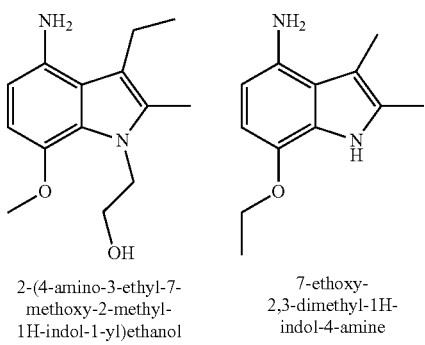

2-(4-amino-3-ethyl-7-methoxy-2-methyl-1H-indol-1-yl)ethanol 7-ethoxy-2,3-dimethyl-1H-indol-4-amine

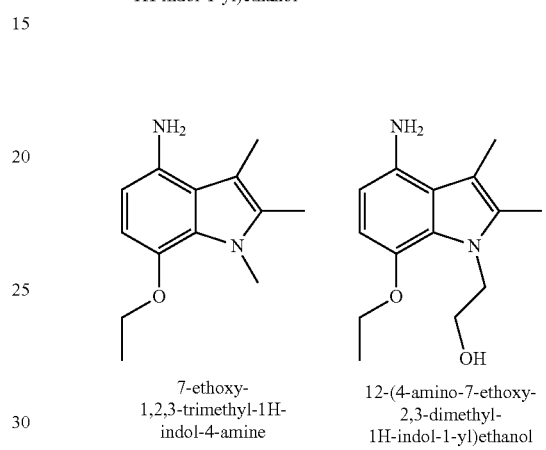

7-ethoxy-1,2,3-trimethyl-1H-indol-4-amine 12-(4-amino-7-ethoxy-2,3-dimethyl-1H-indol-1-yl)ethanol

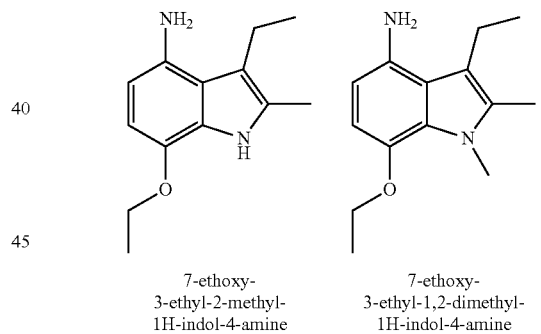

7-ethoxy-3-ethyl-2-methyl-1H-indol-4-amine 7-ethoxy-3-ethyl-1,2-dimethyl-1H-indol-4-amine

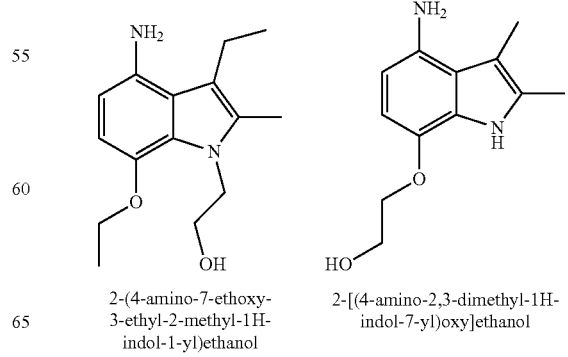

2-(4-amino-7-ethoxy-3-ethyl-2-methyl-1H-indol-1-yl)ethanol

2-[(4-amino-2,3-dimethyl-1H-indol-7-yl)oxy]ethanol

89
-continued

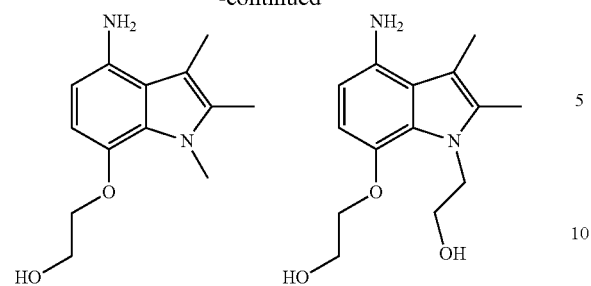

2-[(4-amino-1,2,3-trimethyl-1H-indol-7-yl)oxy]ethanol

2-[(4-amino-7-(2-hydroxyethoxy)-2,3-dimethyl-1H-indol-1-yl]ethanol

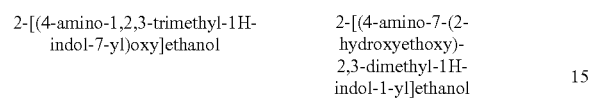

7-[2-(dimethylamino)ethoxy]-2,3-dimethyl-1H-indol-4-amine

7-[2-(dimethylamino)ethoxy]-1,2,3-trimethyl-1H-indol-4-amine

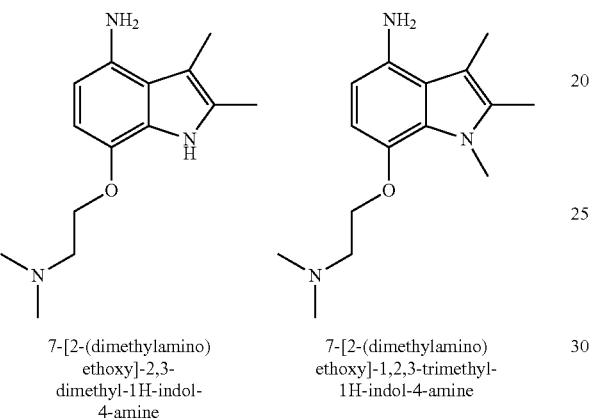

2-{4-amino-7-[2-(dimethylamino)ethoxy]-2,3-dimethyl-1H-indol-1-yl}ethanol 2,3-dimethyl-7-[2-(pyrrolidin-1-yl)ethoxy]-1H-indol-4-amine

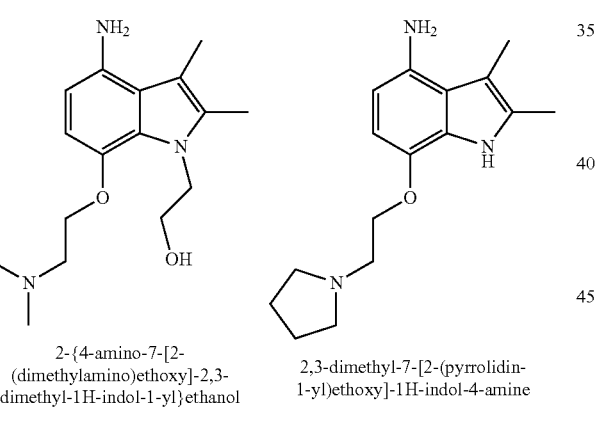

2,3-dimethyl-7-[2-(piperidin-1-yl)ethoxy]-1H-indol-4-amine

90
-continued

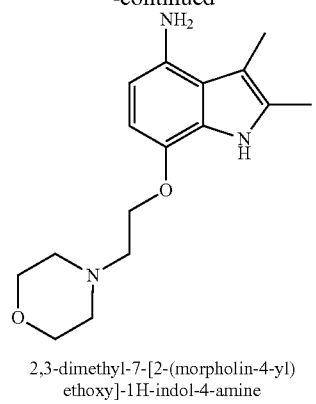

2,3-dimethyl-7-[2-(morpholin-4-yl)ethoxy]-1H-indol-4-amine

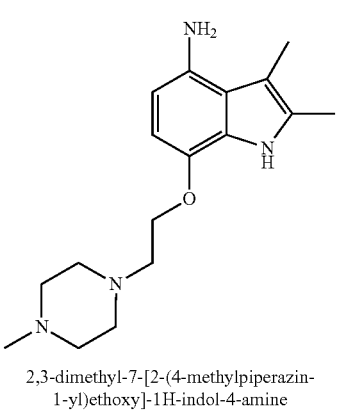

2,3-dimethyl-7-[2-(4-methylpiperazin-1-yl)ethoxy]-1H-indol-4-amine

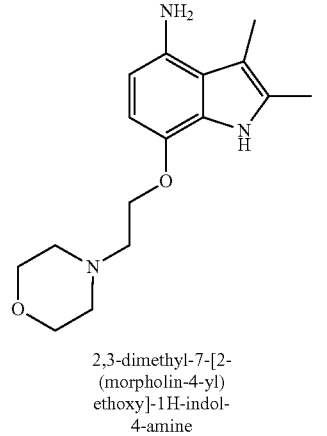

2,3-dimethyl-7-[2-(morpholin-4-yl)ethoxy]-1H-indol-4-amine

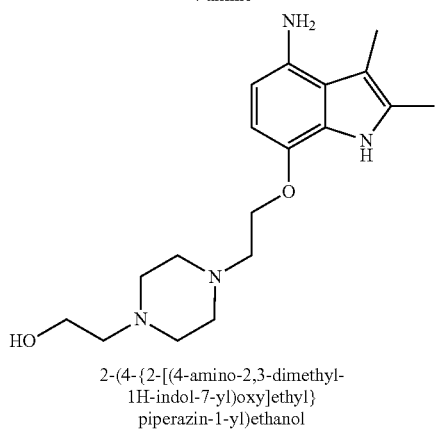

2-(4-{2-[(4-amino-2,3-dimethyl-1H-indol-7-yl)oxy]ethyl}piperazin-1-yl)ethanol

-continued

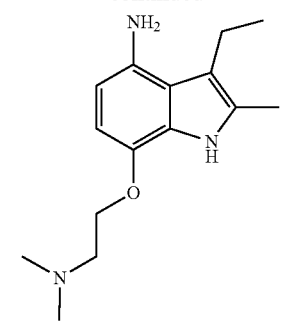

7-[2-dimethylamino)ethoxy]-3-ethyl-
2-methyl-1H-indol-4-amine

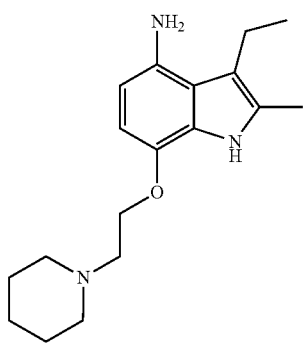

3-ethyl-2-methyl-7-[2-piperidin-1-yl)
ethoxy]-1H-indol-4-amine

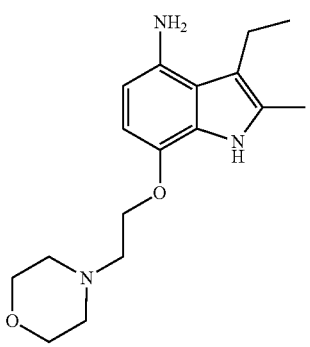

3-ethyl-2-methyl-7-[2-(morpholin-
4-yl)ethoxy]-1H-indol-4-amine

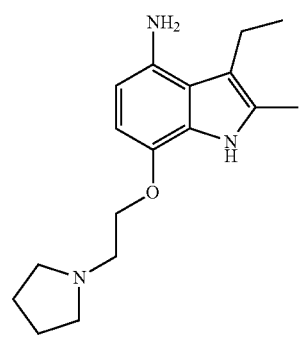

3-ethyl-2-methyl-7-[2-(pyrrolidin-
1-yl)ethoxy]-1H-indol-4-amine

-continued

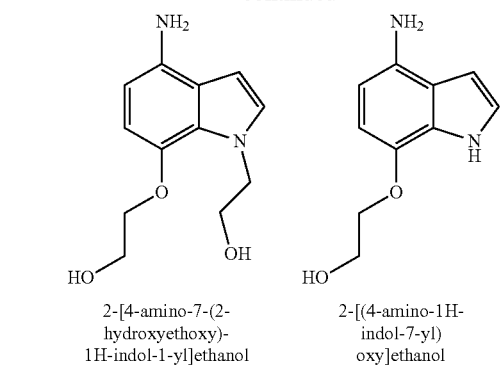

2-[4-amino-7-(2-
hydroxyethoxy)-
1H-indol-1-yl]ethanol

2-[(4-amino-1H-
indol-7-yl)
oxy]ethanol

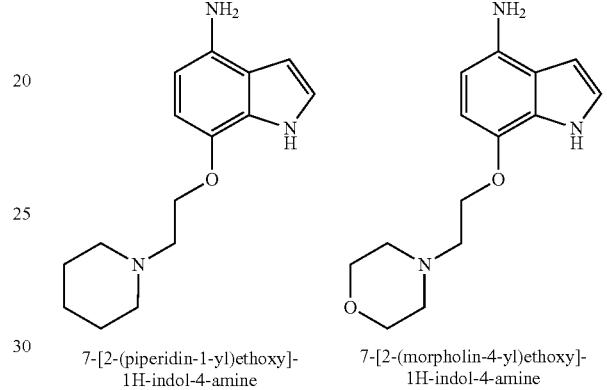

7-[2-(piperidin-1-yl)ethoxy]-
1H-indol-4-amine

7-[2-(morpholin-4-yl)ethoxy]-
1H-indol-4-amine

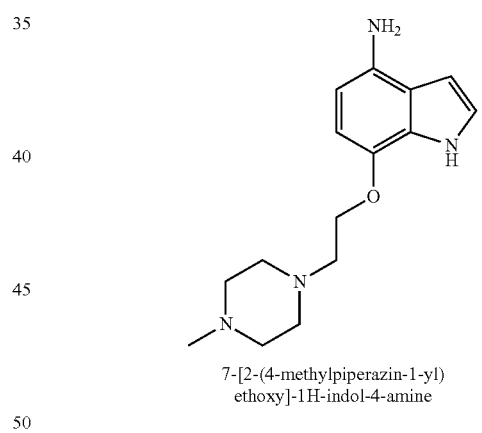

7-[2-(4-methylpiperazin-1-yl)
ethoxy]-1H-indol-4-amine

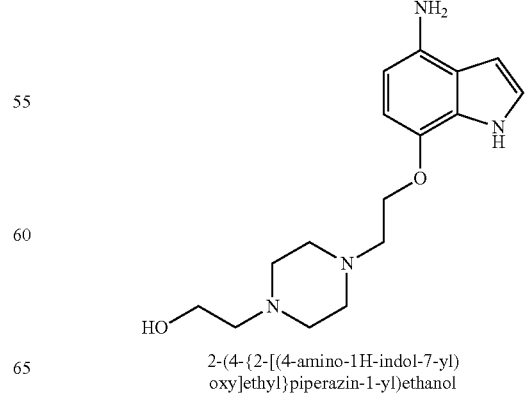

2-(4-{2-[(4-amino-1H-indol-7-yl)
oxy]ethyl}piperazin-1-yl)ethanol

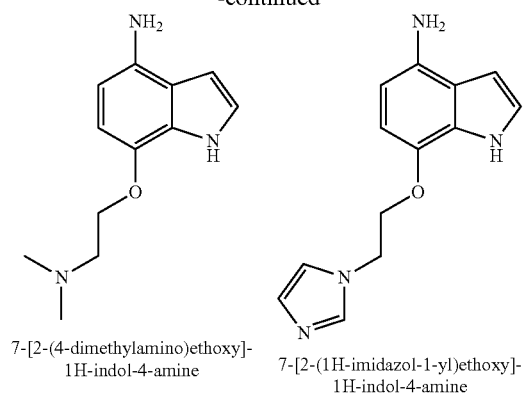

7-[2-(4-dimethylamino)ethoxy]-
1H-indol-4-amine

7-[2-(1H-imidazol-1-yl)ethoxy]-
1H-indol-4-amine

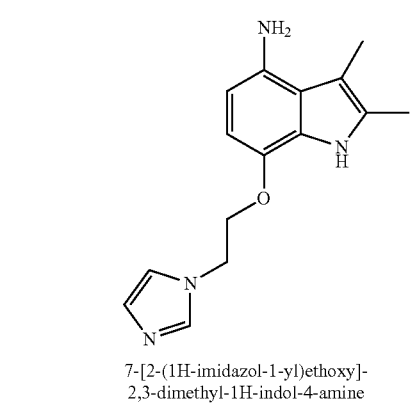

7-[2-(1H-imidazol-1-yl)ethoxy]-
2,3-dimethyl-1H-indol-4-amine

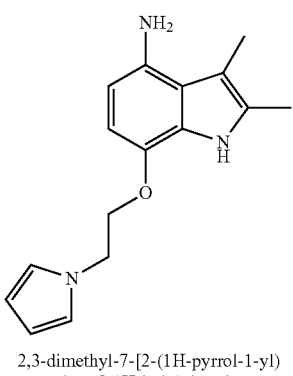

2,3-dimethyl-7-[2-(1H-pyrrol-1-yl)
ethoxy]-1H-indol-4-amine

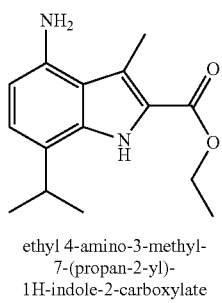

ethyl 4-amino-3-methyl-
7-(propan-2-yl)-
1H-indole-2-carboxylate

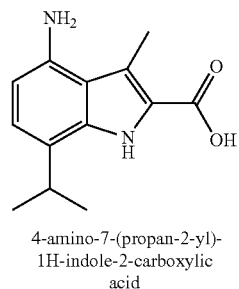

4-amino-7-(propan-2-yl)-
1H-indole-2-carboxylic
acid

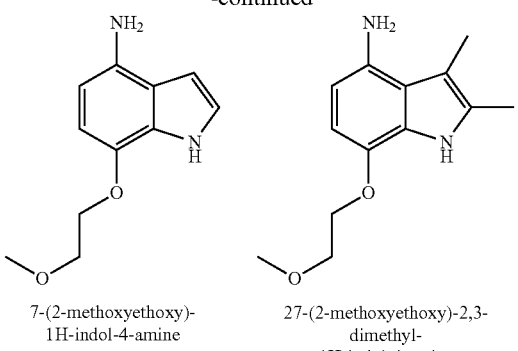

7-(2-methoxyethoxy)-
1H-indol-4-amine 27-(2-methoxyethoxy)-2,3-
dimethyl-
1H-indol-4-amine

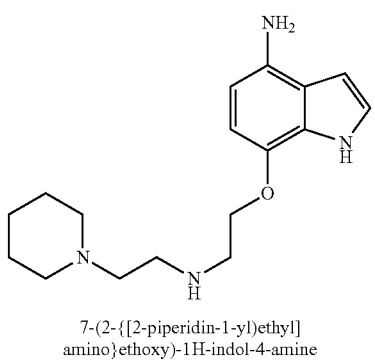

7-(2-{[2-piperidin-1-yl)ethyl]
amino}ethoxy)-1H-indol-4-amine

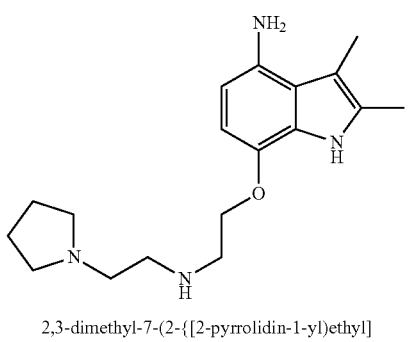

2,3-dimethyl-7-(2-{[2-pyrrolidin-1-yl)ethyl]
amino}ethoxy)-1H-indol-4-amine

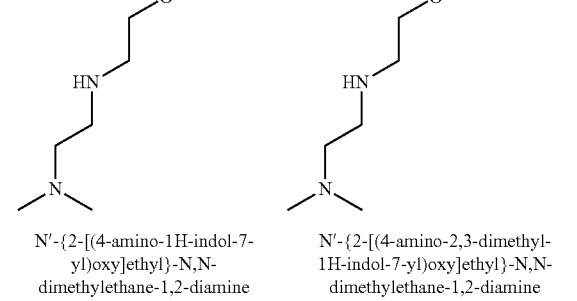

N'-{2-[(4-amino-1H-indol-7-
yl)oxy]ethyl}-N,N-
dimethylethane-1,2-diamine

N'-{2-[(4-amino-2,3-dimethyl-
1H-indol-7-yl)oxy]ethyl}-N,N-
dimethylethane-1,2-diamine -continued

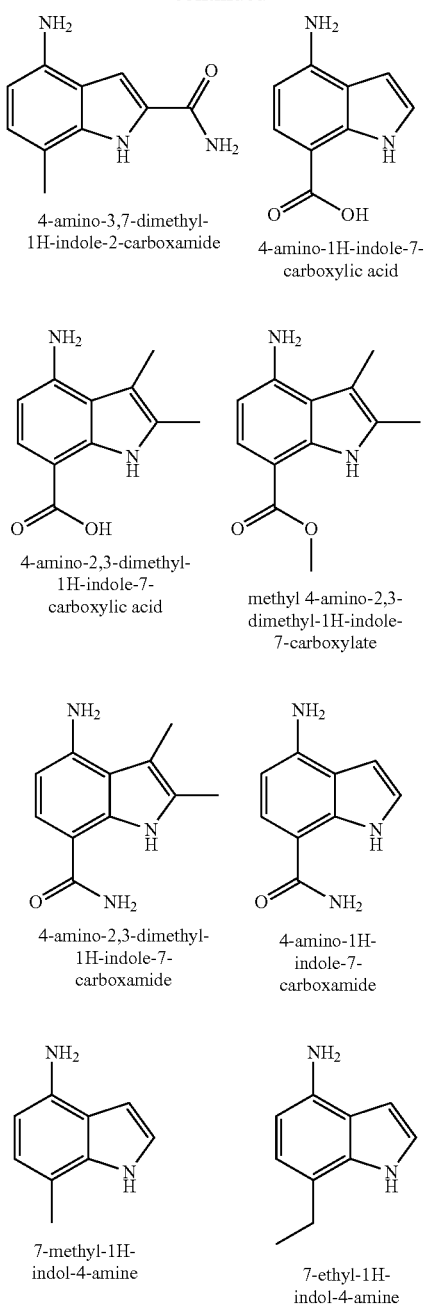

4-amino-3,7-dimethyl-1H-indole-2-carboxamide 4-amino-1H-indole-7-carboxylic acid 4-amino-2,3-dimethyl-1H-indole-7-carboxylic acid methyl 4-amino-2,3-dimethyl-1H-indole-7-carboxylate 4-amino-2,3-dimethyl-1H-indole-7-carboxamide 4-amino-1H-indole-7-carboxamide 7-methyl-1H-indol-4-amine 7-ethyl-1H-indol-4-amine and the addition salts, solvates, and solvates of the salts thereof.

25. The composition according to claim 1, further comprising at least one oxidizing agent.

26. A process for dyeing keratin fibers, comprising applying to the keratin fibers in the presence of at least one oxidizing agent for a time sufficient to develop the desired coloration, a composition comprising, in a cosmetically acceptable dyeing medium:

a) at least one oxidation base chosen from
4,5-diaminopyrazole derivatives of formula (I), and addition salts, solvates, and solvates of the salts thereof:

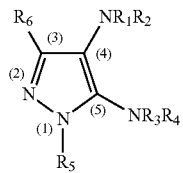

(I)

wherein:
$R_1$, $R_2$, $R_3$, $R_4$, $R_5$ and $R_6$, which may be identical or different, are chosen from hydrogen atoms and $C_1$-$C_6$ alkyl radicals which are optionally substituted with at least one substituent chosen from OR, NHR, NRR', SR, SOR, $SO_2R$, COR, COOH, $CONH_2$, CONHR, CONRR', $PO(OH)_2$, SH, $SO_3X$, non-cationic heterocycles, Cl, Br, and I, wherein X is chosen from hydrogen atoms, Na, K, and $NH_4$, and R and R', which may be identical or different, are chosen from $C_1$-$C_4$ alkyl radicals, $C_1$-$C_4$ alkenyl radicals; $C_2$-$C_4$ hydroxyalkyl radicals; $C_2$-$C_4$ aminoalkyl radicals; phenyl radicals; phenyl radicals substituted with at least one of halogen atoms, and $C_1$-$C_4$ alkyl radicals, $C_1$-$C_4$ alkoxy radicals, nitro radicals, trifluoromethyl radicals, amino radicals, $C_1$-$C_4$ alkylamino radicals; benzyl radicals; benzyl radicals substituted with at least one of halogen atoms and $C_1$-$C_4$ alkyl radicals, $C_1$-$C_4$ alkoxy radicals, methylenedioxy radicals, amino radicals; radicals having the formula:

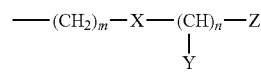

wherein m and n are integers, which may be identical or different, ranging from 0 to 3, X is chosen from oxygen atoms and NH groups, Y is chosen from hydrogen atoms and $C_1$-$C_4$ alkyl radicals, and Z is a methyl radical when n is equal to 0, or Z is chosen from $C_1$-$C_4$ alkyl radicals, OR groups, and NR"R''' groups when n is greater than or equal to 1, wherein R" and R''', which may be identical or different, are chosen from hydrogen atoms and $C_1$-$C_4$ alkyl radicals;
or $R_5$ forms, with the nitrogen atom of the group $NR_3R_4$ in position 5, a heterocycle that is at least 4-membered; wherein at least one of the radicals $R_1$, $R_2$, $R_3$ and $R_4$ is a hydrogen atom;
aminopyrazolopyridine oxidation bases of formula (II), and addition salts, solvates, and solvates of the salts thereof:

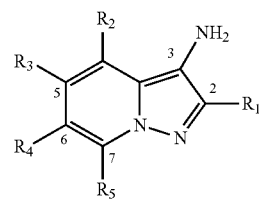

(II)

wherein:
$R_1$, $R_2$, $R_3$, $R_4$ and $R_5$, which may be identical or different, are chosen from hydrogen atoms, halogen atoms; radicals —$NHSO_3H$; hydroxyl radicals; radicals ($C_1$-$C_4$) alkyl; radicals ($C_1$-$C_4$)alkoxy; radicals ($C_1$-$C_4$)alkylthio; mono($C_1$-$C_4$)alkylamino radicals; radicals di($C_1$-

$C_4$)alkylamino wherein the two alkyl groups may form, together with the nitrogen atom to which they are attached, a ring that is optionally interrupted with at least one atom chosen from nitrogen, oxygen and sulfur atoms; heterocycles; nitro radicals; phenyl radicals; carbonyl radicals; ($C_1$-$C_4$)alkoxycarbonyl radicals; carboxamido radicals; cyano radicals; amino radicals; sulfonyl radicals; radicals —$CO_2H$, radicals —$SO_3H$; radicals —$PO_3H_2$; radicals —$PO_4H_2$; and groups:

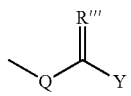

wherein R''' is chosen from oxygen and nitrogen atoms, Q is chosen from oxygen atoms, NH groups, and NH($C_1$-$C_4$)alkyl groups, and Y is chosen from hydroxyl, amino, $C_1$-$C_4$ alkyl, ($C_1$-$C_4$)alkoxy, ($C_1$-$C_4$)alkylamino and di($C_1$-$C_4$)alkylamino radicals;

aminopyrazolopyridine oxidation bases of formula (III)

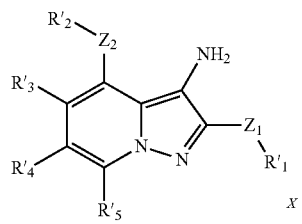

(III)

wherein:
$Z_1$ and $Z_2$, which may be identical or different, are chosen from:
covalent single bonds;
divalent radicals chosen from radicals —$O(CH_2)_p$—, wherein p is an integer ranging from 0 to 6; radicals —$NR'_6(CH_2)_q(C_6H_4)_t$—, wherein q is an integer ranging from 0 to 6, t is chosen from 0 and 1, and $R'_6$ is chosen from hydrogen atoms and $C_1$-$C_6$ alkyl radicals optionally substituted with at least one hydroxyl group;
$Z_1$ may also be a divalent radical chosen from —S—, —SO— and —$SO_2$— when $R'_1$ is a methyl radical;
$R'_1$ and $R'_2$, which may be identical or different, are chosen from:
hydrogen atoms;
$C_1$-$C_{10}$ alkyl radicals, which are optionally substituted and optionally interrupted with at least one group chosen from heteroatoms, O, N, Si, S, SO, and $SO_2$;
halogen atoms;
$SO_3H$ radicals;
5- to 8-membered rings which are optionally substituted, optionally saturated, optionally aromatic, and optionally comprising at least one of heteroatoms and groups chosen from N, O, S, $SO_2$, and —CO—, the ring optionally being cationic and optionally substituted with a cationic radical;
groups —$N^+R_{17}R_{18}R_{19}$, wherein $R_{17}$, $R_{18}$ and $R_{19}$ are independently chosen from linear and branched $C_1$-$C_5$ alkyls optionally substituted with and least one hydroxyl group;

wherein when $Z_1$ or, respectively, $Z_2$ is a covalent bond, then $R'_1$ or, respectively, $R'_2$ may also be chosen from the radicals:
optionally substituted $C_1$-$C_6$ alkylcarbonyls;
—O—CO—R, —CO—O—R, NR—CO—R' and —CO—NRR', wherein R and R' independently are chosen from hydrogen atoms and optionally substituted $C_1$-$C_6$ alkyl radicals;
$R'_3$, $R'_4$ and $R'_5$, which may be identical or different, are chosen from:
hydrogen atoms;
hydroxyl radicals;
$C_1$-$C_6$ alkoxy radicals;
$C_1$-$C_6$ alkylthio radicals;
amino radicals;
monoalkylamino radicals;
$C_1$-$C_6$ dialkylamino radicals wherein the alkyl radicals may form, with the nitrogen atom to which they are attached, an optionally saturated, optionally aromatic 5- to 8-membered heterocycle, which may comprise at least one heteroatom and group chosen from N, O, S, $SO_2$ and CO, the heterocycle being optionally cationic, and optionally substituted with a cationic radical;
optionally substituted $C_1$-$C_6$ alkylcarbonyl radicals;
radicals —O—CO—R, —CO—O—R, NR—CO—R', and —CO—NRR', wherein R and R' independently are chosen from hydrogen atoms and optionally substituted $C_1$-$C_6$ alkyl radicals;
halogen radicals;
$SO_3H$ radicals;
optionally substituted $C_1$-$C_4$ alkyl radicals;
saturated, unsaturated and aromatic, optionally substituted carbon-based rings;
$R'_3$, $R'_4$ and $R'_5$, may form in pairs a partially saturated or unsaturated ring;
X is chosen from ions and groups of ions that provide the electronegativity of the derivative of formula (II);
with the proviso that at least one of the groups $R'_1$ and $R'_2$ is a cationic radical;
oxidation bases chosen from the diamino-N,N-dihydropyrazolone derivatives of formula (IV), and addition salts, solvates, and solvates of the salts thereof:

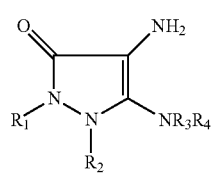

(IV)

wherein:
$R_1$, $R_2$, $R_3$ and $R_4$, which may be identical or different, are chosen from:
linear and branched $C_1$-$C_6$ alkyl radicals optionally substituted with at least one radical chosen from radicals $OR_5$, radicals $NR_6R_7$, carboxyl radicals, sulfonic radicals, carboxamido radicals $CONR_6R_7$, sulfonamido radicals $SO_2NR_6R_7$, heteroaryls, aryls optionally substituted with at least one group chosen from ($C_1$-$C_4$)alkyl, hydroxyl, $C_1$-$C_2$ alkoxy, amino and (di)alkyl($C_1$-$C_2$)amino groups;

aryl radicals optionally substituted with at least one group chosen from ($C_1$-$C_4$)alkyl, hydroxyl, $C_1$-$C_2$ alkoxy, amino and (di)alkyl($C_1$-$C_2$)amino groups;

5- and 6-membered heteroaryl radical, optionally substituted with at least one radical chosen from ($C_1$-$C_4$) alkyl and ($C_1$-$C_2$)alkoxy radicals;

$R_3$ and $R_4$ may also independently be chosen from hydrogen atoms;

wherein $R_5$, $R_6$ and $R_7$, which may be identical or different, are chosen from:

hydrogen atoms;

linear and branched $C_1$-$C_4$ alkyl radicals optionally substituted with at least one radical chosen from hydroxyl, $C_1$-$C_2$ alkoxy, carboxamido $CONR_8R_9$, sulfonyl $SO_2R_8$, aryl optionally substituted with a ($C_1$-$C_4$)alkyl, hydroxyl, $C_1$-$C_2$ alkoxy, amino and (di) alkyl($C_1$-$C_2$)amino; aryl optionally substituted with a ($C_1$-$C_4$)alkyl, hydroxyl, $C_1$-$C_2$ alkoxy, amino and (di) alkyl($C_1$-$C_2$)amino radicals;

$R_6$ and $R_7$, which may be identical or different, may also be chosen from carboxamido radicals $CONR_8R_9$ and sulfonyl radicals $SO_2R_8$;

$R_8$ and $R_9$, which may be identical or different, are chosen from hydrogen atoms; linear and branched $C_1$-$C_4$ alkyl radicals optionally substituted with at least one radical chosen from hydroxyl and $C_1$-$C_2$ alkoxy radicals;

at least one of $R_1$ and $R_2$ and $R_3$ and $R_4$ may form, with the nitrogen atoms to which they are attached, a saturated or unsaturated 5- to 7-membered heterocycle optionally substituted with at least one radical chosen from halogen atoms, amino, (di)alkyl ($C_1$-$C_4$)amino, hydroxyl, carboxyl, carboxamido and ($C_1$-$C_2$)alkoxy radicals, $C_1$-$C_4$ alkyl radicals optionally substituted with at least one hydroxyl, amino, (di)alkylamino, alkoxy, carboxyl and sulfonyl radicals;

$R_3$ and $R_4$ may also form, together with the nitrogen atom to which they are attached, a 5- or 7-membered heterocycle wherein the carbon atoms may be replaced with an optionally substituted oxygen or nitrogen atom;

and b) at least one coupler chosen from the 4-aminoindole derivatives of formula (IIa), and addition salts, solvates, and solvates of the salts thereof:

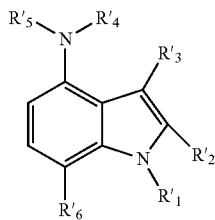

(IIa)

wherein:

$R'_1$ is chosen from hydrogen atoms; and linear and branched saturated $C_1$-$C_6$ alkyl radicals, optionally interrupted with an oxygen atom or a radical $NR'_7$, and optionally substituted with a radical chosen from OH and $NR'_7R'_8$;

$R'_2$ and $R'_3$, which may be identical or different, are chosen from hydrogen atoms;

$C_1$-$C_6$ alkyl radicals, optionally substituted with at least one hydroxyl radical;

$C_1$-$C_6$ alkyl carboxylate radicals;

carboxyl radicals; and radicals $CONR'_7R'_8$;

$R'_4$ and $R'_5$, which may be identical or different, are chosen from hydrogen atoms; and $C_1$-$C_6$ alkyl radicals;

$R'_6$ is chosen from halogen atoms;

linear and branched $C_1$-$C_{10}$ alkyl radicals, optionally interrupted with a heteroatom chosen from O and radicals $NR'_9$, and optionally substituted with at least one radical, which may be identical or different, chosen from OH and $NR'_7R'_8$;

carboxyl radicals;

$C_1$-$C_{10}$ alkyl carboxylates;

radicals $CONR'_7R'_8$;

$C_1$-$C_{10}$ alkoxy radicals and $C_1$-$C_{10}$ (poly)hydroxyalkoxy radicals;

(poly)($C_1$-$C_{10}$)alkoxy($C_1$-$C_{10}$)alkyloxy radicals; and radicals O-Ak-$NR'_9R'_{10}$ wherein Ak is chosen from linear $C_1$-$C_8$ and branched $C_3$-$C_8$ divalent alkylene radicals, optionally interrupted with at least one oxygen atom and optionally interrupted with at least one group $NR'_7$; wherein $R'_7$ and $R'_8$, which may be identical or different, are chosen from hydrogen atoms;

$C_1$-$C_8$ alkyl radicals optionally substituted with at least one hydroxyl radical; and $R'_9$ and $R'_{10}$, which may be identical or different, are chosen from linear and branched, saturated and unsaturated $C_1$-$C_4$ alkyl radicals;

wherein $R'_9$ and $R'_{10}$ may form, with the nitrogen that bears them, an optionally saturated 5- to 8-membered heterocycle, wherein one of the chain members is optionally chosen from oxygen atoms and radicals $NR'_{11}$, wherein $R'_{11}$ is chosen from H and $C_1$-$C_4$ alkyl radicals, optionally substituted with at least one radical chosen from OH and $NR'_7R'_8$.

* * * * *